US010758511B2

(12) United States Patent
Connor et al.

(10) Patent No.: US 10,758,511 B2
(45) Date of Patent: Sep. 1, 2020

(54) STABLE ANALOGS OF CYP450 LIPID METABOLITES AND INHIBITORS OF SOLUBLE EPOXIDE HYDROLASE

(71) Applicants: Massachusetts Eye and Ear Infirmary, Boston, MA (US); THE REGENTS OF THE UNIVERSITY OF CALIFORNIA, Oakland, CA (US)

(72) Inventors: Kip M. Connor, Newton, MA (US); Eiichi Hasegawa, Fukuoka (JP); Bruce D. Hammock, Davis, CA (US); Kin Sing Stephen Lee, Davis, CA (US)

(73) Assignees: Massachusetts Eye and Ear Infirmary, Boston, MA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 15/777,141

(22) PCT Filed: Nov. 17, 2016

(86) PCT No.: PCT/US2016/062492
§ 371 (c)(1),
(2) Date: May 17, 2018

(87) PCT Pub. No.: WO2017/087647
PCT Pub. Date: May 26, 2017

(65) Prior Publication Data
US 2018/0325860 A1 Nov. 15, 2018

Related U.S. Application Data

(60) Provisional application No. 62/365,289, filed on Jul. 21, 2016, provisional application No. 62/256,609, filed on Nov. 17, 2015.

(51) Int. Cl.
| | | |
|---|---|---|
| *A61K 31/17* | (2006.01) | |
| *A61K 31/202* | (2006.01) | |
| *A61K 31/336* | (2006.01) | |
| *A61K 31/445* | (2006.01) | |
| *A61K 31/4468* | (2006.01) | |
| *A61P 27/02* | (2006.01) | |
| *A61P 27/04* | (2006.01) | |
| *A61P 27/06* | (2006.01) | |
| *A61K 9/00* | (2006.01) | |

(52) U.S. Cl.
CPC .......... *A61K 31/336* (2013.01); *A61K 9/0019* (2013.01); *A61K 9/0048* (2013.01); *A61K 31/17* (2013.01); *A61K 31/202* (2013.01); *A61K 31/445* (2013.01); *A61P 27/02* (2018.01); *A61P 27/04* (2018.01); *A61P 27/06* (2018.01); *A61K 31/4468* (2013.01); *A61K 2300/00* (2013.01)

(58) Field of Classification Search
CPC .... A61K 31/17; A61K 31/202; A61K 31/336; A61K 31/445; A61K 31/4468; A61K 9/0019; A61K 9/0048; A61P 27/02; A61P 27/04; A61P 27/06
See application file for complete search history.

(56) References Cited

U.S. PATENT DOCUMENTS

2008/0221104 A1   9/2008   Hsu
2015/0335603 A1   11/2015  Connor et al.

FOREIGN PATENT DOCUMENTS

| WO | WO 2007/009001 | 1/2007 |
|----|----------------|--------|
| WO | WO 2009/129508 | 10/2009 |
| WO | WO 2011/097221 | 8/2011 |
| WO | WO 2014/110261 | 7/2014 |

OTHER PUBLICATIONS

Ansari, "Drug Interaction and Pharmacist" *J Young Pharm*, 2010, vol. 2, No. 3, pp. 326-331.
Almulki et al., "Surprising up-regulation of P-selectin glycoprotein ligand-1 (PSGL-1) in endotoxin-induced uveitis," FASEB J, 2009, 23(3):929-939.
Ambati & Fowler, "Mechanisms of age-related macular degeneration," Neuron, 2012, 75(1):26-39.
Arnold et al., "Arachidonic acid-metabolizing cytochrome P450 enzymes are targets of {omega}-3 fatty acids," J Biol Chem, 2010, 285(43):32720-32733.
Arnold et al., "Cytochrome P450-dependent metabolism of omega-6 and omega-3 long-chain polyunsaturated fatty acids," Pharmacol Rep, 2010, 62(3):536-547.
Askari et al., "Roles of the epoxygenase CYP2J2 in the endothelium," Prostaglandins Other Lipid Mediat, Dec. 2013, 107: 18 pages.
Borhan et al., "Mechanism of soluble epoxide hydrolase: Formation of an a-hydroxy ester-enzyme intermediate through Asp-333," J. Biol. Chem, 1995, 270(45):26923-26930.
Capra et al., "Transcellular biosynthesis of eicosanoid lipid mediators," Biochim Biophys Acta, 2015, 1851(4):377-382.
Chew et al., "Lutein + Zeaxanthin and Omega-3 Fatty Acids for Age-Related Macular Degeneration: The Age-Related Eye Disease Study 2 (AREDS2) Randomized Clinical Trial," JAMA, 2013, 1-11.
Chiamvimonvat et al., "The soluble epoxide hydrolase as a pharmaceutical target for hypertension," J Cardiovasc Phamacol, 2007, 50:225-237.

(Continued)

*Primary Examiner* — Sarah Pihonak
(74) *Attorney, Agent, or Firm* — Fish & Richardson P.C.

(57) ABSTRACT

This disclosure relates to methods of reducing inflammation, angiogenesis, vascular leakage and neovascularization by administering to a subject in need thereof one or more stable analogs of CYP450 lipid metabolites (e.g., eicosanoids) and one or more inhibitors of a soluble epoxide hydrolase (sEH). This disclosure also relates to methods of treating disorders associated with inflammation, angiogenesis, vascular leakage and neovascularization by administering to a subject in need thereof one or more stable analogs of CYP450 lipid metabolites (e.g., eicosanoids) and one or more inhibitors of a soluble epoxide hydrolase (sEH). This disclosure further relates to pharmaceutical compositions and kits comprising at least one stable analog of CYP450 lipid metabolites (e.g., eicosanoids) and at least one inhibitor of a soluble epoxide hydrolase (sEH).

2 Claims, 41 Drawing Sheets

(56) References Cited

OTHER PUBLICATIONS

Connor et al., "Increased dietary intake of omega-3-polyunsaturated fatty acids reduces pathological retinal angiogenesis," Nature Medicine, 2007, 13(7)868-73.
Cui et al., "The omega-3 epoxide of eicosapentaenoic acid inhibits endothelial cell proliferation by p38 MAP kinase activation and cyclin D1/CDK4 down-regulation," Br J Pharmacol, 2011, 162(5):1143-1155.
Deng et al., "Endothelial CYP epoxygenase overexpression and soluble epoxide hydrolase disruption attenuate acute vascular inflammatory responses in mice," FASEB J, 2011, 25(2):703-713.
Edin et al., "Endothelial expression of human cytochrome P450 epoxygenase CYP2C8 increases susceptibility to ischemia-reperfusion injury in isolated mouse heart," FASEB J, 2011, 25(10):3436-3447.
Falck JR, et al., "11,12-epoxyeicosatrienoic acid (11,12-EET): structural determinants for inhibition of TNF-alpha-induced VCAM-1 expression," Bioorg Med Chem Lett, 2003, 13(22):4011-4014.
Falck JR, et al., "17(R),18(S)-epoxyeicosatetraenoic acid, a potent eicosapentaenoic acid (EPA) derived regulator of cardiomyocyte contraction: structure-activity relationships and stable analogues," J Med Chem, 2011, 54(12):4109-4118.
Fer et al., "Metabolism of eicosapentaenoic and docosahexaenoic acids by recombinant human cytochromes P450," Arch Biochem Biophys, 2008, 471(2):116-125.
Funk, "Prostaglandins and leukotrienes: advances in eicosanoid biology," Science, 2001, 294(5548):1871-1875.
Gragoudas et al., "Pegaptanib for neovascular age-related macular degeneration," The New England Journal of Medicine, 2004, 351(27):2805-2816.
Hafezi-Moghadam et al., A novel mouse-driven ex vivo flow chamber for the study of leukocyte and platelet function. Am J Physiol Cell Physiol, 2004, 286(4):C876-892.
Harris et al., "Inhibition of soluble epoxide hydrolase attenuates hepatic fibrosis and endoplasmic reticulum stress induced by carbon tetrachloride in mice," Toxicol Appl Pharmacol, 2015, 286(2): 102-111.
Hui et al., "Targeted deletions of cyclooxygenase-2 and atherogenesis in mice," Circulation, 2010, 121(24):2654-2660.
Hwang et al., "Orally bioavailable potent soluble epoxide hydrolase inhibitors," J Med Chem, 2007, 50(16):3825-40.
Imig, "Epoxides and soluble epoxide hydrolase in cardiovascular physiology," Physiol Rev, 2012, 92(1):101-130.
Inceoglu et al., "Inhibition of soluble epoxide hydrolase reduces LPS-induced thermal hyperalgesia and mechanical allodynia in a rat model of inflammatory pain," Life Sci, 2006, 79(24):2311-9.
International Preliminary Report on Patentability in International Application No. PCT/US2016/62492, dated May 31, 2018, 11 pages.
International Search Report and Written Opinion in International Application No. PCT/US2016/62492, dated Jan. 31, 2017, 16 pages.
Kim et al., "1,3-Disubstituted Ureas Functionalized with Ether Groups are Potent Inhibitors of the Soluble. Epoxide Hydrolase with Improved Pharmacokinetic Properties," J. Med. Chem, 2007, 50: 5217-5226.
Lee et al., "Förster resonance energy transfer (FRET) competitive displacement assay for human soluble epoxide hydrolase," Anal Biochem, 2013, 434(2):259-268.
Lee et al., "Endothelial expression of human cytochrome P450 epoxygenases lowers blood pressure and attenuates hypertension-induced renal injury in mice," FASEB J, 2010, 24(10):3770-3781.
Lee et al., "Optimized inhibitors of soluble epoxide hydrolase improve in vitro target residence time and in vivo efficacy," J Med Chem, 2014, 57(16):7016-30.
Ley et al., "Getting to the site of inflammation: the leukocyte adhesion cascade updated," Nat Rev Immunol, 2007, 7(9):678-689.
Lim et al., "Age-related macular degeneration," Lancet, 2012, 379(9827):1728-1738.
Liu et al., "Substituted phenyl groups improve the pharmacokinetic profile and anti-inflammatory effect of urea-based soluble epoxide hydrolase inhibitors in murine models," Eur J Pharm Sci, 2013, 48(4-5):619-627.
Lois et al., "Retinal pigment epithelial atrophy in patients with exudative age-related macular degeneration undergoing anti-vascular endothelial growth factor therapy," Retina, 2013, 33(1):13-22.
Lucas et al., "Stereoselective epoxidation of the last double bond of polyunsaturated fatty acids by human cytochromes P450," J Lipid Res, May 2010, 51(5): 1125-1133.
Merle et al., "Circulating omega-3 Fatty acids and neovascular age-related macular degeneration," Invest Ophthalmol Vis Sci, 2014, 55(3):2010-2019.
Miller, "Age-related macular degeneration revisited—piecing the puzzle: the LXIX Edward Jackson memorial lecture," Am J Ophthalmol, 2013, 155(1):1-35 e13.
Mitroulis et al., "Leukocyte integrins: role in leukocyte recruitment and as therapeutic targets in inflammatory disease," Pharmacol Ther, 2015, 147:123-135.
Morisseau and Hammock, "Impact of soluble epoxide hydrolase and epoxyeicosanoids on human health," Annu. Rev. Pharmacol. Toxicol, 2013, 53:37-58.
Morisseau et al., "Potent urea and carbamate inhibitors of soluble epoxide hydrolases," PNAS, 1999, 96(16):8849-8854.
Mulki et al., "Assessing leukocyte-endothelial interactions under flow conditions in an ex vivo autoperfused microflow chamber assay," J Vis Exp, 2014, 94: e52130.
Ng & Adamis, "Anti-VEGF aptamer (pegaptanib) therapy for ocular vascular diseases," Ann N Y Acad Sci, 2006, 1082:151-171.
Noda et al., "Vascular adhesion protein-1 blockade suppresses choroidal neovascularization," FASEB J, 2008, 22(8):2928-2935.
Node et al., "Anti-inflammatory properties of cytochrome P450 epoxygenase-derived eicosanoids," Science, 1999, 285(5431):1276-1279.
Ota and Hammock, "Cytosolic and microsomal epoxide hydrolases: differential properties in mammalian liver," Science, 1980, 207:1479-1481.
Panigrahy, "EET signaling in cancer," Cancer Metastasis Rev, 2011, 30(3-4):525-540.
Panigrahy et al., "Epoxyeicosanoids stimulate multiorgan metastasis and tumor dormancy escape in mice," The Journal of Clinical Investigation, 2012, 122: 178-191.
Pritchard et al., "14, 15-Epoxyeicosatrienoic acid promotes endothelial cell dependent adhesion of human monocytic tumor U937 cells," Biochem Biophys Res Commun, 1990, 167(1):137-142.
Reynolds et al., "Dietary omega-3 Fatty acids, other fat intake, genetic susceptibility, and progression to incident geographic atrophy," Ophthalmology, 2013, 120(5):1020-1028.
Rinaldo-Matthis and Haeggstrom, "Structures and mechanisms of enzymes in the leukotriene cascade," Biochimie, 2010, 92(6):676-681.
Rose et al., "1-Aryl-3-(1-acylpiperidin-4-yl)urea inhibitors of human and murine soluble epoxide hydrolase: structure-activity relationships, pharmacokinetics, and reduction of inflammatory pain," J Med Chem, 2010, 53(19):7067-7075.
Rosenfeld et al., "Ranibizumab for neovascular age-related macular degeneration," N Engl J Med, 2006, 355(14):1419-1431.
Sakurai et al., "Targeted disruption of the CD18 or ICAM-1 gene inhibits choroidal neovascularization," Invest Ophthalmol Vis Sci, 2003, 44(6):2743-2749.
SanGiovanni and Chew, "The role of omega-3 long-chain polyunsaturated fatty acids in health and disease of the retina," Prog Retin Eye Res, 2005, 24(1):87-138.
SanGiovanni et al., "The relationship of dietary lipid intake and age-related macular degeneration in a case-control study: AREDS Report No. 20," Archives of Ophthalmology, 2007, 125(5):671-679.
SanGiovanni et al., "DNA sequence variants in PPARGC1A, a gene encoding a coactivator of the omega-3 LCPUFA sensing PPAR-RXR transcription complex, are associated with NV AMD and AMD-associated loci in genes of complement and VEGF signaling pathways," PLoS One, 2013, 8(1):e53155.

(56) References Cited

OTHER PUBLICATIONS

Sapieha et al., "5-Lipoxygenase Metabolite 4-HDHA Is a Mediator of the Antiangiogenic Effect of {omega}-3 Polyunsaturated Fatty Acids," Science Translational Medicine, 2011, 3(69):69 ra12.
Schmitz and Ecker, "The opposing effects of n-3 and n-6 fatty acids," Prog Lipid Res, 2008, 47(2):147-155.
Schunck et al., "Cytochrome P450 Derived Eicosanoids and Vascular Function in Coronary Artery Disease Patients," Atherosclerosis, 2013, 227: 442-448.
Seddon et al., "Dietary fat and risk for advanced age-related macular degeneration," Archives of Ophthalmology, 2001, 119(8):1191-199.
Serhan and Savill, "Resolution of inflammation: the beginning programs the end," Nature Immunology, 2005, 6(12):1191-1197.
Shen and Hammock, "Discovery of inhibitors of soluble epoxide hydrolase: a target with multiple potential therapeutic indications," 2012, J. Med. Chem. 55(5):1789-1808.
Simmons et al., "Cyclooxygenase isozymes: the biology of prostaglandin synthesis and inhibition," Pharmacol Rev, 2004, 56(3):387-437.
Sinal et al., "Targeted disruption of soluble epoxide hydrolase reveals a role in blood pressure regulation," J Biol Chem, 2000, 275(51):40504-40510.
Sirish et al., "Unique mechanistic insights into the beneficial effects of soluble epoxide hydrolase inhitbitors in the prevention of cardiac fibrosis," PNAS, 21013, 110(14):5618-23.
Smith et al., "Dietary fat and fish intake and age-related maculopathy," Archives of Ophthalmology, 2000, 118(3):401-404.
Souied et al., "Oral docosahexaenoic acid in the prevention of exudative age-related macular degeneration: the Nutritional AMD Treatment 2 study," Ophthalmology, 2013, 120(8):1619-1631.
Stahl et al., "PPARγ mediates the anti-angiogenic effects of ω3-PUFAs in proliferative retinopathy," Circulation Research, 2010, 107(4):495-500.
Strauss et al., "Altered behavioral phenotypes in soluble epoxide hydrolase knockout mice: Effects of traumatic brain injury," Prostaglandins Other Lipid Mediat, 2012.
Tsai et al., "Pharmacokinetic screening of soluble epoxide hydrolase inhibitors in dogs," Eur. J. Pharm. Sci, 2010, 40(3):222-238.
Ulu et al., "Pharmacokinetics and in vivo potency of soluble epoxide hydrolase inhibitors in cynomolgus monkey," Br J Pharmacol, 2012,165(5):1401-12.
Ulu et al., "Soluble epoxide hydrolase inhibitors reduce the development of atherosclerosis in apolipoprotein e-knockout mouse model," J Cardiovasc Pharmacol, 2008, 52(4):314-23.
Ulu et al., "An omega-3 epoxide of docosahexaenoic acid lowers blood pressure in angiotensin-II-dependent hypertension," J Cardiovasc Pharmacol, 2014, 64(1):87-99.
Wagner et al., "The role of long chain fatty acids and their epoxide metabolites in nociceptive signaling," Prostaglandins Other Lipid Mediat, 2014, 113-115:2-12.
Wang and Dubois, "Eicosanoids and cancer," Nat Rev Cancer, 2010, 10(3):181-193.
Wang and Dubois, "Epoxyeicosatrienoic acids: a double-edged sword in cardiovascular diseases and cancer," J Clin Invest, 2012, 122(1):19-22.
Wang et al., "Microsomal prostaglandin e2 synthase-1 modulates the response to vascular injury," Circulation, 2011, 123(6):631-639.
Wang et al., "Arachidonic acid epoxygenase metabolites stimulate endothelial cell growth and angiogenesis via mitogen-activated protein kinase and phosphatidylinositol 3-kinase/Akt signaling pathways," J Pharmacol Exp Ther, 2005, 314(2):522-532.
Webler et al., "Epoxyeicosatrienoic acids are part of the VEGF-activated signaling cascade leading to angiogenesis," Am J Physiol Cell Physiol, 2008, 295(5):C1292-1301.
Westphal et al., "CYP2J2 overexpression protects against arrhythmia susceptibility in cardiac hypertrophy," PLoS One, 2013, 8(8):e73490.
Westphal et al., "CYP-eicosanoids—a new link between omega-3 fatty acids and cardiac disease?," Prostaglandins Other Lipid Mediat, 2011, 96(1-4):99-108.
Yanai et al., "Cytochrome P450-generated metabolites derived from omega-3 fatty acids attenuate neovascularization," PNAS, 2014, 111(26):9603-9608.
Yu et al., "Soluble Epoxide Hydrolase Regulates Hydrolysis of Vasoactive Epoxyeicosatrienoic Acids," Circulation Research, 2000, 87: 992-998.
Zhang et al., "Epoxy metabolites of docosahexaenoic acid (DHA) inhibit angiogenesis, tumor growth, and metastasis," PNAS, 2013, 110(16):6530-6535.
Zhou et al., "Soluble epoxide hydrolase inhibitor 1-trifluoromethoxyphenyl-3-(1-propionylpiperidin-4-yl) urea attenuates bleomycin-induced pulmonary fibrosis in mice," Cell Tissue Res, 2016, 363: 399-409.
EP Extended European Search Report in European Appln. No. 16867124.6, dated Jul. 1, 2019, 12 pages.
Hasegawa et al., "Cytochrome P450 monooxygenase lipid metabolites are significant second messengers in the resolution of choroidal neovascularization," Proceedings of the National Academy of Sciences., Sep. 2017, 114(36):E7545-53.
Kitamura et al, "Potent NaturalSoluble Epoxide Hydrolase Inhibitors from Pentadiplandra brazzeana Bail Ion: Synthesis, Quantification, and Measurement of Biological Activities In Vitro and In Vivo," PLOS One, Feb. 2015, 10:e0117438.

STABLE ANALOGS OF CYP450 LIPID METABOLITES AND INHIBITORS OF SOLUBLE EPOXIDE HYDROLASE

CLAIM OF PRIORITY

This application is a 371 U.S. National Phase Application of PCT/US2016/062492, filed on Nov. 17, 20016, which claims the benefit of U.S. Provisional Application No. 62/256,609, filed Nov. 17, 2015; and U.S. Provisional Application No. 62/365,289, filed Jul. 21, 2016. The entire contents of the foregoing are hereby incorporated by reference.

FEDERALLY SPONSORED RESEARCH OR DEVELOPMENT

This invention was made with Government support under Grant No. R01 ES002710, Grant No. 1R01EY022084-01 and Grant No. 1R01EY022084-01S1 awarded by the National Institute of Health. The Government has certain rights in the invention.

TECHNICAL FIELD

This invention relates to methods of treating disorders associated with neovascularization, vascular leakage, inflammation and angiogenesis, and more particularly to using epoxymetabolites of a long chain polyunsaturated fatty acids and inhibitors of a soluble epoxide hydrolase to treat these disorders.

BACKGROUND

Age-related macular degeneration (AMD) is the most common cause of blindness for the elderly in the developed world. Choroidal neovascularization (CNV) is a hallmark of the neovascular (wet) form of advanced AMD and leads to significant vision loss.

There is a need for new nutritional or pharmacological interventions that are safe over the long term for the treatment or prevention of diseases associated with neovascularization (e.g., AMD).

SUMMARY

Provided herein are methods of reducing neovascularization, reducing choroidal neovascularization (CNV) lesions, reducing vascular leakage, reducing inflammation and reducing angiogenesis, e.g., reducing or reversing angiogenesis, in a subject by administering to a subject in need thereof one or more epoxymetabolites derived from omega-3 long chain polyunsaturated fatty acids (ω-3 LCPUFAs), e.g., cytochrome P450 (CYP) derived epoxymetabolites of docosahexaenoic acid (DHA), including epoxydocosapentaenoic acid (EDP) analogs (e.g., 7,8-EDP; 10,11-EDP; 13,14-EDP; 16,17-EDP, 19,20-EDP); and/or CYP-derived epoxymetabolites of eicosapentaenoic acid (EPA) including epoxyeicosaquatraenoic acid (EEQ) analogs (e.g., 8,9-EEQ; 11,12-EEQ; 14,15-EEQ; 17,18-EEQ), e.g., one or both of 17,18-epoxyeicosatetraenoic acid (EEQ) and 19,20-epoxydocosapentaenoic acid (EDP); and one or more inhibitors of soluble epoxide hydrolase (sEH), e.g., derivatives of urea (e.g., 1-(1-propionylpiperidin-4-yl)-3-(4-(trifluoromethoxy)phenyl)urea). The methods can be used for the treatment of conditions associated with inflammation and/or excess angiogenesis or neovascularization, including ophthalmological conditions such as age-related macular degeneration (AMD), diabetic retinopathy and cancer; conditions associated with increased vascular permeability, including stroke and cancer, and conditions associated with inflammation, e.g., arthritis or atherosclerosis.

The present application provides, inter alia, a method of treating or reducing the risk of a disorder associated with a neovascularization in a subject in need thereof, the method comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

The present application provides, inter alia, a method of treating or reducing the risk of a disorder associated with neovascularization in a subject in need thereof, the method comprising administering to the subject a therapeutically effective amount of at least one epoxymetabolite of a ω-3 long chain polyunsaturated fatty acid (LCPUFA), or a pharmaceutically acceptable salt thereof, and an effective amount of at least one inhibitor of a soluble epoxide hydrolase, or a pharmaceutically acceptable salt thereof.

In some embodiments, the neovascularization is corneal, retinal, choroidal, uveal, or iris neovascularization. In some embodiments, the neovascularization is choroidal neovascularization.

In some embodiments, the disorder is an ophthalmological disorder associated with neovascularization. In some embodiments, the ophthalmological disorder associated with neovascularization is age-related macular degeneration (AMD). In some embodiments, the ophthalmological disorder associated with neovascularization is Stargardt's disease. In some embodiments, the ophthalmological disorder associated with neovascularization is retinopathy. In some embodiments, the retinopathy is selected from a group consisting of retinopathy of prematurity (ROP), diabetic retinopathy, retinal vein occlusion, sickle cell retinopathy, and radiation retinopathy.

In some embodiments, the disorder is selected from the group consisting of dry eye disease, glaucoma, uveitis, retinal degeneration, dry age-related macular degeneration (AMD), retinopathy of prematurity, diabetic retinopathy, optic neuropathy, ischemia reperfusion injury and retinal detachment.

The present application also provides, inter alia, a method of treating or reducing the risk of a disorder associated with vascular leakage in a subject in need thereof, the method comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

The present application also provides, inter alia, a method of treating or reducing the risk of a disorder associated with vascular leakage in a subject in need thereof, the method comprising administering to the subject a therapeutically effective amount of at least one epoxymetabolite of a ω-3 long chain polyunsaturated fatty acid (LCPUFA), or a pharmaceutically acceptable salt thereof, and an effective amount of at least one inhibitor of a soluble epoxide hydrolase, or a pharmaceutically acceptable salt thereof. In some embodiments, the disorder is a stroke. In some embodiments, the disorder associated with vascular leakage is a stroke.

The present application also provides, inter alia, a method of treating or reducing the risk of a disorder associated with angiogenesis in a subject in need thereof, the method comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

The present application also provides, inter alia, method of treating or reducing the risk of a disorder associated with angiogenesis in a subject in need thereof, the method comprising administering to the subject a therapeutically effective amount of at least one epoxymetabolite of a ω-3 long chain polyunsaturated fatty acid (LCPUFA), or a pharmaceutically acceptable salt thereof, and an effective amount of at least one inhibitor of a soluble epoxide hydrolase, or a pharmaceutically acceptable salt thereof. In some embodiments, the disorder is cancer. In some embodiments, the disorder associated with angiogenesis is cancer.

The present application also provides, inter alia, a method of treating or reducing the risk of a disorder associated with inflammation in a subject in need thereof, the method comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

The present application also provides, inter alia, method of treating or reducing the risk of a disorder associated with inflammation in a subject in need thereof, the method comprising administering to the subject a therapeutically effective amount of at least one epoxymetabolite of a ω-3 long chain polyunsaturated fatty acid (LCPUFA), or a pharmaceutically acceptable salt thereof, and a therapeutically effective amount of at least one inhibitor of a soluble epoxide hydrolase, or a pharmaceutically acceptable salt thereof. In some embodiments, the disorder is arthritis. In some embodiments, the disorder associated with inflammation is arthritis.

The present application also provides, inter alia, a method of reducing neovascularization in a subject in need thereof, the method comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

The present application also provides, inter alia, a method of reducing neovascularization in a subject in need thereof, the method comprising administering to the subject a therapeutically effective amount of at least one epoxymetabolite of a ω-3 long chain polyunsaturated fatty acid (LCPUFA), or a pharmaceutically acceptable salt thereof, and an effective amount of at least one inhibitor of a soluble epoxide hydrolase, or a pharmaceutically acceptable salt thereof.

The present application also provides, inter alia, a method of reducing choroidal neovascularization (CNV) lesions in a subject in need thereof, the method comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

The present application also provides, inter alia, method of reducing choroidal neovascularization (CNV) lesions in a subject in need thereof, the method comprising administering to the subject a therapeutically effective amount of at least one epoxymetabolite of a ω-3 long chain polyunsaturated fatty acid (LCPUFA), or a pharmaceutically acceptable salt thereof, and an effective amount of at least one inhibitor of a soluble epoxide hydrolase, or a pharmaceutically acceptable salt thereof.

The present application also provides, inter alia, a method of reducing vascular leakage in a subject in need thereof, the method comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

The present application also provides, inter alia, method of reducing vascular leakage in a subject in need thereof, the method comprising administering to the subject a therapeutically effective amount of at least one epoxymetabolite of a ω-3 long chain polyunsaturated fatty acid (LCPUFA), or a pharmaceutically acceptable salt thereof, and an effective amount of at least one inhibitor of a soluble epoxide hydrolase, or a pharmaceutically acceptable salt thereof. In some embodiments, the vascular leakage is in a choroidal neovascularization (CNV) lesion.

The present application also provides, inter alia, a method of reducing angiogenesis in a subject in need thereof, the method comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

The present application also provides, inter alia, method of reducing angiogenesis in a subject in need thereof, the method comprising administering to the subject a therapeutically effective amount of at least one epoxymetabolite of a ω-3 long chain polyunsaturated fatty acid (LCPUFA), or a pharmaceutically acceptable salt thereof, and an effective amount of at least one inhibitor of a soluble epoxide hydrolase, or a pharmaceutically acceptable salt thereof.

The present application also provides, inter alia, a method of reducing inflammation in a subject in need thereof, the method comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

The present application also provides, inter alia, method of reducing inflammation in a subject in need thereof, the method comprising administering to the subject a therapeutically effective amount of at least one epoxymetabolite of a ω-3 long chain polyunsaturated fatty acid (LCPUFA), or a pharmaceutically acceptable salt thereof, and an effective amount of at least one inhibitor of a soluble epoxide hydrolase, or a pharmaceutically acceptable salt thereof.

In some embodiments, the epoxymetabolite of a long chain polyunsaturated fatty acid (LCPUFA) is administered by intraperitoneal injection. In some embodiments, the epoxymetabolite of a ω-3 long chain polyunsaturated fatty acid (LCPUFA), or a pharmaceutically acceptable salt thereof, is administered by intraperitoneal injection.

In some embodiments, the epoxymetabolite of a long chain polyunsaturated fatty acid (LCPUFA) is administered by local injection into or near the cornea, retina, vitreous, uvea, orbit, eyelid, conjunctiva, or iris. In some embodiments, the epoxymetabolite of a ω-3 long chain polyunsaturated fatty acid (LCPUFA), or a pharmaceutically acceptable salt thereof, is administered by local injection into or near the cornea, choroid, retina, vitreous, uvea, orbit, eyelid, conjunctiva, or iris. In some embodiments, the epoxymetabolite of a long chain polyunsaturated fatty acid (LCPUFA) is administered topically. In some embodiments, wherein the epoxymetabolite of a ω-3 long chain polyunsaturated fatty acid (LCPUFA), or a pharmaceutically acceptable salt thereof, is administered topically.

In some embodiments, the epoxymetabolite of a ω-3 long chain polyunsaturated fatty acid (LCPUFA), or a pharmaceutically acceptable salt thereof, is administered in an eye-drop formulation.

In some embodiments, the epoxymetabolite of a ω-3 long chain polyunsaturated fatty acid (LCPUFA), or a pharmaceutically acceptable salt thereof, is administered in an amount from about 1 μg/kg to about 100 μg/kg.

In some embodiments, the epoxymetabolite of a ω-3 long chain polyunsaturated fatty acid (LCPUFA), or a pharmaceutically acceptable salt thereof, is administered in an amount from about 5 μg/kg to about 50 μg/kg.

In some embodiments, the epoxymetabolite of a ω-3 long chain polyunsaturated fatty acid (LCPUFA), or a pharmaceutically acceptable salt thereof, is administered in an amount of about 50 μg/kg.

In some embodiments, the epoxymetabolite of a ω-3 long chain polyunsaturated fatty acid (LCPUFA), or a pharmaceutically acceptable salt thereof, is administered once daily.

In some embodiments, the inhibitor of a soluble epoxide hydrolase is administered orally. In some embodiments, the inhibitor of a soluble epoxide hydrolase, or a pharmaceutically acceptable salt thereof, is administered orally.

In some embodiments, the inhibitor of a soluble epoxide hydrolase, or a pharmaceutically acceptable salt thereof, is administered in an aqueous solution. In some embodiments, the inhibitor of a soluble epoxide hydrolase, or a pharmaceutically acceptable salt thereof, is administered with drinking water.

In some embodiments, the inhibitor of a soluble epoxide hydrolase, or a pharmaceutically acceptable salt thereof, is administered in an amount from about 0.1 mg/kg to about 10 mg/kg. In some embodiments, the inhibitor of a soluble epoxide hydrolase, or a pharmaceutically acceptable salt thereof, is administered in an amount of about 1 mg/kg.

In some embodiments, the epoxymetabolite of a long chain polyunsaturated fatty acid (LCPUFA) and the inhibitor of a soluble epoxide hydrolase are administered simultaneously. In some embodiments, the epoxymetabolite of a ω-3 long chain polyunsaturated fatty acid (LCPUFA), or a pharmaceutically acceptable salt thereof, and the inhibitor of a soluble epoxide hydrolase, or a pharmaceutically acceptable salt thereof, are administered simultaneously.

In some embodiments, the epoxymetabolite of a long chain polyunsaturated fatty acid (LCPUFA) and the inhibitor of a soluble epoxide hydrolase are administered consecutively. In some embodiments, the epoxymetabolite of a ω-3 long chain polyunsaturated fatty acid (LCPUFA), or a pharmaceutically acceptable salt thereof, and the inhibitor of a soluble epoxide hydrolase, or a pharmaceutically acceptable salt thereof, are administered consecutively. In some embodiments, the inhibitor of a soluble epoxide hydrolase, or a pharmaceutically acceptable salt thereof, is administered prior to administering the epoxymetabolite of a ω-3 long chain polyunsaturated fatty acid (LCPUFA), or a pharmaceutically acceptable salt thereof.

In some embodiments, the long chain polyunsaturated fatty acid (LCPUFA) is ω-3 LCPUFA.

In some embodiments, the long chain polyunsaturated fatty acid (LCPUFA) is selected from the group consisting of arachidonic acid (AA), docosahexaenoic acid (DHA), and eicosapentaenoic acid (EPA).

In some embodiments, the ω-3 long chain polyunsaturated fatty acid (LCPUFA) is selected from the group consisting of docosahexaenoic acid (DHA) and eicosapentaenoic acid (EPA).

In some embodiments, the epoxymetabolite of a long chain polyunsaturated fatty acid (LCPUFA) is selected from the group consisting of epoxyeicosatrienoic acid (EET), epoxydocosapentaenoic acid (EDP), and epoxyeicosatetraenoic acid (EEQ). In some embodiments, the epoxymetabolite of a ω-3 long chain polyunsaturated fatty acid (LCPUFA) is selected from the group consisting of epoxydocosapentaenoic acid (EDP) and epoxyeicosatetraenoic acid (EEQ), or a pharmaceutically acceptable salt thereof.

In some embodiments, the epoxymetabolite of a long chain polyunsaturated fatty acid (LCPUFA) is selected from the group consisting of 5,6-EET, 8,9-EET, 11,12-EET, 14,15-EET, 7,8-EDP, 10,11-EDP, 13,14-EDP, 16,17-EDP, 19,20-EDP, 8,9-EEQ, 11,12-EEQ, 14,15-EEQ and 17,18-EEQ. In some embodiments, the epoxymetabolite of a long chain polyunsaturated fatty acid (LCPUFA) is selected from the group consisting of 19,20-EDP, 8,9-EET, 11,12-EET, 14,15-EET and 17,18-EEQ. In some embodiments, the epoxymetabolite of a long chain polyunsaturated fatty acid (LCPUFA) is selected from the group consisting of 19,20-EDP and 17,18-EEQ.

In some embodiments, the epoxymetabolite of a ω-3 long chain polyunsaturated fatty acid (LCPUFA) is selected from the group consisting of 7,8-EDP, 10,11-EDP, 13,14-EDP, 16,17-EDP, 19,20-EDP, 8,9-EEQ, 11,12-EEQ, 14,15-EEQ and 17,18-EEQ, or a pharmaceutically acceptable salt thereof. In some embodiments, the epoxymetabolite of a ω-3 long chain polyunsaturated fatty acid (LCPUFA) is selected from the group consisting of 19,20-EDP and 17,18-EEQ, or a pharmaceutically acceptable salt thereof.

In some embodiments, the epoxymetabolite of a ω-3 long chain polyunsaturated fatty acid (LCPUFA) is 17,18-EEQ having the following structure:

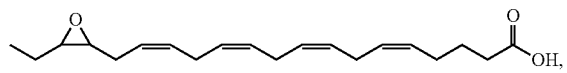

or a pharmaceutically acceptable salt thereof.

In some embodiments, the epoxymetabolite of a ω-3 long chain polyunsaturated fatty acid (LCPUFA) is 19,20-EDP having the following structure:

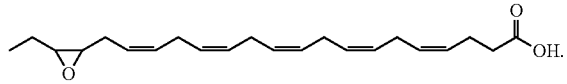 [SMILES: CCC1OC1C/C=C\C/C=C\C/C=C\C/C=C\C/C=C\CCC(=O)O]

or a pharmaceutically acceptable salt thereof.

In some embodiments, the inhibitor of a soluble epoxide hydrolase is a derivative of urea.

In some embodiments, the inhibitor of soluble epoxide hydrolase is a compound of Formula (I):

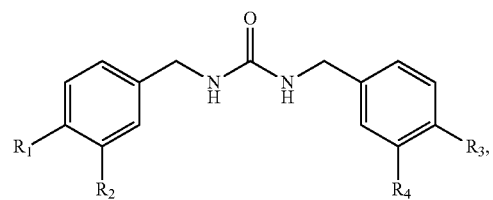

or a pharmaceutically acceptable salt thereof,
wherein $R_1$, $R_2$, $R_3$, and $R_4$ are each independently selected from H and $C_{1-3}$ alkoxy.

In some embodiments, $R_1$, $R_2$, $R_3$, and $R_4$ are each independently selected from H and methoxy.

In some embodiments, the inhibitor of soluble epoxide hydrolase is selected from any one of the compounds in the table below:

| Compound No. | $R_1$ | $R_2$ | $R_3$ | $R_4$ |
|---|---|---|---|---|
| 1 | H | H | H | H |
| BMU | OCH$_3$ | H | H | H |
| 2 | H | OCH$_3$ | H | H |
| MMU | OCH$_3$ | H | OCH$_3$ | H |
| 3 | H | OCH$_3$ | H | OCH$_3$ |

In some embodiments, the present disclosure provides a pharmaceutically acceptable salt of any one of the compounds in the above table.

In some embodiments, the inhibitor of a soluble epoxide hydrolase is selected from the group consisting of:

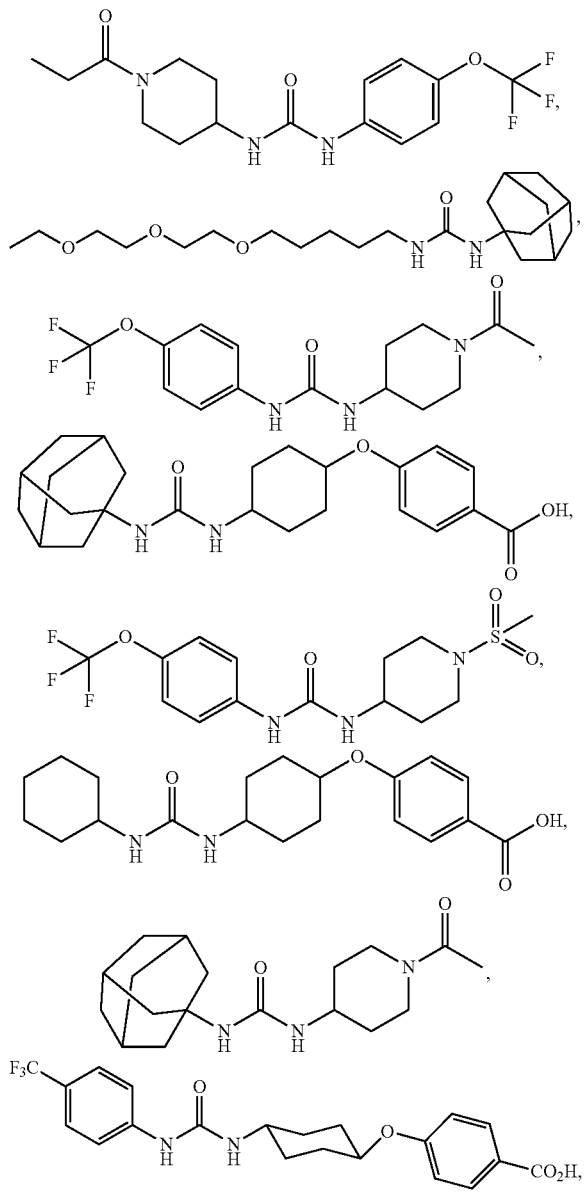

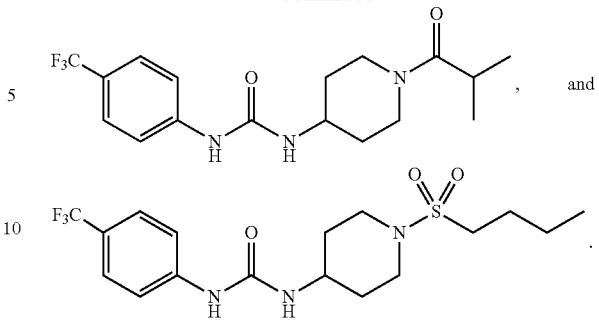

In some embodiments, the present disclosure provides a pharmaceutically acceptable salt of any one of the inhibitors of a soluble epoxide hydrolase listed above.

In some embodiments, the inhibitor of a soluble epoxide hydrolase is 1-trifluoromethoxyphenyl-3-(1-propionylpiperidin-4-yl) urea having the following structure:

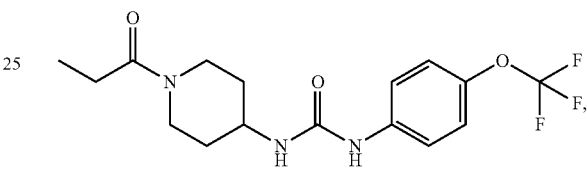

or a pharmaceutically acceptable salt thereof.

The present application also provides, inter alia, a pharmaceutical composition comprising at least one epoxymetabolite of a long chain polyunsaturated fatty acid (LCPUFA); and at least one inhibitor of a soluble epoxide hydrolase. In some embodiments, the pharmaceutical composition further comprises a pharmaceutically acceptable carrier.

The present application also provides, inter alia, a pharmaceutical composition comprising at least one epoxymetabolite of a ω-3 long chain polyunsaturated fatty acid (LCPUFA), or a pharmaceutically acceptable salt thereof; at least one inhibitor of a soluble epoxide hydrolase, or a pharmaceutically acceptable salt thereof, and a pharmaceutically acceptable carrier.

In some embodiments, the long chain polyunsaturated fatty acid (LCPUFA) is ω-3 LCPUFA.

In some embodiments, the long chain polyunsaturated fatty acid (LCPUFA) is selected from the group consisting of arachidonic acid (AA), docosahexaenoic acid (DHA), and eicosapentaenoic acid (EPA). In some embodiments, the ω-3 long chain polyunsaturated fatty acid (LCPUFA) is selected from the group consisting of docosahexaenoic acid (DHA) and eicosapentaenoic acid (EPA).

In some embodiments, the epoxymetabolite of a long chain polyunsaturated fatty acid (LCPUFA) is selected from the group consisting of epoxyeicosatrienoic acid (EET), epoxydocosapentaenoic acid (EDP), and epoxyeicosatetraenoic acid (EEQ). In some embodiments, the epoxymetabolite of a long chain polyunsaturated fatty acid (LCPUFA) is selected from the group consisting of 5,6-EET, 8,9-EET, 11,12-EET, 14,15-EET, 7,8-EDP, 10,11-EDP, 13,14-EDP, 16,17-EDP, 19,20-EDP, 8,9-EEQ, 11,12-EEQ, 14,15-EEQ and 17,18-EEQ. In some embodiments, the epoxymetabolite of a long chain polyunsaturated fatty acid (LCPUFA) is selected from the group consisting of 19,20-EDP, 8,9-EET, 11,12-EET, 14,15-EET and 17,18-EEQ. In some embodiments, the epoxymetabolite of a long chain polyunsaturated fatty acid (LCPUFA) is selected from the group consisting of 19,20-EDP and 17,18-EEQ.

In some embodiments, the epoxymetabolite of a ω-3 long chain polyunsaturated fatty acid (LCPUFA) is selected from the group consisting of epoxydocosapentaenoic acid (EDP) and epoxyeicosatetraenoic acid (EEQ), or a pharmaceutically acceptable salt thereof. In some embodiments, the epoxymetabolite of a ω-3 long chain polyunsaturated fatty acid (LCPUFA) is selected from the group consisting of 7,8-EDP, 10,11-EDP, 13,14-EDP, 16,17-EDP, 19,20-EDP, 8,9-EEQ, 11,12-EEQ, 14,15-EEQ, and 17,18-EEQ, or a pharmaceutically acceptable salt thereof. In some embodiments, the epoxymetabolite of a ω-3 long chain polyunsaturated fatty acid (LCPUFA) is selected from the group consisting of 19,20-EDP and 17,18-EEQ, or a pharmaceutically acceptable salt thereof.

In some embodiments, the epoxymetabolite of a ω-3 long chain polyunsaturated fatty acid (LCPUFA) is 17,18-EEQ having the following structure:

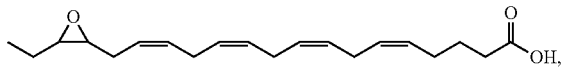

or a pharmaceutically acceptable salt thereof.

In some embodiments, the epoxymetabolite of a ω-3 long chain polyunsaturated fatty acid (LCPUFA) is 19,20-EDP having the following structure:

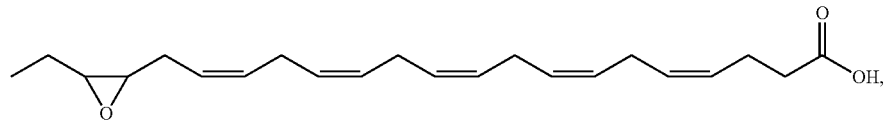 [SMILES: CCC1OC1C/C=C\C/C=C\C/C=C\C/C=C\C/C=C\CCC(=O)O]

or a pharmaceutically acceptable salt thereof.

In some embodiments, the composition comprises 19,20-EDP, or a pharmaceutically acceptable salt thereof, and 17,18-EEQ, or a pharmaceutically acceptable salt thereof.

In some embodiments, the inhibitor of a soluble epoxide hydrolase is a derivative of urea.

In some embodiments, the inhibitor of a soluble epoxide hydrolase is a compound of Formula (I):

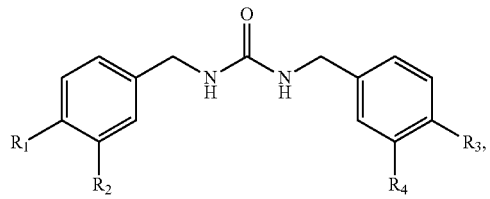

or a pharmaceutically acceptable salt thereof, wherein $R_1$, $R_2$, $R_3$, and $R_4$ are each independently selected from H and $C_{1-3}$ alkoxy.

In some embodiments, $R_1$, $R_2$, $R_3$, and $R_4$ are each independently selected from H and methoxy.

In some embodiments, the inhibitor of a soluble epoxide hydrolase is selected from any one of the compounds in the table below:

| Compound No. | $R_1$ | $R_2$ | $R_3$ | $R_4$ |
|---|---|---|---|---|
| 1 | H | H | H | H |
| BMU | OCH$_3$ | H | H | H |
| 2 | H | OCH$_3$ | H | H |
| MMU | OCH$_3$ | H | OCH$_3$ | H |
| 3 | H | OCH$_3$ | H | OCH$_3$ |

In some embodiments, the composition comprises a pharmaceutically acceptable salt of any one of the compounds in the table above.

In some embodiments, the inhibitor of soluble epoxide hydrolase is selected from the group consisting of:

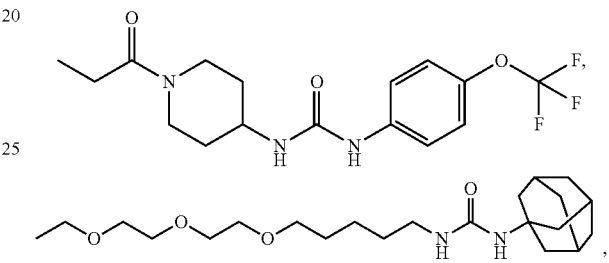

-continued

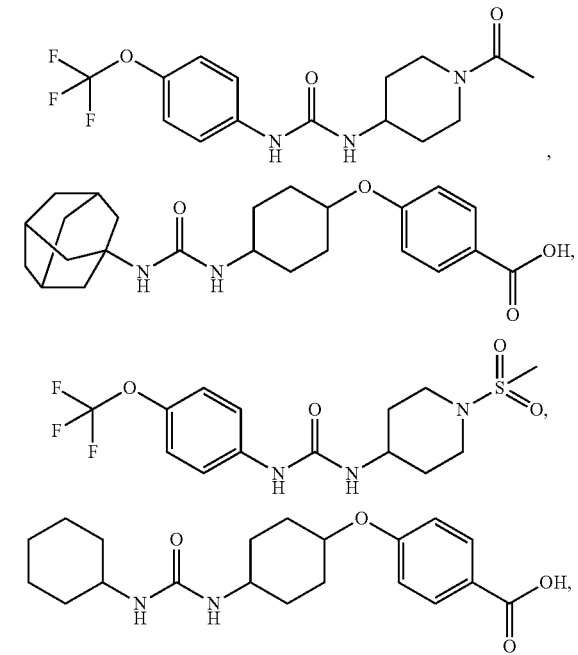

-continued

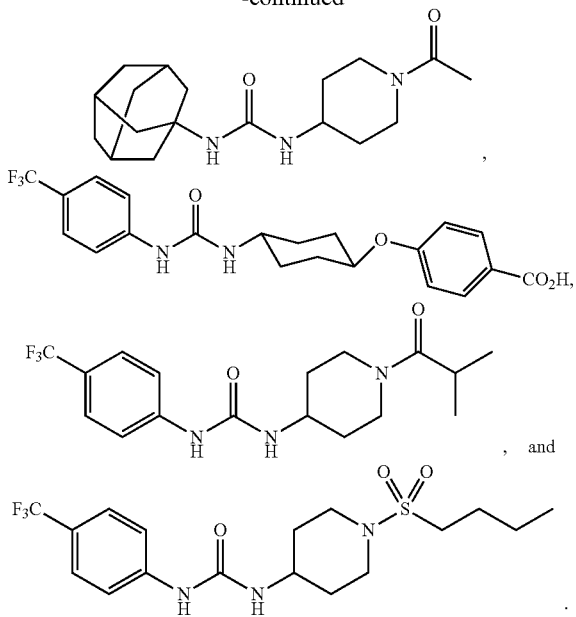

In some embodiments, the composition comprises a pharmaceutically acceptable salt of any one of the inhibitors of a soluble epoxide hydrolase listed above.

In some embodiments, the inhibitor of a soluble epoxide hydrolase is 1-trifluoromethoxyphenyl-3-(1-propionylpiperidin-4-yl) urea having the following structure:

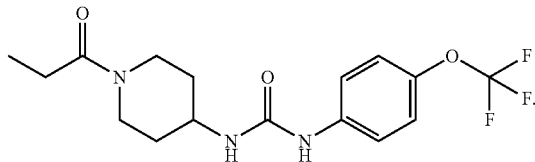 [SMILES: CCC(=O)N1CCC(NC(=O)Nc2ccc(OC(F)(F)F)cc2)CC1]

or a pharmaceutically acceptable salt thereof.

In some embodiments, the composition is a topical formulation. In some embodiments, the composition is an eye drop formulation.

In some embodiments, the amount of the epoxymetabolite of a ω-3 long chain polyunsaturated fatty acid (LCPUFA), or a pharmaceutically acceptable salt thereof, in the composition is from about 1 µg/kg to about 100 µg/kg.

In some embodiments, the amount of the epoxymetabolite of a ω-3 long chain polyunsaturated fatty acid (LCPUFA), or a pharmaceutically acceptable salt thereof, in the composition is from about 5 µg/kg to about 50 µg/kg.

In some embodiments, the amount of the epoxymetabolite of a ω-3 long chain polyunsaturated fatty acid (LCPUFA), or a pharmaceutically acceptable salt thereof, in the composition is about 50 µg/kg.

In some embodiments, the amount of the inhibitor of a soluble epoxide hydrolase, or a pharmaceutically acceptable salt thereof, in the composition is from about 0.1 mg/kg to about 10 mg/kg.

In some embodiments, the amount of the inhibitor of a soluble epoxide hydrolase, or a pharmaceutically acceptable salt thereof, in the composition is about 1 mg/kg.

In some embodiments, the composition is suitable for once daily administration.

The present application also provides, inter alia, a kit comprising:
(i) one or more purified epoxymetabolites of a long chain polyunsaturated fatty acids (LCPUFA); and
(ii) one or more purified inhibitors of a soluble epoxide hydrolase.

The present application also provides, inter alia, a kit comprising:
(i) one or more epoxymetabolites of a ω-3 long chain polyunsaturated fatty acid (LCPUFA), or a pharmaceutically acceptable salt thereof and
(ii) one or more inhibitors of a soluble epoxide hydrolase, or a pharmaceutically acceptable salt thereof.

In some embodiments, the long chain polyunsaturated fatty acid (LCPUFA) is ω-3 LCPUFA.

In some embodiments, the long chain polyunsaturated fatty acid (LCPUFA) is selected from the group consisting of arachidonic acid (AA), docosahexaenoic acid (DHA), and eicosapentaenoic acid (EPA).

In some embodiments, the ω-3 long chain polyunsaturated fatty acid (LCPUFA) is selected from the group consisting of docosahexaenoic acid (DHA) and eicosapentaenoic acid (EPA).

In some embodiments, the epoxymetabolite of a long chain polyunsaturated fatty acid (LCPUFA) is selected from the group consisting of epoxyeicosatrienoic acid (EET), epoxydocosapentaenoic acid (EDP), and epoxyeicosatetraenoic acid (EEQ).

In some embodiments, the epoxymetabolite of a ω-3 long chain polyunsaturated fatty acid (LCPUFA) is selected from the group consisting of epoxydocosapentaenoic acid (EDP) and epoxyeicosatetraenoic acid (EEQ), or a pharmaceutically acceptable salt thereof.

In some embodiments, the epoxymetabolite of a long chain polyunsaturated fatty acid (LCPUFA) is selected from the group consisting of 5,6-EET, 8,9-EET, 11,12-EET, 14,15-EET, 7,8-EDP, 10,11-EDP, 13,14-EDP, 16,17-EDP, 19,20-EDP, 8,9-EEQ, 11,12-EEQ, 14,15-EEQ and 17,18-EEQ. In some embodiments, the epoxymetabolite of a long chain polyunsaturated fatty acid (LCPUFA) is selected from the group consisting of 19,20-EDP, 8,9-EET, 11,12-EET, 14,15-EET and 17,18-EEQ. In some embodiments, the epoxymetabolite of a long chain polyunsaturated fatty acid (LCPUFA) is selected from the group consisting of 19,20-EDP and 17,18-EEQ.

In some embodiments, the epoxymetabolite of a ω-3 long chain polyunsaturated fatty acid (LCPUFA) is selected from the group consisting of 7,8-EDP, 10,11-EDP, 13,14-EDP, 16,17-EDP, 19,20-EDP, 8,9-EEQ, 11,12-EEQ, 14,15-EEQ and 17,18-EEQ, or a pharmaceutically acceptable salt thereof. In some embodiments, the epoxymetabolite of a ω-3 long chain polyunsaturated fatty acid (LCPUFA) is selected from the group consisting of 19,20-EDP and 17,18-EEQ.

In some embodiments, the inhibitor of a soluble epoxide hydrolase is a derivative of urea.

In some embodiments, the inhibitor of a soluble epoxide hydrolase is a compound of Formula (I):

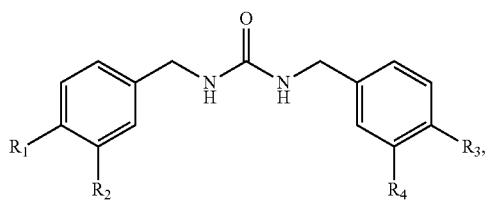

or a pharmaceutically acceptable salt thereof, wherein $R_1$, $R_2$, $R_3$, and $R_4$ are each independently selected from H and $C_{1-3}$ alkoxy.

In some embodiments, $R_1$, $R_2$, $R_3$, and $R_4$ are each independently selected from H and methoxy.

In some embodiments, the inhibitor of a soluble epoxide hydrolase is selected from any one of the compounds in the table below:

| Compound No. | $R_1$ | $R_2$ | $R_3$ | $R_4$ |
|---|---|---|---|---|
| 1 | H | H | H | H |
| BMU | $OCH_3$ | H | H | H |
| 2 | H | $OCH_3$ | H | H |
| MMU | $OCH_3$ | H | $OCH_3$ | H |
| 3 | H | $OCH_3$ | H | $OCH_3$ |

In some embodiments, the kit comprises the kit comprises a pharmaceutically acceptable salt of any one of the compounds in the table above.

In some embodiments, the inhibitor of a soluble epoxide hydrolase is selected from the group consisting of:

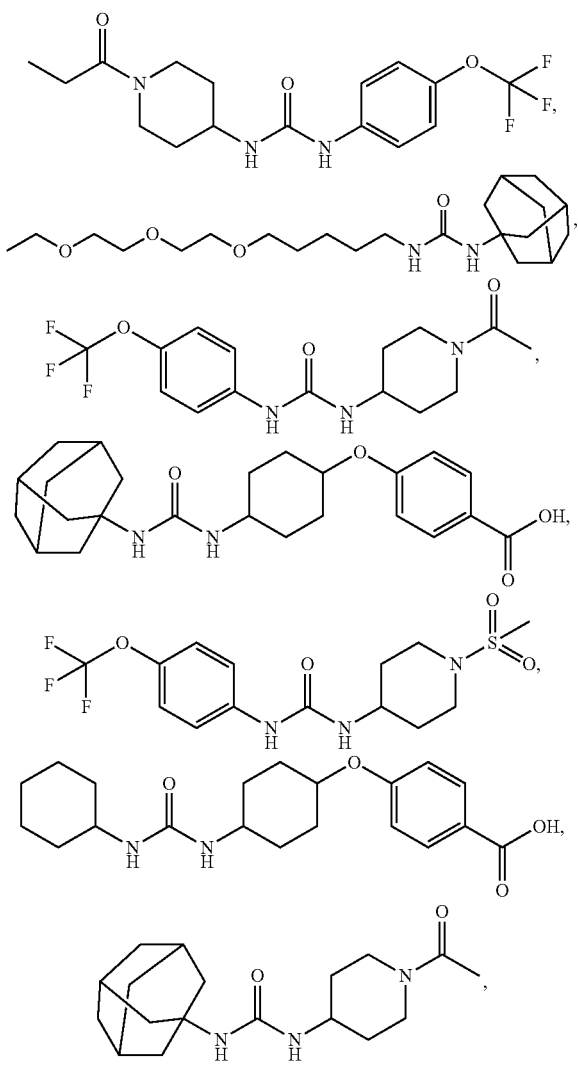

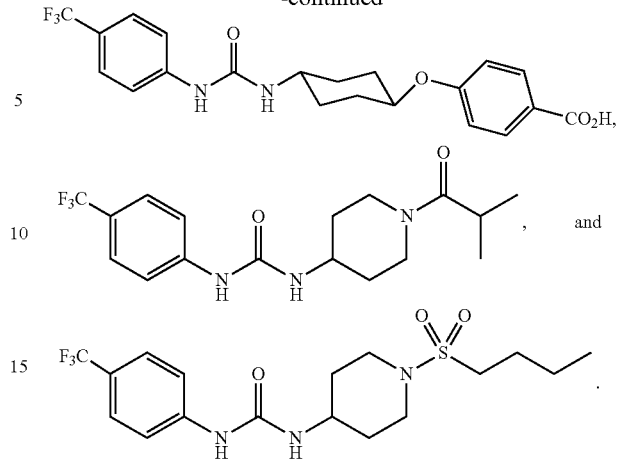

In some embodiments, the kit comprises a pharmaceutically acceptable salt of any one of the compounds listed above.

In some embodiments, the inhibitor of a soluble epoxide hydrolase is 1-trifluoromethoxyphenyl-3-(1-propionylpiperidin-4-yl) urea having the following structure:

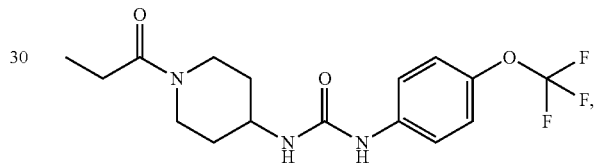

or a pharmaceutically acceptable salt thereof.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

(FIG. 1C) Fluorescein leakage in CNV lesions was graded at 7 d after CNV induction in Tie2-CYP2C8-Tg mice fed a control diet (n=25 lesions), ω-3 LCPUFAs enriched diet (n=38 lesions), or ω-6 LCPUFAs enriched diet (n=30 lesions) beginning 2 weeks before laser photocoagulation.

(FIG. 2C) Fluorescein leakage in CNV lesions was graded at 7 d after CNV induction in sEH null mice fed a control diet (n=49 lesions), ω-3 LCPUFAs enriched diet (n=57 lesions), or ω-6 LCPUFAs enriched diet (n=50 lesions) beginning 2 weeks before laser photocoagulation.

(FIG. 3C) Fluorescein leakage in CNV lesions was graded at 7 d after CNV induction in Tie2-sEH-Tg mice fed a control diet (n=21 lesions), ω-3 LCPUFAs enriched diet (n=44 lesions), or ω-6 LCPUFAs enriched diet (n=39 lesions) beginning 2 weeks before laser photocoagulation.

(FIG. 4C) Fluorescein leakage in CNV lesions was graded at 7 d after CNV induction in C57BL/6 background mice fed a control diet (n=20 lesions), ω-3 LCPUFAs enriched diet (n=26 lesions), or ω-6 LCPUFAs enriched diet (n=40 lesions) beginning 2 weeks before laser photocoagulation.

(FIGS. 5G-5I) Fluorescein leakage in CNV lesions was graded at 7 d after CNV induction in C57BL/6 mice administered 8,9-EET (FIG. 5G), 11,12-EET (FIG. 5H), and 14,15-EET (FIG. 5I).

(FIG. 7C) Fluorescein leakage in CNV lesions was graded at 7 d after CNV induction in C57BL/6 mice administered control vehicle or C21 (50 µg/kg/day) once a day immediately after laser photocoagulation.

(FIG. 9C) Representative overlay images of individual leukocytes tracked over 10 s. (FIGS. 9D-9G) Flow cytometric analysis of (FIGS. 9D, 9E) CD11b and (FIGS. 9F, 9G) CD18 expression on peripheral blood leukocytes 3 days after CNV induction in C57BL/6 mice injected i.p. with (FIGS. 9D, 9F) 17,18-EEQ (50 µg/kg/day) or (FIGS. 9E, 9G) 19,20-EDP (50 µg/kg/day). (FIGS. 9H, 9I) Real-time PCR analysis of (H) ICAM-1 and (FIG. 9I) E-selectin mRNAs in laser-captured CNV lesions at 7 days after CNV induction in C57BL/6 mice injected i.p. with EEQ (50 µg/kg/day) and EDP (50 µg/kg/day).

(FIG. 10D) Representative overlay images of individual leukocytes tracked over 10 s. (FIGS. 10E-10J) Flow cytometric analysis of (FIGS. 10E-10G) CD11b and (FIGS. 10H-10J) CD18 expression on peripheral blood leukocytes 3 days after CNV induction in mice injected i.p. with (FIGS. 10E, 10H) 8,9-EET (50 µg/kg/day), (FIGS. 10F, 10I) 11,12-EET (50 µg/kg/day), or (FIGs. G, J) 14,15-EET (50 µg/kg/day). (FIGS. 10K, 10L) Real-time PCR analysis of (FIG. 10K) ICAM-1 and (FIG. 10L) E-selectin mRNAs in laser-captured CNV lesions at 7 days after CNV induction in injected i.p. with EETs (50 µg/kg/day for each group).

(FIGS. 11C, 11D) Fluorescein leakage in CNV lesions was graded at 7 d after CNV induction in C57BL/6 mice administered control vehicle, 17,18-EEQ (50 µg/kg/day), or 19,20-EDP (50 µg/kg/day) once a day without sEH inhibitor (FIG. 11C) or with sEH inhibitor (1 mg/kg/day) (FIG. 11D).

DETAILED DESCRIPTION

Figure 1A:
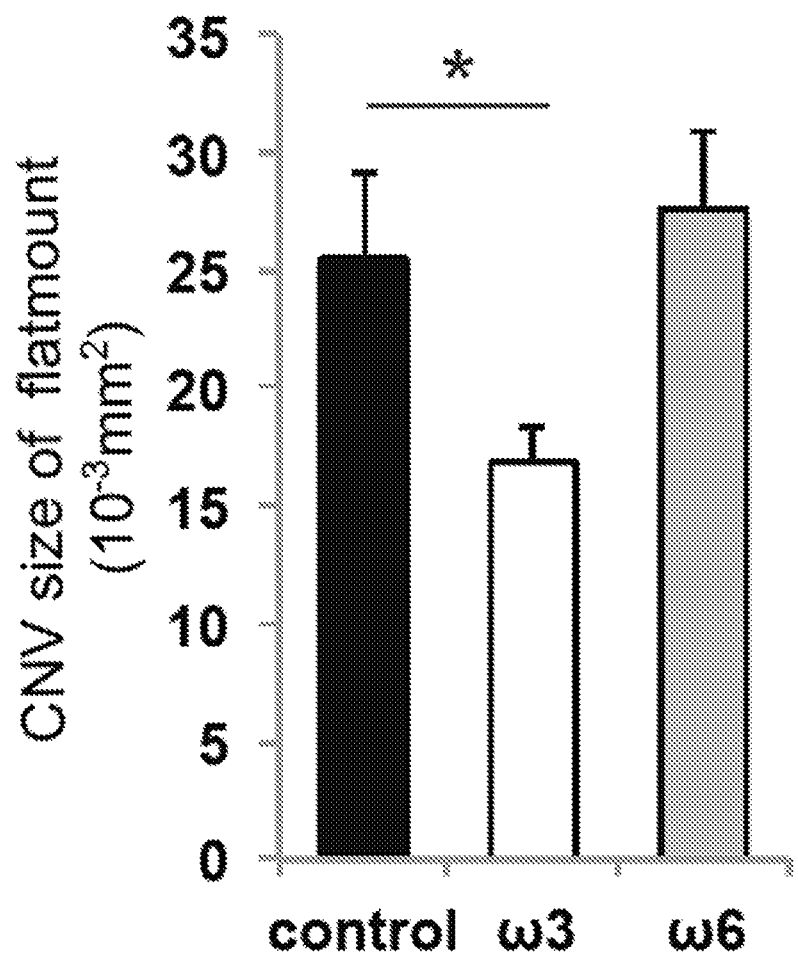
FIGS. 1A-1C. Lesion size at 7 d after choroidal neovascularization CNV induction was assessed by staining of choroidal flat-mount preparations with fluorescent isolectin B4 (FIG. 1A), and cross-sectional area of lesions was quantified by spectral domain-optical coherence tomography (SD-OCT) (demarcated by circling) (FIG. 1B), for Tie2-CYP2C8-Tg mice fed a control diet (n=25 lesions, respectively), ω-3 long chain polyunsaturated fatty acids (LCPUFAs) enriched diet (n=38 lesions, respectively), or ω-6 LCPUFAs enriched diet (n=30 lesions, respectively) beginning 2 weeks before laser photocoagulation.
Figure 1A:
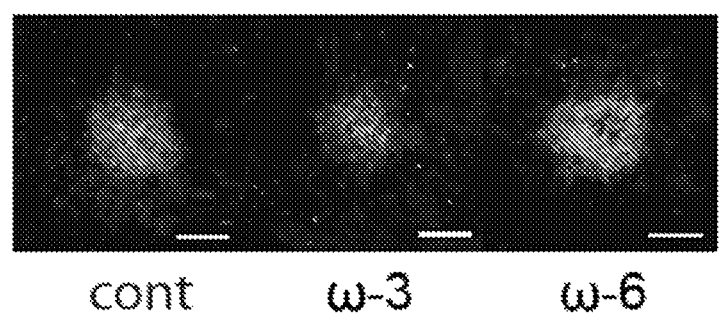

Age-related macular degeneration (AMD) is a progressive chronic disease and a leading cause of irreversible visual impairment in developed countries (1). AMD is generally classified into two forms: exudative ("wet") and nonexudative ("dry"). Advanced exudative AMD is characterized by neovascularization arising from the choroid and infiltrating the subretinal space. This choroidal neovascularization (CNV) is immature and leaky in nature, resulting in subretinal and intraretinal edema and hemorrhage that can lead to severe vision loss (2, 3). Current standard therapy for patients with CNV involves inhibiting vascular endothelial growth factor (VEGF), a molecule that promotes angiogenesis and vascular permeability (3-5). Despite their therapeutic value, intravitreal injections of anti-VEGF agents do not result in vascular regression; thus, frequent anti-VEGF injections are necessary to keep these abnormal vessels at bay (4, 5). Anti-VEGF therapy in patients has also been shown to lead to progressive vision loss with long-term use (6). Moreover, substantial vision improvement occurs in only one-third of patients treated with VEGF antagonists, and one-sixth of treated patients still progress to legal blindness (4, 5). Accordingly, there is a need for pharmacological interventions for the treatment of AMD.

Omega (ω)-3 and ω-6 fatty acids are two functionally distinct subsets of long chain polyunsaturated fatty acids (LCPUFAs) (7, 8). The metabolism of arachidonic acid (AA), docosahexaenoic acid (DHA), and eicosapentaenoic acid (EPA) into biologically active lipid mediators by cyclooxygenase (COX) and lipoxygenase (LOX) enzymes is relatively well established (10, 11). However, these LCPUFAs are also substrates for the cytochrome P450 (CYP) enzymes, which contain two main branches: ω-hydroxylases, which convert AA to hydroxyeicosatetraenoic acids (HETEs); and epoxygenases, which convert AA to epoxyeicosatrienoic acids (EETs) (12, 13). Of the three main pathways involved in eicosanoid biosynthesis (i.e., COX, LOX, and CYP), the lipid biometabolites of the CYP-branch are susceptible to changes in dietary fatty acid composition (13). The ω-3 double bond that distinguishes DHA and EPA from their ω-6 counterparts provides a preferred epoxidation site for specific CYP family members. The principal CYP metabolites derived from DHA are epoxydocosapentaenoic acids (EDPs), while those derived from EPA are epoxyeicosaquatraenoic acids (EEQs) (12). EETs, EDPs, and EEQs are potent modulators of both inflammation and vascular function (12, 13). These fatty acid metabolites are produced primarily in the endothelium by CYP2C and CYP2J monooxygenase families and are further metabolized by soluble epoxide hydrolase (sEH) into less active dihydroxyeicosatrienoic acids (DHETs), dihydroxydocosapentaenoic acids (DHDPs), and dihydroxyeicosaquatraenoic acids (DHEQs) (derived from AA, DHA, and EPA, respectively), thereby conferring regulation of these bioactive lipid metabolites (12-14).

Definitions

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the term "reducing risk" of a disease, condition or disorder refers to decreasing the risk of occurrence of the disease, condition or disorder in a subject or group of subjects (e.g., a subject or group of subjects predisposed to or susceptible to the disease, condition or disorder). In some embodiments, reducing the risk of a disease, condition or disorder refers to decreasing the possibility of acquiring the disease, condition or disorder and/or its associated symptoms. In some embodiments, reducing the risk of a disease, condition or disorder refers to completely or almost completely stopping the disease, condition or disorder from occurring.

As used herein, the term "purified" refers to a compound or a composition that comprises the desired component or components and that is substantially free from undesirable elements (e.g., contaminants and/or impurities). In some embodiments, a purified compound or composition comprises at least 70-90%, 90-95%, or 95-99% (w/w) or more of the desired component or components.

As used herein, the term "pharmaceutical carrier", or "pharmaceutically acceptable carrier" refers to a pharmaceutically acceptable solvent, suspending agent or vehicle for delivering the compound of the present application to the subject. The carrier may be liquid or solid and is selected with the planned manner of administration in mind. Each carrier must be pharmaceutically "acceptable" in the sense of being compatible with other ingredients of the composition and non-injurious to the subject.

Abbreviations and Acronyms

The following abbreviations may be used in the present disclosure: Spectral domain-optical coherence tomography (SD-OCT); soluble epoxide hydrolase (sEH); inhibitor of soluble epoxide hydrolase (sEHI); Human soluble epoxide hydrolase (hsEH); long chain polyunsaturated fatty acid (LCPUFA); choroidal neovascularization (CNV); age-related macular degeneration (AMD); retinopathy of prematurity (ROP); arachidonic acid (AA); docosahexaenoic acid (DHA); eicosapentaenoic acid (EPA); epoxyeicosatrienoic acid (EET); epoxydocosapentaenoic acid (EDP); epoxyeicosatetraenoic acid (EEQ); Cytochrome P (CYP); liquid chromatography (LC); mass spectrometry (MS); Intercellular Adhesion Molecule (ICAM); by intraperitoneal injection (i.p.); peripheral blood leukocyte (PBL); polymerase chain reaction (PCR); ribonucleic acid (RNA); standard error of the mean (SEM); mean fluorescence intensity (MFI); area under the curve (AUC); vascular endothelial growth factor (VEGF); lipoxygenase (LOX); cyclooxygenase (COX); hydroxyeicosatetraenoic acid (HETE); dihydroxyeicosatrienoic acid (DHET); dihydroxydocosapentaenoic acid (DHDP); dihydroxyeicosaquatraenoic acid (DHEQ); acute myeloid leukemia (AML); chronic myeloid leukemia (CML); acute lymphoblastic leukemia (ALL); hexadecatrienoic acid (HTA); α-linolenic acid (ALA); stearidonic acid (SDA); eicosatrienoic acid (ETE); heneicosapentaenoic acid (HPA); docosapentaenoic acid (DPA); linoleic acid (LA); gamma-linolenic acid (GLA); dihomo-gamma-linolenic acid (DGLA); dimethyl sulfoxide (DMSO); dimethylformamide (DMF); polyethyleneglycol (PEG); fluorescence-activated cell sorting (FACS); capture microdissection (LCM); High Performance Liquid Chromatography (HPLC); Bovine serum albumin (BSA); Ethylenediaminetetraacetic acid (EDTA); 12-[(adamantan-1-ylcarbamoyl)amino]dodecanoic acid (AUDA); 1-trifluoromethoxyphenyl-3-(1-propionylpiperidin-4-yl) urea (TPPU); 1-adamantanyl-3-{5-[2-(2-ethoxyethoxy)ethoxy]pentyl]}urea (AEPU); 1-(1-acetylpiperidin-4-yl)-3-(adamantan-1-yl)urea (APAU); 1-(1-(methylsulfonyl)piperidin-4-yl)-3-(4-(trifluoromethoxy)phenyl)urea (TUPS); 1-(1-(cyclopropanecarbonyl)piperidin-4-yl)-3-(4-(trifluoromethoxy)phenyl)urea (TPCU); 1-(1-acetylpiperidin-4-yl)-3-(4-(trifluoromethoxy)phenyl)urea (TPAU); retinal pigment epithelium (RPE); late leakage of undetermined source (LLUS); cytochrome P450 isoform 2C8 (CYP2C8); transgenic mice (Tg); tyrosine kinase with immunoglobulin-like and EGF-like domains (Tie2); epidermal growth factor (EGF); C57 black 6 standard breed mouse line (that serve as control mice) derived from a colony at the Jackson Laboratories (C57Bl/6J); phosphate-buffered saline (PBS); cyano (6-methoxynaphthalen-2-yl)methyl trans-[(3-phenyloxiran-2-yl)methyl] carbonate (CMNPC).

Methods of the Present Application

Methods of Treating a Disease or Condition

In some embodiments, the present application is directed to methods of treating or reducing the risk of a disorder associated with a neovascularization in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

In some embodiments, the neovascularization is corneal, retinal, choroidal, uveal, or iris neovascularization. In some embodiments, the neovascularization is choroidal neovascularization (CNV). In some embodiments, disorder is an ophthalmological disorder associated with neovascularization. In some embodiments, the ophthalmological disorder associated with neovascularization is age-related macular degeneration (AMD), Stargardt's disease, retinopathy, retinopathy of prematurity (ROP), diabetic retinopathy, retinal vein occlusion, sickle cell retinopathy, radiation retinopathy, iritis, or conjunctivitis.

In some embodiments, the ophthalmological disorder associated with neovascularization is age-related macular degeneration (AMD). Age-related macular degeneration (AMD) is a leading cause of blindness. Advanced exudative AMD is defined by the formation of abnormal blood vessels that grow from the choroidal vasculature, through breaks in Bruch's membrane, toward the outer retina. Less commonly, the abnormal vessels originate from retinal vasculature. These blood vessels are immature and leaky, resulting in subretinal and intraretinal edema and hemorrhage, which leads to vision loss. Neovascular AMD accounts for 10-15% of AMD cases, and if left untreated, can rapidly lead to substantial vision loss.

In some embodiments, the age-related macular degeneration (AMD) is atrophic. In some embodiments, the age-related macular degeneration (AMD) is neovascular. In some embodiments, the age-related macular degeneration (AMD) is exudative ("wet"). In some embodiments, the age-related macular degeneration (AMD) is nonexudative ("dry").

In some embodiments, the ophthalmological disorder is loss of vision (e.g., rapid and/or substantial). In some embodiments, the ophthalmological disorder is irreversible vision loss (e.g., in the elderly). In some embodiments, the ophthalmological disorder is neovascular and inflammatory ocular disease.

In some embodiments, the present application is directed to methods of treating or reducing the risk of a disorder associated with angiogenesis in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

In some embodiments, the disorder associated with angiogenesis is cancer. In some embodiments, the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. In some embodiments, the cancer is located in an organ or tissue that is not highly vascularized. In some embodiments, cancer is selected from the group selected from sarcoma, angiosarcoma, fibrosarcoma, rhabdomyosarcoma, liposarcoma, myxoma, rhabdomyoma, fibroma, lipoma, teratoma, lung cancer, bronchogenic carcinoma squamous cell, undifferentiated small cell, undifferentiated large cell, adenocarcinoma, alveolar bronchiolar carcinoma, bronchial adenoma, sarcoma, lymphoma, chondromatous hamartoma, mesothelioma, gastrointestinal cancer, cancer of the esophagus, squamous cell carcinoma, adenocarcinoma, leiomyosarcoma, lymphoma, cancer of the stomach, carcinoma, lymphoma, leiomyosarcoma, cancer of the pancreas, ductal adenocarcinoma, insulinoma, glucagonoma, gastrinoma, carcinoid tumor, vipoma, cancer of the small bowel, adenocarcinoma, lymphoma, carcinoid tumors, Kaposi's sarcoma, leiomyoma, hemangioma, lipoma, neurofibroma, fibroma, cancer of the large bowel or colon, tubular adenoma, villous adenoma, hamartoma, leiomyoma, genitourinary tract cancer, cancer of the kidney adenocarcinoma, Wilm's tumor (nephroblastoma), lymphoma, leukemia, cancer of the bladder, cancer of the urethra, squamous cell carcinoma, transitional cell carcinoma, cancer of the prostate, cancer of the testis, seminoma, teratoma, embryonal carcinoma, teratocarcinoma, choriocarcinoma, sarcoma, interstitial cell carcinoma, fibroma, fibroadenoma, adenomatoid tumors, lipoma, liver cancer, hepatoma hepatocellular carcinoma, cholangiocarcinoma, hepatoblastoma, angiosarcoma, hepatocellular adenoma, hemangioma, bone cancer, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor, chordoma, osteochrondroma (osteocartilaginous exostoses), benign chondroma, chondroblastoma, chondromyxofibroma, osteoid osteoma giant cell tumor, nervous system cancer, cancer of the skull, osteoma, hemangioma, granuloma, xanthoma, osteitis deformans, cancer of the meninges meningioma, meningiosarcoma, gliomatosis, cancer of the brain, astrocytoma, medulloblastoma, glioma, ependymoma, germinoma (pinealoma), glioblastoma multiforme, oligodendroglioma, schwannoma, retinoblastoma, congenital tumors, cancer of the spinal cord, neurofibroma, meningioma, glioma, sarcoma, gynecological cancer, cancer of the uterus, endometrial carcinoma, cancer of the cervix, cervical carcinoma, pre tumor cervical dysplasia, cancer of the ovaries, ovarian carcinoma, serous cystadenocarcinoma, mucinous cystadenocarcinoma, unclassified carcinoma, granulosa-theca cell tumor, Sertoli Leydig cell tumor, dysgerminoma, malignant teratoma, cancer of the vulva, squamous cell carcinoma, intraepithelial carcinoma, adenocarcinoma, fibrosarcoma, melanoma, cancer of the vagina, clear cell carcinoma, squamous cell carcinoma, botryoid sarcoma, embryonal rhabdomyosarcoma, cancer of the fallopian tubes, hematologic cancer, cancer of the blood, acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, myelodysplastic syndrome, Hodgkin's lymphoma, non-Hodgkin's lymphoma (malignant lymphoma), Waldenstrom's macroglobulinemia, skin cancer, malignant melanoma, basal cell carcinoma, squamous cell carcinoma, Kaposi's sarcoma, moles dysplastic nevi, lipoma, angioma, dermatofibroma, keloids, psoriasis, adrenal gland cancer, and neuroblastoma. In some embodiments, the cancer is a cancer of the eye, e.g., eyelid tumors, e.g., malignant eye lid tumors, benign eye lid tumors. In some embodiments, the cancer is localized in or near a non-vascularized tissue.

In some embodiments, the present application is directed to methods of treating or reducing the risk of a disorder associated with inflammation in a subject in need thereof, the method comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase. In some embodiments, the disorder associated with inflammation is arthritis. In some embodiments, the disorder associated with inflammation is atherosclerosis. In some embodiments, the disorder associated with inflammation is selected from dry eye disease, glaucoma, uveitis, retinal degeneration, dry age-related macular degeneration (AMD), retinopathy of prematurity, diabetic retinopathy, optic neuropathy, ischemia reperfusion injury and retinal detachment. In some embodiments, the present application is directed to methods of treating or reducing the risk of inflammation in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

In some embodiments, the present application is directed to a methods of treating or reducing the risk of a disorder associated with vascular leakage in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase. In some embodiments, the disorder associated with vascular leakage is a stroke. In some embodiments, the disorder associated with vascular leakage is selected from dry eye disease, glaucoma, uveitis, retinal degeneration, dry age-related macular degeneration (AMD), retinopathy of prematurity, diabetic retinopathy, optic neuropathy, ischemia reperfusion injury and retinal detachment.

Methods of Inhibiting/Reducing the Effect of a Pathological Process

In some embodiments, the present application is directed to methods of reducing neovascularization in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase. In some embodiments, neovascularization is inflammatory (e.g., corneal inflammatory neovascularization). In some embodiments, neovascularization is stimulated by pro-angiogenic factors (e.g., Vascular Endothelial Growth Factor and Fibroblast Growth Factor). In some embodiments, neovascularization is stimulated by anti-angiogenic factors (e.g, pigment epithelium-derived growth factor). In some embodiments, neovascularization is laser-induced (e.g., laser-induced choroidal neovascularization). In some embodiments, the neovascularization is ocular neovascularization (e.g., neovascularization is the excessive ingrowth of blood vessels in the eye). In some embodiments, the neovascularization is corneal, retinal, choroidal, uveal, or iris neovascularization. In one example, the present methods reduce formation of a microvasculature within the innermost layer of the choroid of the eye.

In some embodiments, the present application is directed to methods of reducing choroidal neovascularization (CNV) lesions in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase. In some embodiments, the CNV lesion is angiogenic. In some embodiments, the CNV lesion is inflammatory. In some embodiments, the CNV lesion is angiogenic and inflammatory. In some embodiments, CNV lesion is age related. In some embodiments, CNV lesion demonstrates irregular, indistinct, late, subretinal retinal pigment epithelium (RPE) leakage or late leakage of undetermined source (LLUS). The present methods for reducing choroidal neovascularization (CNV) lesions are advantageous because the choroidal neovascularization (CNV) is immature and leaky in nature, resulting in subretinal and intraretinal edema and hemorrhage that can lead to severe vision loss.

In some embodiments, the present application is directed to methods of reducing vascular leakage in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase. In some embodiments, the vascular leakage is in choroidal neovascularization (CNV) lesions (e.g., angiogenic and/or inflammatory CNV lesions).

In some embodiments, the present application is directed to methods of reducing angiogenesis in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

In some embodiments, the present application is directed to methods of reducing inflammation in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

In some embodiments, the present application is directed to methods of reducing abnormal blood vessel growth in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

In some embodiments, the present application is directed to methods of resolving pathologic neovessels in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

In some embodiments, the present application is directed to methods of promoting vascular regression in a subject in need thereof, the methods comprising administering to the subject a therapeutically effective amount of at least one epoxymetabolite of a long chain polyunsaturated fatty acid (LCPUFA) and a therapeutically effective amount of at least one inhibitor of a soluble epoxide hydrolase.

Long Chain Polyunsaturated Fatty Acid (LCPUFA) and their Metabolites

The ω-3 and ω-6 LCPUFAs are two classes of dietary lipids that are highly enriched in the retina and are thought to have opposing physiological effects. The ω-3 LCPUFAs have anti-thrombotic and anti-inflammatory properties, and compete with ω-6 LCPUFAs for downstream eicosanoids synthesis at the CYP, cyclooxygenase, and lipoxygenase levels. Mammals depend on dietary intake of LCPUFAs because they lack the enzymes that synthesize these molecules de novo. The ω-6 LCPUFAs are the primary polyunsaturated fatty acids found in western diets. Dietary enrichment with ω-3 LCPUFAs has been shown to be protective against pathological angiogenesis, which occurs in cancer and retinopathies. Prospective clinical studies have suggested that dietary ω-3 LCPUFAs may protect against AMD. In a prospective cohort study of 1837 participants at moderate-to-high risk of developing advanced AMD, those who reported the highest intake of ω-3 LCPUFAs (median of 0.11% of total energy intake) were 30% less likely than their peers to develop the condition over a 12-year period.

In some embodiments, the long chain polyunsaturated fatty acid (LCPUFA) is selected from the group consisting of arachidonic acid (AA), docosahexaenoic acid (DHA), and eicosapentaenoic acid (EPA).

ω-6 Long Chain Polyunsaturated Fatty Acids

In some embodiments, the long chain polyunsaturated fatty acid (LCPUFA) is ω-6 LCPUFA. In some embodiments, the ω-6 LCPUFA is a constituent of a dietary source (e.g., poultry, eggs, nuts, cereals, durum wheat, whole-grain breads, most vegetable oils, grape seed oil, evening primrose oil, borage oil, blackcurrant seed oil, flax/linseed oil, rapeseed or canola oil, hemp oil, soybean oil, cottonseed oil, sunflower seed oil, corn oil, safflower oil, pumpkin seeds, acai berry, cashews, pecans, pine nuts, walnuts or *spirulina*).

In some embodiments, the ω-6 LCPUFA is selected from the group consisting of linoleic acid (LA; 18:2 ω6), gamma-linolenic acid (GLA; 18:3 ω6), calendic acid (18:3 ω6), eicosadienoic acid (20:2 ω6), dihomo-gamma-linolenic acid (DGLA; 20:3 ω6), arachidonic acid (AA; 20:4 ω6), docosadienoic acid (22:2 ω6), adrenic acid (22:4 ω6), docosapentaenoic acid (DPA, osbond acid, 22:5 ω6), tetracosatetraenoic acid (24:4 ω6), and tetracosapentaenoic acid (24:5 ω6). In some embodiments, the ω-6 LCPUFA is selected from the group consisting of all-cis-9,12-octadecadienoic acid, all-cis-6,9,12-octadecatrienoic acid, 8E,10E,12Z-octadecatrienoic acid, all-cis-11,14-eicosadienoic acid, all-cis-8,11,14-eicosatrienoic acid, all-cis-5,8,11,14-eicosatetraenoic acid, all-cis-13,16-docosadienoic acid, all-cis-7,10,13,16-docosatetraenoic acid, all-cis-4,7,10,13,16-docosapentaenoic acid, all-cis-9,12,15,18-tetracosatetraenoic acid, and all-cis-6,9,12,15,18-tetracosapentaenoic acid. In some embodiments, the ω-6 LCPUFA is arachidonic acid (AA).

ω-3 Long Chain Polyunsaturated Fatty Acids

In some embodiments, the long chain polyunsaturated fatty acid (LCPUFA) is ω-3 LCPUFA. In some embodiments, the ω-3 LCPUFA is a constituent of a dietary source (e.g., plant source such as kiwi fruit seed oil, *perilla*, chia seed, flax, lingonberry, fig seed oil, camelina, purslane, black raspberry, hemp, canola; or other sources such as fish, fish oil, eggs and meat).

In some embodiments, the ω-3 LCPUFA is selected from the group consisting of hexadecatrienoic acid (HTA; 16:3 ω3), α-linolenic acid (ALA; 18:3 ω3); stearidonic acid (SDA; 18:4 ω3), eicosatrienoic acid (ETE; 20:3 ω3), eicosatetraenoic acid (ETA; 20:4 ω3), eicosapentaenoic acid (EPA; 20:5 ω3), heneicosapentaenoic acid (HPA; 21:5 ω3), docosapentaenoic acid (DPA; clupanodonic acid; 22:5 ω3), docosahexaenoic acid (DHA; 22:6 ω3), tetracosapentaenoic acid (24:5 ω3), tetracosahexaenoic acid (nisinic acid; 24:6 ω3). In some embodiments, the ω-3 LCPUFA is selected from the group consisting of all-cis-7,10,13-hexadecatrienoic acid (HTA), all-cis-9,12,15-octadecatrienoic acid (ALA), all-cis-6,9,12,15-octadecatetraenoic acid (SDA), all-cis-11,14,17-eicosatrienoic acid (ETE), all-cis-8,11,14,17-eicosatetraenoic acid (ETA), all-cis-5,8,11,14,17-eicosapentaenoic acid (EPA), all-cis-6,9,12,15,18-heneicosapentaenoic acid (HPA), all-cis-7,10,13,16,19-docosapentaenoic acid (DPA), all-cis-4,7,10,13,16,19-docosahexaenoic acid (DHA), all-cis-9,12,15,18,21-tetracosapentaenoic acid, and all-cis-6,9,12,15,18,21-tetracosahexaenoic acid.

In some embodiments, the ω-3 LCPUFA is selected from the group consisting of ALA, EPA, ω3-DPA and DHA. In some embodiments, the ω-3 LCPUFA is selected from the group consisting of EPA and DHA Epoxymetabolites of a ω-6 LCPUFAs In some embodiments, the epoxymetabolite of a long chain polyunsaturated fatty acid (LCPUFA) is derived from a ω-6 LCPUFA (e.g., any one of ω-6 LCPUFAs described herein). In some embodiments, the epoxymetabolite of a ω-6 long chain polyunsaturated fatty acid (LCPUFA) is derived from AA. In some embodiments, the AA-derived epoxymetabolite is an epoxyeicosatrienoic acid (EET). In some embodiments, the AA-derived epoxymetabolite is selected from the group consisting of:

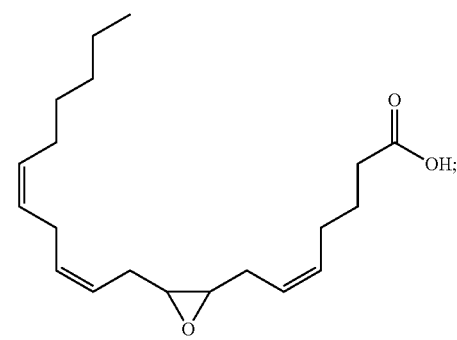

(8,9-EET)

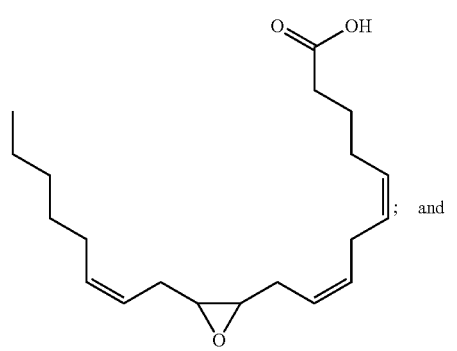

(11,12-EET); and

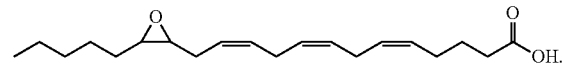

(14,15-EET)

In some embodiments, the epoxymetabolite of a long chain polyunsaturated fatty acid (LCPUFA) is selected from the group consisting of (+)5,6-EET, (+)8,9-EET, (+)11,12-EET and (+)14,15-EET. In some embodiments, the epoxymetabolite of a long chain polyunsaturated fatty acid (LCPUFA) is selected from the group consisting of (−)5,6-EET, (−)8,9-EET, (−)11,12-EET and (−)14,15-EET.

Epoxymetabolites of a ω-3 LCPUFAs

In some embodiments, the epoxymetabolite of a long chain polyunsaturated fatty acid (LCPUFA) is derived from a ω-3 LCPUFA (e.g., any one of ω-3 LCPUFAs described herein). In some embodiments, the epoxymetabolite of a ω-3 long chain polyunsaturated fatty acid (LCPUFA) is derived from EPA or DHA. In some embodiments, the EPA-derived epoxymetabolite is an epoxyeicosatetraenoic acid (EEQ). In some embodiments, the DHA-derived epoxymetabolite is an epoxydocosapentaenoic acid (EDP). In some embodiments, the epoxymetabolite of a ω-3 long chain polyunsaturated fatty acid (LCPUFA) is selected from any one of epoxymetabolites listed in Table A.

TABLE A

Cytochrome P450 (CYP) Derived Epoxymetabolites of Docosahexaenoic acid (DHA) and Eicosapentaenoic acid (EPA)

| Analogs of | Derived from | Name |
|---|---|---|
| epoxydocosapentaenoic acid (EDP) | Docosahexaenoic acid (DHA) | 4,5-EDP |
|  |  | 7,8-EDP |
|  |  | 10,11-EDP |
|  |  | 13,14-EDP |
|  |  | 16,17-EDP |
|  |  | 19,20-EDP |
| epoxyeicosaquatraenoic acid (EEQ) | Eicosapentaenoic acid (EPA) | 5,6-EEQ |
|  |  | 8,9-EEQ |
|  |  | 11,12-EEQ |
|  |  | 14,15-EEQ |
|  |  | 17,18-EEQ |

In some embodiments, the EPA-derived epoxymetabolite is selected from the group consisting of:

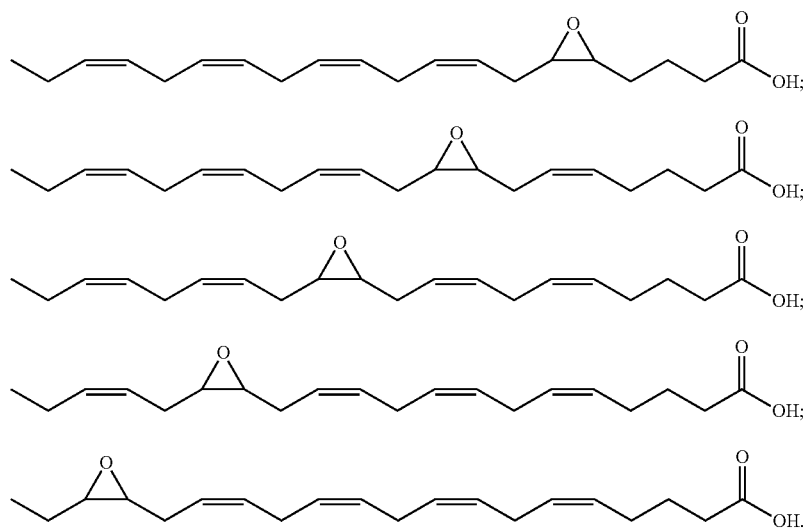

(5,6-EEQ)
(8,9-EEQ)
(11,12-EEQ)
(14,15-EEQ); and
(17,18-EEQ)

In some embodiments, the EPA-derived epoxymetabolite is selected from the group consisting of (+)5,6-EEQ, (+)8,9-EEQ, (+)11,12-EEQ, (+)14,15-EEQ and (+)17,18-EEQ. In some embodiments, the EPA-derived epoxymetabolite is selected from the group consisting of (−)5,6-EEQ, (−)8,9-EEQ, (−)11,12-EEQ, (−)14,15-EEQ and (−)17,18-EEQ.

In some embodiments, the DHA-derived epoxymetabolite is selected from the group consisting of:

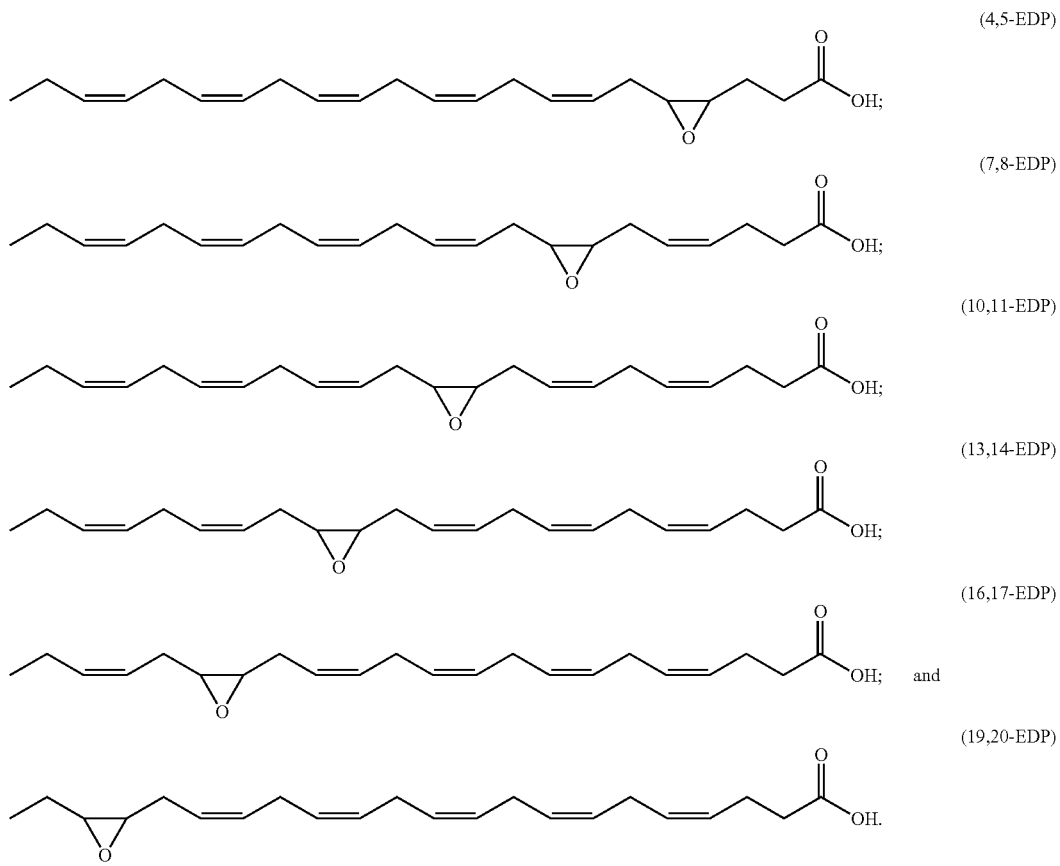

(4,5-EDP)
(7,8-EDP)
(10,11-EDP)
(13,14-EDP)
(16,17-EDP); and
(19,20-EDP)

In some embodiments, the DHA-derived epoxymetabolite is selected from the group consisting of (+)4,5-EDP, (+)7,8-EDP, (+)10,11-EDP, (+)13,14-EDP, (+)16,17-EDP and (+)19,20-EDP. In some embodiments, the DHA-derived epoxymetabolite is selected from the group consisting of (−)4,5-EDP, (−)7,8-EDP, (−)10,11-EDP, (−)13,14-EDP, (−)16,17-EDP and (−)19,20-EDP.

In some embodiments, the epoxymetabolite of a long chain polyunsaturated fatty acid (LCPUFA) is selected from any one of epoxymetabolites disclosed, for example, in PCT application No. PCT/US2014/010880 (published as WO2014110261), or US patent publication No. US 2015/0335603, which are incorporated herein by reference in their entirety.

In some embodiments, the epoxymetabolite of a long chain polyunsaturated fatty acid (LCPUFA) is selected from any one of epoxymetabolites disclosed, for example, in Yanai R, et al. (2014) Cytochrome P450-generated metabolites derived from omega-3 fatty acids attenuate neovascularization. *Proc Natl Acad Sci USA* 111(26):9603-9608, which is incorporated herein by reference in its entirety.

In some embodiments, the epoxymetabolite of a long chain polyunsaturated fatty acid (LCPUFA) is selected from the group consisting of epoxyeicosatrienoic acid (EET), epoxydocosapentaenoic acid (EDP), and epoxyeicosatetraenoic acid (EEQ).

In some embodiments, the epoxymetabolite of a long chain polyunsaturated fatty acid (LCPUFA) is selected from the group consisting of 5,6-EET, 8,9-EET, 11,12-EET, 14,15-EET, 7,8-EDP, 10,11-EDP, 13,14-EDP, 16,17-EDP, 19,20-EDP, 8,9-EEQ, 11,12-EEQ, 14,15-EEQ and 17,18-EEQ. In some embodiments, the epoxymetabolite of a long chain polyunsaturated fatty acid (LCPUFA) is selected from the group consisting of 19,20-EDP and 17,18-EEQ.

Inhibitors of a Soluble Epoxide Hydrolase

Soluble epoxide hydrolase (sEH) is a member of the epoxide hydrolase family of enzymes. This enzyme binds to specific epoxides and converts these molecules to the corresponding diols. sEH is expressed in numerous tissues including liver, vascular endothelium, leukocytes, red blood cells, smooth muscle cells, adipocytes and the kidney proximal tubule. Epoxymetabolites of long chain polyunsaturated fatty acids (such as those derived from AA, DHA, and EPA) are hydrolyzed by soluble epoxide hydrolase (sEH) into less active dihydroxyeicosatrienoic acids (DHETs), dihydroxydocosapentaenoic acids (DHDPs), and dihydroxyeicosaquatraenoic acids (DHEQs), respectively, thereby conferring regulation of these bioactive lipid metabolites.

The methods presented herein advantageously achieve increased half-life and bioavailability of the epoxymetabolites of long chain polyunsaturated fatty acids by inhibiting sEH using inhibitors of the sEH enzyme.

In some embodiments, the inhibitor of a soluble epoxide hydrolase is a derivative of urea. In some embodiments, the inhibitor of a soluble epoxide hydrolase is found in plants. For example, the inhibitor of a soluble epoxide hydrolase may be found in Brassicales order of flowering plants (e.g., akaniaceae, bataceae, brassicaceae, capparaceae, caricaceae, cleomaceae, gyrostemonaceae, koeberliniaceae, limnanthaceae, moringaceae, pentadiplandraceae, resedaceae, salvadoraceae, setchellanthaceae, tovariaceae or tropaeolaceae family of the Brassicales order).

In some embodiments, the inhibitor of a soluble epoxide hydrolase is a compound of Formula (I):

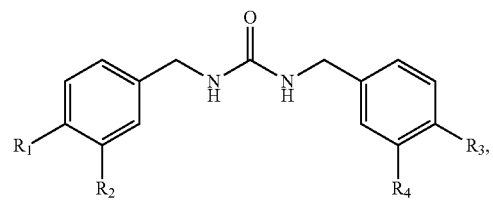

or a pharmaceutically acceptable salt thereof, wherein $R_1$, $R_2$, $R_3$, and $R_4$ are each independently selected from H and $C_{1-3}$ alkoxy. In some embodiments, $R_1$, $R_2$, $R_3$, and $R_4$ are each independently selected from H and methoxy.

In some embodiments, the inhibitor of a soluble epoxide hydrolase is selected from any one of the compounds in the table below:

| Compound No. | $R_1$ | $R_2$ | $R_3$ | $R_4$ |
|---|---|---|---|---|
| 1 | H | H | H | H |
| BMU | $OCH_3$ | H | H | H |
| 2 | H | $OCH_3$ | H | H |
| MMU | $OCH_3$ | H | $OCH_3$ | H |
| 3 | H | $OCH_3$ | H | $OCH_3$ |

In some embodiments, the inhibitor of a soluble epoxide hydrolase is selected from the group consisting of:

(TPPU, 1770)

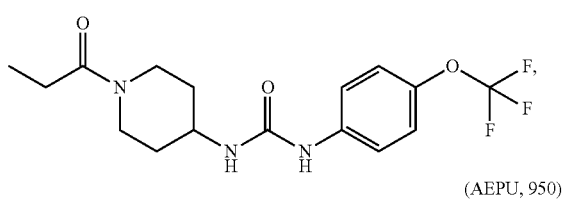

(AEPU, 950)

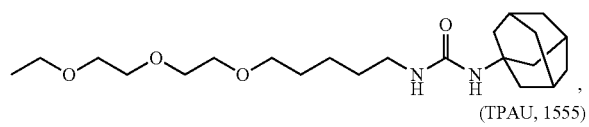

(TPAU, 1555)

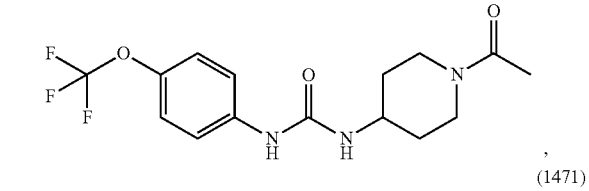

(1471)

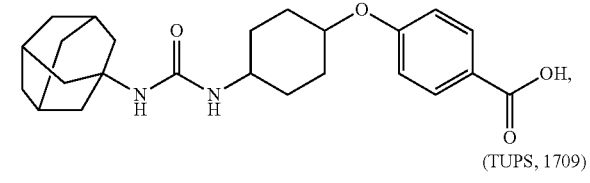

(TUPS, 1709)

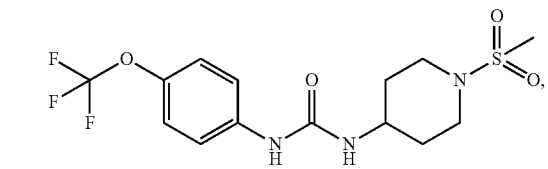

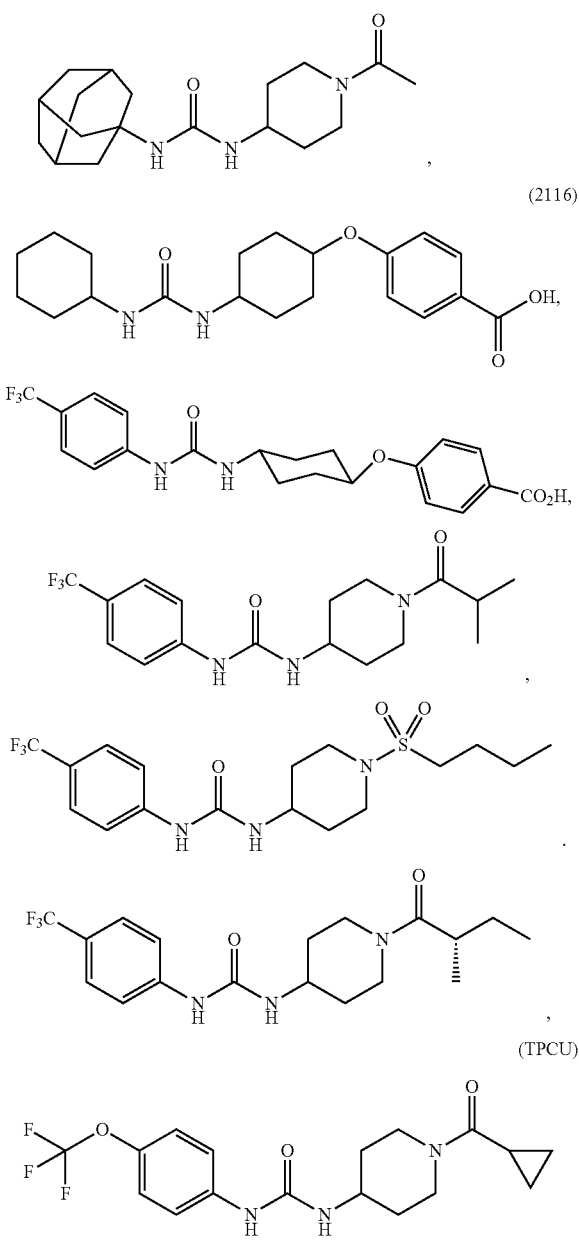

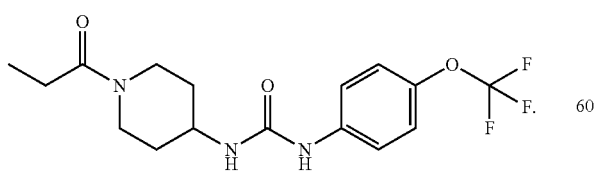

In some embodiments, the inhibitor of a soluble epoxide hydrolase is 1-trifluoromethoxyphenyl-3-(1-propionylpiperidin-4-yl) urea (TPPU) having the following structure:

In some embodiments, the inhibitor of a soluble epoxide hydrolase is 1-adamantanyl-3-{5-[2-(2-ethoxy)ethoxy)ethoxy]pentyl}urea (AEPU) having the following structure:

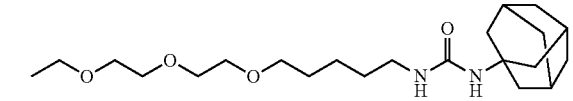 [SMILES: CCOCCOCCOCCCCCNC(=O)NC12CC3CC(CC(C3)C1)C2]

In some embodiments, the inhibitor of a soluble epoxide hydrolase is a compound of Formula (II):

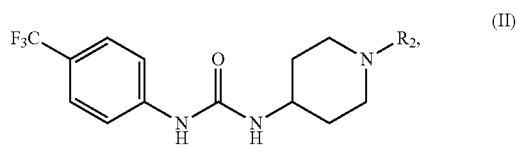

or a pharmaceutically acceptable salt thereof, wherein $R_2$ is selected from:

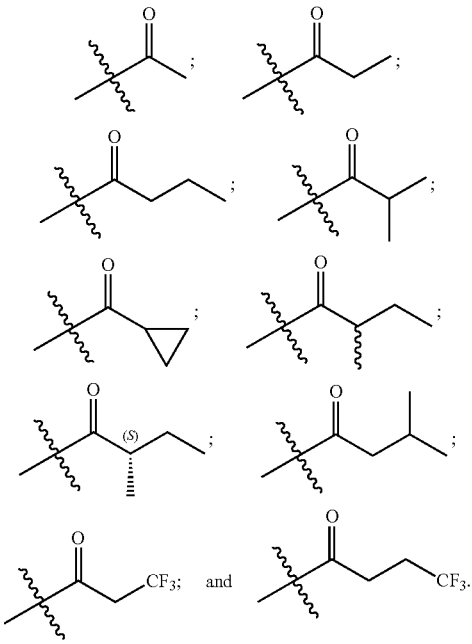

In some embodiments, the inhibitor of a soluble epoxide hydrolase is a compound of Formula (III):

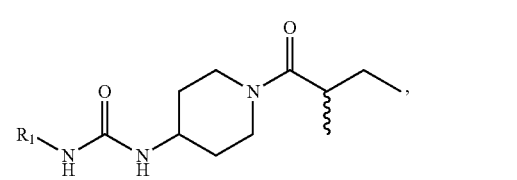

or a pharmaceutically acceptable salt thereof, wherein $R_1$ is selected from:

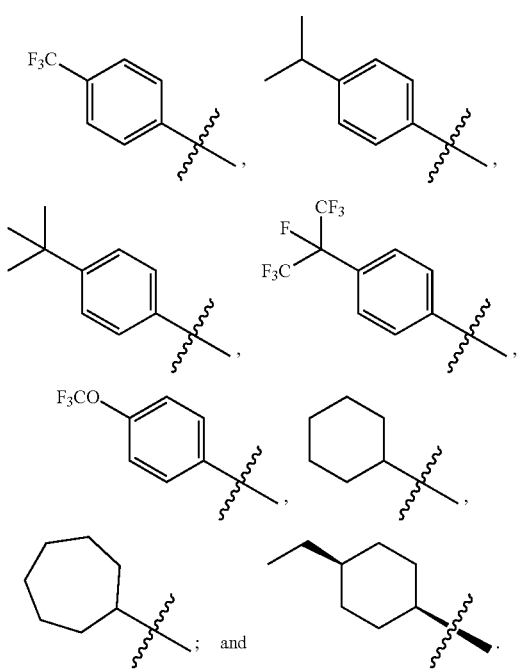

In some embodiments, the inhibitor of a soluble epoxide hydrolase is selected from the group consisting of:

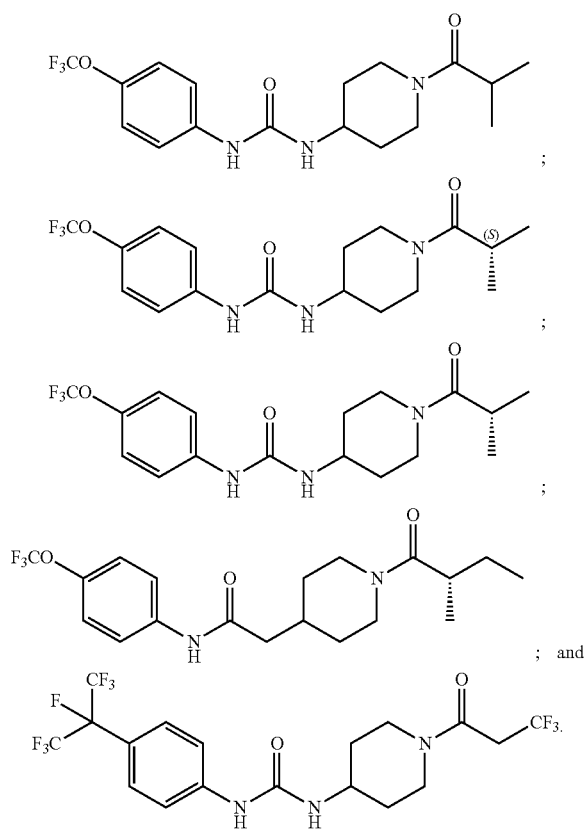

In some embodiments, the inhibitor of a soluble epoxide hydrolase is selected from the group consisting of:

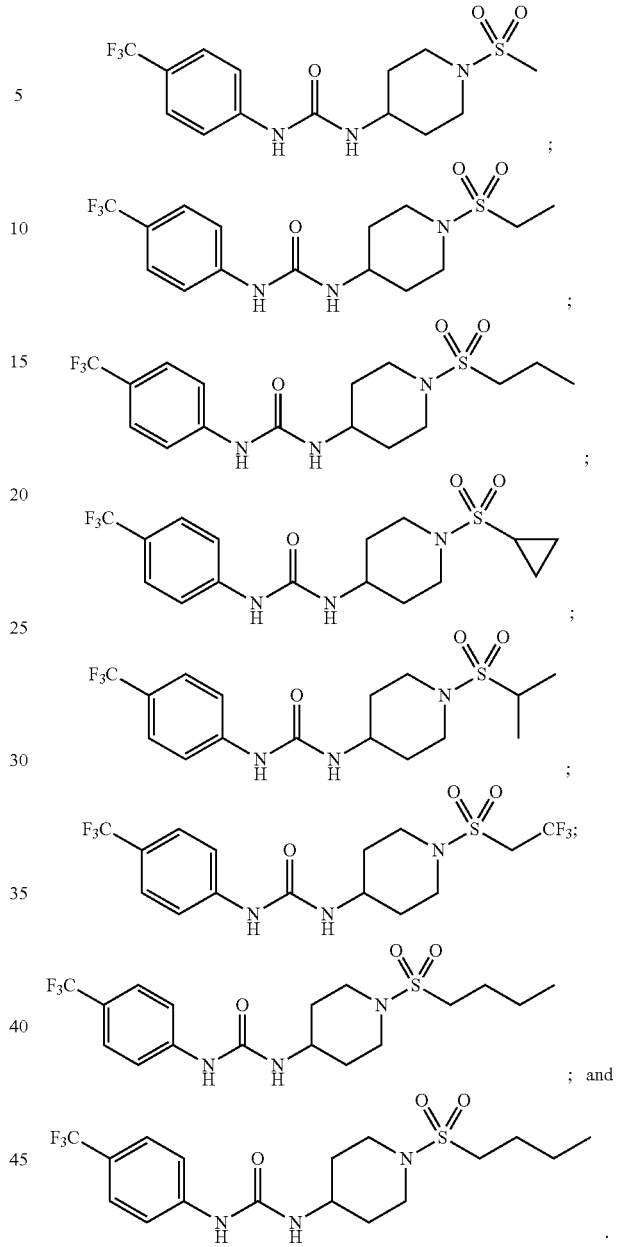

In some embodiments, the inhibitor of a soluble epoxide hydrolase is selected from any one of the inhibitors of a soluble epoxide hydrolase disclosed, for example, in Lee, K. S. S., et al. Optimized inhibitors of soluble epoxide hydrolase improve in vitro target residence time and in vivo efficacy. *Journal of Medicinal Chemistry*, 2014, 57, pages 7016-7030, which is incorporated herein by reference in its entirety.

In some embodiments. $IC_{50}$ of the inhibitor of a soluble epoxide hydrolase (sEH) (e.g., $IC_{50}$ obtained with respect to sEH of humans, primates, cats, dogs or hampsters) is from about 0.1 nM to about 3000 nM, from about 0.2 nM to about 2000 nM, from about 0.3 nM to about 1500 nM, from about 0.5 nM to about 1000 nM, from about 0.5 nM to about 700 nM, from about 1 nM to about 500 nM, from about 1 nM to about 400 nM, from about 1 nM to about 300 nM, from about 1 nM to about 200 nM, from about 1 nM to about 100 nM, from about 1 nM to about 90 nM, from about 1 nM to about 80 nM, from about 1 nM to about 50 nM, from about 1 nM to about 40 nM, from about 1 nM to about 30 nM, from about 1 nM to about 20 nM, from about 1 nM to about 10 nM, or from about 1 nM to about 5 nM. In some embodiments, $IC_{50}$ is about 1 nM, about 1.25 nM, about 1.5 nM, about 2 nM, about 2.5 nM, about 3 nM, about 4 nM, about 5 nM, about 10 nM, about 20 nM, about 30 nM, about 40 nM, about 50 nM, about or 100 nM.

In some embodiments, the inhibitor of a soluble epoxide hydrolase is soluble in water, sodium phosphate buffer, DMSO, PEG400, methanol, ethanol, triglycerides (e.g., Crisco oil), DMF, or trioleate. In some embodiments, solubility of the inhibitor of a soluble epoxide hydrolase in water or aqueous buffer is from about 1 μg/ml to about 1000 μg/ml, from about 1 μg/ml to about 900 μg/ml, from about 1 μg/ml to about 700 μg/ml, from about 1 μg/ml to about 500 μg/ml, from about 1 μg/ml to about 300 μg/ml, from about 1 μg/ml to about 250 μg/ml, from about 1 μg/ml to about 200 μg/ml, from about 1 μg/ml to about 150 μg/ml, from about 1 μg/ml to about 100, from about 1 μg/ml to about 60 μg/ml, or from about 1 μg/ml to about 50 μg/ml. n some embodiments, solubility of the inhibitor of a soluble epoxide hydrolase in water or aqueous buffer is about 1 μg/ml, about 10 μg/ml, about 20 μg/ml, about 30 μg/ml, about 40 μg/ml, about 50 μg/ml, about 75 μg/ml, about 100 μg/ml, about 150 μg/ml, about 200 μg/ml, about 250 μg/ml, about 300 μg/ml, about 400 μg/ml, about 500 μg/ml, about 600 μg/ml, about 750 μg/ml, about 900 μg/ml, or about 1000 μg/ml.

In some embodiments, the inhibitor of a soluble epoxide hydrolase (e.g. any one of sEHIs described herein) increases the half-life of the epoxymetabolite of a long chain polyunsaturated fatty acid (LCPUFA) (e.g., any of the epoxymetabolites described herein) by about 10%, about 20%, about 30%, about 50%, about 75%, about 100%, about 200%, about 300%, about 500%, about 750%, or about 1000%. In some embodiments, the inhibitor of a soluble epoxide hydrolase (e.g. any one of sEHIs described herein) increases the bioavailability (e.g., AUC) of the epoxymetabolite of a long chain polyunsaturated fatty acid (LCPUFA) (e.g., any of the epoxymetabolites described herein) by about 10%, about 20%, about 30%, about 50%, about 75%, about 100%, about 200%, about 300%, about 500%, about 750%, or about 1000%.

Pharmaceutically Acceptable Salts

In some embodiments, the present application provides a pharmaceutically acceptable salt of any one of the compounds disclosed herein (e.g., an inhibitor of a soluble epoxide hydrolase, a long chain polyunsaturated fatty acid (LCPUFA), or an epoxymetabolite of the long chain polyunsaturated fatty acid (LCPUFA)). In some embodiments, a salt of any one of the compounds disclosed herein is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds disclosed herein include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds disclosed herein include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

Preparation of Compounds

Compounds disclosed herein (e.g., an inhibitor of a soluble epoxide hydrolase, a long chain polyunsaturated fatty acid (LCPUFA), or an epoxymetabolite of the long chain polyunsaturated fatty acid (LCPUFA)), including salts thereof, can be prepared using known organic synthesis techniques and can be synthesized according to any of numerous possible synthetic routes. In some cases, compounds as provided herein are commercially available.

The inhibitors of a soluble epoxide hydrolase may be prepared using any one of the synthetic schemes and protocols disclosed, for example, in Lee, K. S. S., et al. Optimized inhibitors of soluble epoxide hydrolase improve in vitro target residence time and in vivo efficacy. *Journal of Medicinal Chemistry*, 2014, 57, pages 7016-7030, which is incorporated herein by reference in its entirety.

The epoxymetabolites of a long chain polyunsaturated fatty acid (LCPUFA) may be prepared using any one of the synthetic schemes and protocols disclosed, for example, in PCT application No. PCT/US2014/010880 (published as WO2014110261), US patent publication No. 2015/0335603, or in Yanai R, et al. (2014) Cytochrome P450-generated metabolites derived from omega-3 fatty acids attenuate neovascularization. *Proc Natl Acad Sci USA* 111(26):9603-9608, which are incorporated herein by reference in their entirety.

In some embodiments, the epoxymetabolites of ω-3 long chain polyunsaturated fatty acids (LCPUFAs) are synthesized ex vivo, e.g., biosynthesized using recombinant CYP450 from DHA or EPA. See, e.g., Lucas et al., Stereoselective epoxidation of the last double bond of polyunsaturated fatty acids by human cytochromes P450, *J Lipid Res.* 2010 May; 51(5): 1125-1133, which is incorporated herein by reference in its entirety.

In some embodiments, the epoxymetabolites of long chain polyunsaturated fatty acids (LCPUFAs) may be prepared from corresponding LCPUFAs using any of the known reagents (e.g., dimethyldioxirane, NaOCl, peracid such as meta-chloroperoxybenzoic acid, oxone or hydrogen peroxide).

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4$^{th}$ Ed., Wiley & Sons, Inc., New York (2006).

Combination Treatments-Anti-VEGF Agents

In some embodiments, the methods include co-administering an anti-Vascular Endothelial Growth Factor (VEGF) agent. In some embodiments, the anti-VEGF agent blocks VEGF signaling. There are at least three methods to block VEGF signaling that have been used to date. The first method is to inhibit VEGF (e.g. VEGF-A, -B, -C, -D, PGF) and/or VEGFR (e.g. VEGFR-1, -2, -3) using antibodies. Examples include: Avastin (bevacizumab), a recombinant humanized monoclonal antibody that binds to VEGF-A and prevent interaction of VEGF-A to VEGFR-1 and VEGFR-2 (see, e.g., Presta et al., Cancer Res. 57: 4593-4599 (1997); Hurwitz et al., N. Engl. J. Med. 350:2335-2342) (2004); 2C3, a mouse monoclonal antibody against VEGF-A (Zhang et al., Angiogenesis. 5:35-44 (2002); Brekken et al., Cancer Res. 58: 1952-9 (1998)); IMC-1121B, a human monoclonal antibody against VEGFR-2 (Rockwell and Goldstein, U.S. Pat. No. 6,811,779); CDP-791, PEGylated, humanized di-Fab fragment that binds to VEGFR-2 (Ton et al., Clin. Cancer Res. 13:7113-711 (2007)). Lucentis (ranibizumab) is a recombinant humanized monoclonal antibody that binds to VEGF-A, but its approved usage is for treatment of patients with neovascular age-related macular degeneration (available from Genentech).

A second method uses protein kinase inhibitors to inhibit VEGFR (e.g. VEGFR-1, -2, -3). At least two known FDA-approved small molecule inhibitors are on the market: Sutent (sunitinib) (Goodman et al., Clin. Cancer Res. 13:1367-1373 (2007)) and Nexavar (sorafenib) (Kane et al., Clin. Cancer Res. 12:7271-8 (2006)). Other kinase inhibitors include, but are not limited to: Vatalanib (PTK787/ZK222584) which inhibits VEGFR-1, -2, and -3 (Wood et al., Cancer Res. 60:2178-2189 (2000)); CEP-7055, inhibitor of VEGFR-1, -2, and -3 (Ruggeri et al., Cancer Res. 63: 5978-5991 (2003)); CP-547,632, inhibitor of VEGFR-2 and FGF (Beebe et al., Cancer Res. 63: 7301-7309 (2003)).

A third method uses the so-called "VEGF-trap," i.e., soluble hybrid VEGF receptors that bind to the VEGF ligand and prevent binding to VEGFRs (Holash et al., Proc. Natl. Acad. Sci. 99:11393-11398 (2002)).

In some embodiments, the anti-VEGF agent is an anti-VEGF antibody or antigen-binding portions thereof (such as Fv, Fab, or scFv portions) to inhibit VEGF binding to KDR and/or flt receptors, e.g., Avastin® (Bevacizumab). Avastin is a recombinant humanized monoclonal IgG1 antibody that binds to and inhibits the biologic activity of human VEGF both in vitro and in vivo. Bevacizumab contains human framework regions and the complementarity-determining regions of a murine antibody that binds to VEGF (Presta et al., Cancer Res 57:4593-9 1997). Avastin is available from Genentech (South San Francisco, Calif.). See also: Schlaeppi and Wood, Cancer and Metastasis Rev. 1999; 18:473-481; U.S. Pat. Nos. 7,169,901; 7,056,509; and 7,297,334; U.S. Pat. Pub. No. 20020032315; 20080187966; and 20090010883; and PCT No. WO 94/10202. In some embodiments, the antibody binds specifically to VEGF and block binding to VEGFR1, to VEGFR2, or block binding to both VEGFR1 and VEGFR2.

Other anti-VEGF agents include VEGF antagonists, which could compete with VEGF for binding to KDR and/or flt receptors (e.g. soluble truncated forms of flt receptor, which bind to VEGF, as described, for example, in WO 94/21679); and tyrosine kinase inhibitors.

In some embodiments, the anti-VEGF agent is a small interfering RNA (siRNA) targeting VEGF or a VEGFR, e.g., Bevasiranib (CandS; OPKO Health; a modified siRNA targeting all VEGF-A splice forms) or AGN-745 (Sirna-027; Merck; a chemically modified siRNA targeting VEGFR-1), see, e.g., de Fougerolles, Human Gene Therapy 19:125-132 (2008); and anti-VEGF aptamers (e.g., Macugen (pegaptanib; OSI Pharmaceuticals, a pegylated anti-VEGF-A aptamer), see, e.g., Tremolada et al. Am. J. Cardiovasc. Drugs 7:393-398 (2007)).

In some embodiments, the anti-VEGF agent is administered as part of the same treatment regimen as the compounds described herein. In some embodiments, the anti-VEGF agent is co-administered, e.g., as part of the same pharmaceutical composition as described above.

Compositions, Formulations and Routes of Administration

In some embodiments, the present application provides pharmaceutical compositions comprising a epoxymetabolite of a long chain polyunsaturated fatty acid (LCPUFA), or a pharmaceutically acceptable salt thereof; and a pharmaceutically acceptable carrier.

In some embodiments, the present application provides pharmaceutical compositions comprising an inhibitor of a soluble epoxide hydrolase, or a pharmaceutically acceptable salt thereof; and a pharmaceutically acceptable carrier.

In some embodiments, the present application provides pharmaceutical compositions comprising an epoxymetabolite of a long chain polyunsaturated fatty acid (LCPUFA), or a pharmaceutically acceptable salt thereof; an inhibitor of a soluble epoxide hydrolase, or a pharmaceutically acceptable salt thereof, and a pharmaceutically acceptable carrier.

The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

If required, the solubility and bioavailability of the compounds of the present application in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of the present application optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502, all of which are hereby incorporated by reference in their entireties.

The pharmaceutical compositions of the present application include those suitable for oral, rectal, nasal, topical (including buccal and sublingual), vaginal, parenteral, or intraperitoneal (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

In some embodiments, for treatment of ophthalmic conditions, intraocular administration or administration by eye drops may be used, inter alia; see, e.g., U.S. Pat. No. 7,582,785. Solutions or suspensions used for parenteral, intradermal, intraocular or subcutaneous application can include the following components: a sterile diluent such as water for injection, saline solution (e.g., 0.9% saline solution), dextrose solution (e.g., 5%) dextrose solution), fixed oils, polyethylene glycols (e.g., PEG400), glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, an epoxymetabolite of a long chain polyunsaturated fatty acid (LCPUFA) or an inhibitor of a soluble epoxide hydrolase is administered orally. Compositions of the present application suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In some embodiments, the inhibitor of a soluble epoxide hydrolase is administered to the subject with drinking water. In some embodiments, the inhibitor of a soluble epoxide hydrolase is administered to the subject as a solution in water, aqueous buffer (e.g., sodium phosphate buffer), ethanol, PEG400, triglycerides, trioleate, or mixtures thereof. In some embodiments, the solution of inhibitor of a soluble epoxide hydrolase in any of the aforementioned solvents is added to drinking water. In these cases, the amount of solvent in the drinking water is about 0.1% or less.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets. In some embodiments, the epoxymetabolite of a long chain polyunsaturated fatty acid (LCPUFA) is administered by local injection into or near the cornea, choroid, retina, vitreous, uvea, orbit, eyelid, conjunctiva, or iris.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031.

Topical administration of the pharmaceutical compositions of the present application is especially useful when the desired treatment involves areas or organs readily accessible by topical application.

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form.

In some embodiments, the topical composition comprises a combination of an epoxymetabolite of a long chain polyunsaturated fatty acid (LCPUFA) or an inhibitor of a soluble epoxide hydrolase, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

Application of the subject therapeutics may be local, so as to be administered at the site of interest. Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides a method of coating an implantable medical device comprising the step of contacting said device with the coating composition described above. It will be obvious to those skilled in the art that the coating of the device will occur prior to implantation into a mammal.

According to another embodiment, the present application provides a method of impregnating an implantable drug release device comprising the step of contacting said drug release device with a compound or composition of the present application. Implantable drug release devices include, but are not limited to, biodegradable polymer capsules or bullets, non-degradable, diffusible polymer capsules and biodegradable polymer wafers.

According to another embodiment, the present application provides an implantable medical device coated with a compound or a composition comprising a compound of the present application, such that said compound is therapeutically active.

According to another embodiment, the present application provides an implantable drug release device impregnated with or containing a compound or a composition comprising a compound of the present application, such that said compound is released from said device and is therapeutically active.

Where an organ or tissue is accessible because of removal from the subject, such organ or tissue may be bathed in a medium containing a composition of the present application, a composition of the present application may be painted onto the organ, or a composition of the present application may be applied in any other convenient way.

In the pharmaceutical compositions of the present application, an epoxymetabolite of a long chain polyunsaturated fatty acid (LCPUFA) or an inhibitor of a soluble epoxide hydrolase is present in an effective amount (e.g., a therapeutically effective amount).

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

In some embodiments, a therapeutically effective amount (e.g., when administered as described herein), is a dose sufficient to result in plasma concentration of an epoxymetabolite of a long chain polyunsaturated fatty acid (LCPUFA) (e.g., 17,18-EEQ or 19,20-EDP) from about 10 to about 1000 ng/ml. Exemplary doses include from about 0.1 µg/kg to about 1000 µg/kg, from about 0.2 µg/kg to about 900 µg/kg, from about 0.3 µg/kg to about 800 µg/kg, from about 0.4 µg/kg to about 700 µg/kg, from about 0.5 µg/kg to about 600 µg/kg, from about 0.6 µg/kg to about 500 µg/kg, from about 0.7 µg/kg to about 400 µg/kg, from about 0.8 µg/kg to about 300 µg/kg, from about 0.9 µg/kg to about 200 µg/kg, from about 1 µg/kg to about 100 µg/kg, from about 2 µg/kg to about 90 µg/kg, from about 3 µg/kg to about 80 µg/kg, from about 4 µg/kg to about 75 µg/kg, or from about 5 µg/kg to about 50 µg/kg. Exemplary doses also include about 0.5 µg/kg, 1 µg/kg, about 2 µg/kg, about 3 µg/kg, about 5 µg/kg, about 7 µg/kg, about 10 µg/kg, about 15 µg/kg, about 20 µg/kg, about 25 µg/kg, about 40 µg/kg, about 50 µg/kg, about 75 µg/kg, or about 100 µg/kg. Any of these doses may be administered once daily, twice daily or three time daily. In some embodiments, an epoxymetabolite of a long chain polyunsaturated fatty acid (LCPUFA) is administered once daily.

In some embodiments, a therapeutically effective amount (e.g., when administered as described herein), is a dose sufficient to result in plasma concentration of an inhibitor of sEH (e.g., 1-trifluoromethoxyphenyl-3-(1-propionylpiperidin-4-yl) urea) from about 100 to about 2000 nM. Exemplary doses include from about 0.05 mg/kg to about 100 mg/kg, from about 0.1 mg/kg to about 90 mg/kg, from about 0.15 mg/kg to about 80 mg/kg, from about 0.2 mg/kg to about 70 mg/kg, from about 0.3 mg/kg to about 60 mg/kg, from about 0.4 mg/kg to about 50 mg/kg, from about 0.5 mg/kg to about 40 mg/kg, from about 0.6 mg/kg to about 30 mg/kg, from about 0.7 mg/kg to about 25 mg/kg, from about 0.8 mg/kg to about 20 mg/kg, from about 0.9 mg/kg to about 15 mg/kg, from about 1 mg/kg to about 10 mg/kg, from about 0.1 mg/kg to about 10 mg/kg, from about 0.1 mg/kg to about 9 mg/kg, from about 0.1 mg/kg to about 8 mg/kg, from about 0.1 mg/kg to about 7 mg/kg, from about 0.1 mg/kg to about 6 mg/kg, from about 0.1 mg/kg to about 5 mg/kg, from about 0.1 mg/kg to about 4 mg/kg, from about 0.1 mg/kg to about 3 mg/kg, from about 0.1 mg/kg to about 2 mg/kg, or from about 0.1 mg/kg to about 1 mg/kg. Exemplary doses also include about 0.1 mg/kg, about 0.15 mg/kg, about 0.2 mg/kg, about 0.25 mg/kg, about 0.3 mg/kg, about 0.4 mg/kg, about 0.5 mg/kg, about 0.6 mg/kg, about 0.7 mg/kg, about 0.75 mg/kg, about 0.8 mg/kg, about 0.9 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 15 mg/kg, about 20 mg/kg, about 30 mg/kg, about 35 mg/kg, about 40 mg/kg, about 45 mg/kg or about 50 mg/kg. Any of these doses may be administered once daily, twice daily or three time daily. In some embodiments, an inhibitor of sEH is administered once daily.

In some embodiments, the epoxymetabolite of a long chain polyunsaturated fatty acid (LCPUFA) is administered by injection. In some embodiments, the epoxymetabolite of a long chain polyunsaturated fatty acid (LCPUFA) is administered by intraperitoneal injection. In some embodiments, the epoxymetabolite of a long chain polyunsaturated fatty acid (LCPUFA) is administered topically. In some embodiments, the inhibitor of a soluble epoxide hydrolase is administered orally. In some embodiments, epoxymetabolite of a long chain polyunsaturated fatty acid (LCPUFA) and the inhibitor of a soluble epoxide hydrolase are administered consecutively. In some embodiments, the epoxymetabolite of a long chain polyunsaturated fatty acid (LCPUFA) and the inhibitor of a soluble epoxide hydrolase are administered simultaneously. In some embodiments, the inhibitor of a soluble epoxide hydrolase is administered prior to the administration of the epoxymetabolite of a long chain polyunsaturated fatty acid (LCPUFA).

In some embodiments, at least one epoxymetabolite of a ω-3 long chain polyunsaturated fatty acid (LCPUFA) is administered in combination with at least one inhibitor of a soluble epoxide hydrolase.

In some embodiments: the epoxymetabolite of a ω-3 long chain polyunsaturated fatty acid (LCPUFA) is administered (e.g., by injection) in an amount from about 1 µg/kg to about 100 µg/kg (e.g. once daily); the inhibitor of a soluble epoxide hydrolase is administered orally in an amount from about 0.1 mg/kg to about 10 mg/kg (e.g., once daily); and the epoxymetabolite of a ω-3 long chain polyunsaturated fatty acid (LCPUFA) and the inhibitor of a soluble epoxide hydrolase are administered simultaneously.

In some embodiments: the epoxymetabolite of a ω-3 long chain polyunsaturated fatty acid (LCPUFA) is administered (e.g., by injection) in an amount from about 1 µg/kg to about 100 µg/kg (e.g., once daily); the inhibitor of a soluble epoxide hydrolase is administered orally in an amount from about 0.1 mg/kg to about 10 mg/kg (e.g., once daily); and the epoxymetabolite of a ω-3 long chain polyunsaturated fatty acid (LCPUFA) and the inhibitor of a soluble epoxide hydrolase are administered consecutively.

In some embodiments: the epoxymetabolite of a ω-3 long chain polyunsaturated fatty acid (LCPUFA) is administered (e.g., by injection) in an amount from about 1 µg/kg to about 100 µg/kg (e.g., once daily); the inhibitor of a soluble epoxide hydrolase is administered orally in an amount from about 0.1 mg/kg to about 10 mg/kg (e.g., once daily); and the inhibitor of a soluble epoxide hydrolase is administered prior to administering the epoxymetabolite of a ω-3 long chain polyunsaturated fatty acid (LCPUFA).

In some embodiments: the epoxymetabolite of a ω-3 long chain polyunsaturated fatty acid (LCPUFA) is administered by local injection into or near the cornea, choroid, retina, vitreous, uvea, orbit, eyelid, conjunctiva, or iris in an amount from about 5 µg/kg to about 50 µg/kg (e.g. once daily); the inhibitor of a soluble epoxide hydrolase is administered orally (e.g., in an aqueous solution such as drinking water) in an amount from about 0.1 mg/kg to about 10 mg/kg (e.g., once daily); and the epoxymetabolite of a ω-3 long chain polyunsaturated fatty acid (LCPUFA) and the inhibitor of a soluble epoxide hydrolase are administered simultaneously.

In some embodiments: the epoxymetabolite of a ω-3 long chain polyunsaturated fatty acid (LCPUFA) is administered by local injection into or near the cornea, choroid, retina, vitreous, uvea, orbit, eyelid, conjunctiva, or iris in an amount from about 5 µg/kg to about 50 µg/kg (e.g., once daily); the inhibitor of a soluble epoxide hydrolase is administered orally (e.g., in an aqueous solution such as drinking water) in an amount from about 0.1 mg/kg to about 10 mg/kg (e.g., once daily); and the epoxymetabolite of a ω-3 long chain polyunsaturated fatty acid (LCPUFA) and the inhibitor of a soluble epoxide hydrolase are administered consecutively.

In some embodiments: the epoxymetabolite of a ω-3 long chain polyunsaturated fatty acid (LCPUFA) is administered by local injection into or near the cornea, choroid, retina, vitreous, uvea, orbit, eyelid, conjunctiva, or iris in an amount from about 5 µg/kg to about 50 µg/kg (e.g., once daily); the inhibitor of a soluble epoxide hydrolase is administered orally (e.g., in an aqueous solution such as drinking water) in an amount from about 0.1 mg/kg to about 10 mg/kg (e.g., once daily); and the inhibitor of a soluble epoxide hydrolase is administered prior to administering the epoxymetabolite of a ω-3 long chain polyunsaturated fatty acid (LCPUFA).

In some embodiments: the epoxymetabolite of a ω-3 long chain polyunsaturated fatty acid (LCPUFA) is administered topically (e.g., in an eye-drop formulation) in an amount from about 1 µg/kg to about 100 µg/kg (e.g. once daily); the inhibitor of a soluble epoxide hydrolase is administered orally in an amount from about 0.1 mg/kg to about 10 mg/kg (e.g., once daily); and the epoxymetabolite of a ω-3 long chain polyunsaturated fatty acid (LCPUFA) and the inhibitor of a soluble epoxide hydrolase are administered simultaneously.

In some embodiments: the epoxymetabolite of a ω-3 long chain polyunsaturated fatty acid (LCPUFA) is administered topically (e.g., in an eye-drop formulation) in an amount from about 1 µg/kg to about 100 µg/kg (e.g., once daily); the inhibitor of a soluble epoxide hydrolase is administered orally in an amount from about 0.1 mg/kg to about 10 mg/kg (e.g., once daily); and the epoxymetabolite of a ω-3 long chain polyunsaturated fatty acid (LCPUFA) and the inhibitor of a soluble epoxide hydrolase are administered consecutively.

In some embodiments: the epoxymetabolite of a ω-3 long chain polyunsaturated fatty acid (LCPUFA) is administered topically (e.g., in an eye-drop formulation) in an amount from about 1 µg/kg to about 100 µg/kg (e.g., once daily); the inhibitor of a soluble epoxide hydrolase is administered orally in an amount from about 0.1 mg/kg to about 10 mg/kg (e.g., once daily); and the inhibitor of a soluble epoxide hydrolase is administered prior to administering the epoxymetabolite of a ω-3 long chain polyunsaturated fatty acid (LCPUFA).

In some embodiments: the epoxymetabolite of a ω-3 long chain polyunsaturated fatty acid (LCPUFA) is administered topically (e.g., in an eye-drop formulation) in an amount from about 5 µg/kg to about 50 µg/kg (e.g. once daily); the inhibitor of a soluble epoxide hydrolase is administered orally (e.g., in an aqueous solution such as drinking water) in an amount from about 0.1 mg/kg to about 10 mg/kg (e.g., once daily); and the epoxymetabolite of a ω-3 long chain polyunsaturated fatty acid (LCPUFA) and the inhibitor of a soluble epoxide hydrolase are administered simultaneously.

In some embodiments: the epoxymetabolite of a ω-3 long chain polyunsaturated fatty acid (LCPUFA) is administered topically (e.g., in an eye-drop formulation) in an amount from about 5 µg/kg to about 50 µg/kg (e.g., once daily); the inhibitor of a soluble epoxide hydrolase is administered orally (e.g., in an aqueous solution such as drinking water) in an amount from about 0.1 mg/kg to about 10 mg/kg (e.g., once daily); the epoxymetabolite of a ω-3 long chain polyunsaturated fatty acid (LCPUFA) and the inhibitor of a soluble epoxide hydrolase are administered consecutively.

In some embodiments: the epoxymetabolite of a ω-3 long chain polyunsaturated fatty acid (LCPUFA) is administered topically (e.g., in an eye-drop formulation) in an amount from about 5 µg/kg to about 50 µg/kg (e.g., once daily); the inhibitor of a soluble epoxide hydrolase is administered orally (e.g., in an aqueous solution such as drinking water) in an amount from about 0.1 mg/kg to about 10 mg/kg (e.g., once daily); and the inhibitor of a soluble epoxide hydrolase is administered prior to administering the epoxymetabolite of a ω-3 long chain polyunsaturated fatty acid (LCPUFA).

In some embodiments: epoxydocosapentaenoic acid (EDP) and/or epoxyeicosatetraenoic acid (EEQ) is administered by (e.g., by injection) in an amount from about 1 µg/kg to about 100 µg/kg (e.g. once daily); the inhibitor of soluble epoxide hydrolase TPPU is administered orally in an amount from about 0.1 mg/kg to about 10 mg/kg (e.g., once daily); and epoxydocosapentaenoic acid (EDP) and/or epoxyeicosatetraenoic acid (EEQ) and TPPU are administered simultaneously.

In some embodiments: epoxydocosapentaenoic acid (EDP) and/or epoxyeicosatetraenoic acid (EEQ) is administered by (e.g., by injection) in an amount from about 1 µg/kg to about 100 µg/kg (e.g. once daily); the inhibitor of soluble epoxide hydrolase TPPU is administered orally in an amount from about 0.1 mg/kg to about 10 mg/kg (e.g., once daily); and epoxydocosapentaenoic acid (EDP) and/or epoxyeicosatetraenoic acid (EEQ) and TPPU are administered consecutively.

In some embodiments: epoxydocosapentaenoic acid (EDP) and/or epoxyeicosatetraenoic acid (EEQ) is administered by (e.g., by injection) in an amount from about 1 µg/kg to about 100 µg/kg (e.g. once daily); the inhibitor of soluble epoxide hydrolase TPPU is administered orally in an amount from about 0.1 mg/kg to about 10 mg/kg (e.g., once daily); and the TPPU is administered prior to administering epoxydocosapentaenoic acid (EDP) and/or epoxyeicosatetraenoic acid (EEQ).

In some embodiments: epoxydocosapentaenoic acid (EDP) and/or epoxyeicosatetraenoic acid (EEQ) is administered by local injection into or near the cornea, choroid, retina, vitreous, uvea, orbit, eyelid, conjunctiva, or iris in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and epoxydocosapentaenoic acid (EDP) and/or epoxyeicosatetraenoic acid (EEQ) and TPPU are administered simultaneously.

In some embodiments: epoxydocosapentaenoic acid (EDP) and/or epoxyeicosatetraenoic acid (EEQ) is administered by local injection into or near the cornea, choroid, retina, vitreous, uvea, orbit, eyelid, conjunctiva, or iris in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and epoxydocosapentaenoic acid (EDP) and/or epoxyeicosatetraenoic acid (EEQ) and TPPU are administered consecutively.

In some embodiments: epoxydocosapentaenoic acid (EDP) and/or epoxyeicosatetraenoic acid (EEQ) is administered by local injection into or near the cornea, choroid, retina, vitreous, uvea, orbit, eyelid, conjunctiva, or iris in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and the TPPU is administered prior to administering epoxydocosapentaenoic acid (EDP) and/or epoxyeicosatetraenoic acid (EEQ).

In some embodiments: epoxydocosapentaenoic acid (EDP) and/or epoxyeicosatetraenoic acid (EEQ) is administered topically (e.g., in an eye-drop formulation) in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and epoxydocosapentaenoic acid (EDP) and/or epoxyeicosatetraenoic acid (EEQ) and TPPU are administered simultaneously.

In some embodiments: epoxydocosapentaenoic acid (EDP) and/or epoxyeicosatetraenoic acid (EEQ) is administered topically (e.g., in an eye-drop formulation) in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and epoxydocosapentaenoic acid (EDP) and/or epoxyeicosatetraenoic acid (EEQ) and TPPU are administered consecutively.

In some embodiments: epoxydocosapentaenoic acid (EDP) and/or epoxyeicosatetraenoic acid (EEQ) is administered topically (e.g., in an eye-drop formulation) in an amount from about 5 µg/kg to about 50 µg/kg (e.g. once daily); the inhibitor of soluble epoxide hydrolase TPPU is administered orally in an aqueous solution (e.g., with drinking water) in an amount from about 0.1 mg/kg to about 10 mg/kg (e.g., once daily); and the TPPU is administered prior to administering epoxydocosapentaenoic acid (EDP) and/or epoxyeicosatetraenoic acid (EEQ).

In some embodiments: 19,20-EDP and/or 17,18-EEQ is administered by (e.g., by injection) in an amount from about 1 µg/kg to about 100 µg/kg (e.g. once daily); the inhibitor of soluble epoxide hydrolase TPPU is administered orally in an amount from about 0.1 mg/kg to about 10 mg/kg (e.g., once daily); and 19,20-EDP and/or 17,18-EEQ and TPPU are administered simultaneously.

In some embodiments: 19,20-EDP and/or 17,18-EEQ is administered by (e.g., by injection) in an amount from about 1 µg/kg to about 100 µg/kg (e.g. once daily); the inhibitor of soluble epoxide hydrolase TPPU is administered orally in an amount from about 0.1 mg/kg to about 10 mg/kg (e.g., once daily); and 19,20-EDP and/or 17,18-EEQ and TPPU are administered consecutively.

In some embodiments: 19,20-EDP and/or 17,18-EEQ is administered by (e.g., by injection) in an amount from about 1 µg/kg to about 100 µg/kg (e.g. once daily); the inhibitor of soluble epoxide hydrolase TPPU is administered orally in an amount from about 0.1 mg/kg to about 10 mg/kg (e.g., once daily); and the TPPU is administered prior to administering 19,20-EDP and/or 17,18-EEQ.

In some embodiments: 19,20-EDP and/or 17,18-EEQ is administered by local injection into or near the cornea, choroid, retina, vitreous, uvea, orbit, eyelid, conjunctiva, or iris in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and 19,20-EDP and/or 17,18-EEQ and TPPU are administered simultaneously.

In some embodiments: 19,20-EDP and/or 17,18-EEQ is administered by local injection into or near the cornea, choroid, retina, vitreous, uvea, orbit, eyelid, conjunctiva, or iris in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and 19,20-EDP and/or 17,18-EEQ and TPPU are administered consecutively.

In some embodiments: 19,20-EDP and/or 17,18-EEQ is administered by local injection into or near the cornea, choroid, retina, vitreous, uvea, orbit, eyelid, conjunctiva, or iris in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and the TPPU is administered prior to administering 19,20-EDP and/or 17,18-EEQ.

In some embodiments: 19,20-EDP and/or 17,18-EEQ is administered topically (e.g., in an eye-drop formulation) in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and 19,20-EDP and/or 17,18-EEQ and TPPU are administered simultaneously.

In some embodiments: 19,20-EDP and/or 17,18-EEQ is administered topically (e.g., in an eye-drop formulation) in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and 19,20-EDP and/or 17,18-EEQ and TPPU are administered consecutively.

In some embodiments: 19,20-EDP and/or 17,18-EEQ is administered topically (e.g., in an eye-drop formulation) in an amount from about 5 µg/kg to about 50 µg/kg (e.g. once daily); the inhibitor of soluble epoxide hydrolase TPPU is administered orally (e.g., in an aqueous solution such as drinking water) in an amount from about 0.1 mg/kg to about 10 mg/kg (e.g., once daily); and the TPPU is administered prior to administering 19,20-EDP and/or 17,18-EEQ.

Kits

The present invention also includes pharmaceutical kits useful, for example, in the treatment or prevention of diseases referred to herein, such as disorders associated with a neovascularization (e.g. age-related macular degeneration, Stargardt's disease, retinopathy of prematurity (ROP); diabetic retinopathy; retinal vein occlusion; sickle cell retinopathy; radiation retinopathy, iritis, and conjunctivitis), disorder associated with angiogenesis (e.g., cancer), disorders associated with vascular leakage (e.g. stroke), disorders associated with inflammation (e.g., arthritis), which include one or more containers containing a compound described herein or a pharmaceutical composition comprising a therapeutically effective amount of a compound described herein. In some embodiments, the compound is purified. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

In some embodiments, the present application is directed to a kit comprising:
(iii) one or more epoxymetabolites of a long chain polyunsaturated fatty acids (LCPUFA); and
(iv) one or more inhibitors of a soluble epoxide hydrolase.

In some embodiments, the epoxymetabolite of a long chain polyunsaturated fatty acids (LCPUFA) is purified. In some embodiments, the inhibitor of a soluble epoxide hydrolase is purified.

EXAMPLES

Materials and methods.

Animals:

All animal procedures adhered to the Association for Research in Vision and Ophthalmology Statement for the Use of Animals in Ophthalmic and Vision Research. The Animal Care and Use Committee of Massachusetts Eye and Ear Infirmary approved the protocol for the experiments outlined herein. Tie2-CYP2C8 transgenic (Tg) mice, which overexpress human CYP2C8 in endothelial cells (Lee C R, et al. (2010) Endothelial expression of human cytochrome P450 epoxygenases lowers blood pressure and attenuates hypertension-induced renal injury in mice. FASEB J 24(10): 3770-3781); Tie2-hsEH Tg mice, which overexpress human sEH in endothelial cells (Edin M L, et al. (2011) Endothelial expression of human cytochrome P450 epoxygenase CYP2C8 increases susceptibility to ischemia-reperfusion injury in isolated mouse heart. FASEB J 25(10):3436-3447); and sEH null mice, which have systemic knockout of sEH (Sinal C J, et al. (2000) Targeted disruption of soluble epoxide hydrolase reveals a role in blood pressure regulation. J Biol Chem 275(51):40504-40510), were kindly provided by Dr. Darryl C. Zeldin (NIH/NIEHS). All mice were on the C57BL/6 (area R16) genetic background from Charles River (Wilmington, Mass., USA). These C57BL/6 mice were used as control mice for CNV experiments involving the aforementioned CYP Tg mice. Male C57BL/6 mice (stock no. 000664) at 6 to 8 weeks of age obtained from Jackson Laboratories (Bar Harbor, Me., USA) were used for all other experiments.

Diet and Bioactive Lipid Metabolites:

Mice were fed one of three experimental diets: a diet containing high ω-3 LCPUFAs [eicosapentaenoic acid (EPA) 478.5 mg/g diet and docosahexaenoic acid (DHA) 193.5 mg/g diet, with no arachidonic acid (AA)], a diet devoid of ω-3 LCPUFAs but containing the ω-6 LCPUFA AA [2% (wt/wt)], and a standard control diet which was completely devoid of AA, EPA, and DHA; the base fatty acids in the diets originated predominantly from soybean. The ω-3 LCPUFAs were obtained from Pronova Biopharma (PronovaPure 500:200 EE, Denmark) and the experimental diets were formulated by ssniff (Germany). Mice were placed on these diets 2 weeks prior to the induction of CNV and for the rest of the experiment duration. The control diet was used for the experiments involving CYP-derived fatty acids to avoid the influence of fatty acids from the diet. CYP-derived fatty acids, 17,18-epoxyeicosaquatraenoic acid (EEQ), 19,20-epoxydocosapentaenoic acid (EDP), and 8,9-, 11,12-, 14,15-epoxyeicosatrienoic acid (EET), were obtained from Cayman Chemical (Ann Arbor, Mich., USA). Mice were injected intraperitoneally (i.p.) daily with 17,18-EEQ, 19,20-EDP, 8,9-, 11,12-, 14,15-EETs, or PBS as a vehicle control beginning immediately after CNV induction. Based on our earlier work, a dose of 50 µg/kg/day for these agents was used to assess the role of each of the aforementioned bioactive metabolites in the laser-induced CNV model (Yanai R, et al. (2014) Cytochrome P450-generated metabolites derived from omega-3 fatty acids attenuate neovascularization. Proc Natl Acad Sci USA 111(26):9603-9608). The stable 17,18-EEQ analog, named C21, was synthesized as previously described (Falck J R, et al. (2011) 17(R),18(S)-epoxyeicosatetraenoic acid, a potent eicosapentaenoic acid (EPA) derived regulator of cardiomyocyte contraction: structure-activity relationships and stable analogues. J Med Chem 54(12):4109-4118). This analog was also injected 50 µg/kg/day i.p. daily at the same dose as the other fatty acid metabolites. 1-Trifluoromethoxyphenyl-3-(1-propionylpiperidin-4-yl) urea, a potent sEH inhibitor, was synthesized as previously described (Rose T E, et al. (2010) 1-Aryl-3-(1-acylpiperidin-4-yl)urea inhibitors of human and murine soluble epoxide hydrolase: structure-activity relationships, pharmacokinetics, and reduction of inflammatory pain. J Med Chem 53(19):7067-7075), dissolved in polyethylene glycol 400 (PEG400), and administered in the drinking water at a dose of 1 mg/kg/day 3 days prior to the induction of CNV and through the duration of the experiment. Drinking water containing PEG400 alone served as the vehicle control group.

Laser-Induced CNV Model:

A 532 nm laser (Oculight GLx Laser System, IRIDEX) attached to a slit lamp was used for photocoagulation. In order to view the posterior pole of the eye, a coverslip with a drop of Goniosol was applied to applanate the cornea. For size and leakage studies, 4 laser-induced lesions were made around the optic nerve in a clock-wise manner (i.e., 3, 6, 9, and 12 o'clock). For fluorescence-activated cell sorting (FACS) and laser-capture microdissection (LCM) analysis, 10 lesions were placed. The laser was set as follows: 100 mW power, 100 µm spot size, and 0.1 s pulse duration. The appearance of a bubble at the site of photocoagulation signified a disruption in Bruch's membrane, and so any laser-injury without a corresponding bubble was excluded from analysis. Seven days after laser treatment, mouse eyes were enucleated and subsequently fixed in 4% paraformaldehyde. Whole retinas were then separated from the underlying choroid and sclera (i.e., eyecup). At a dilution of 1:100, Alexa Fluor 488 conjugated to isolectin B4 (Invitrogen) was used to stain the eyecup overnight at room temperature. PermaFluor aqueous mount (Thermo Scientific) was then used to flatmount the eyecup with the choroid facing upward and the sclera facing downward. Flatmount images were captured using a Zeiss AxioCam MRm camera and Zeiss AxioObserver (Z1) microscope, and ImageJ software (National Institutes of Health) was used to assess fluorescent CNV lesions.

Fluorescein Angiography:

A Micron IV Retinal Imaging Microscope (Phoenix Research Laboratories, Pleasanton, Calif.) was used to take fluorescein images. First, mice were anesthetized with Avertin (Sigma, St. Louis, Mo.) and kept on a heating pad (37° C.) to maintain body temperature. 5% phenylephrine and 0.5% tropicamide were used for pupil dilation. The corneas were covered with 2.5% Goniovisc (HUB Pharmaceuticals, Rancho Cucamonga, Calif.) and then placed in contact with the Micron camera lens. Images were obtained 3-5 and 7-10 minutes after i.p. injection of 0.1 ml of 2% fluorescein sodium (Akorn, Lake Forest, Ill.) using StreamPix software (Phoenix Research Laboratories, Pleasanton, Calif.). A previously established scheme was used to grade the hyperfluorescent lesions: faint or mottled fluorescence without leakage was scored as 0 (i.e., no leakage); hyperfluorescence without any increase in size or intensity was scored as 1 (i.e., debatable leakage); hyperfluorescence with constant size but increasing intensity was scored as 2A (i.e., definite leakage); and hyperfluorescence with increasing size and intensity was scored as 2B (i.e., clinically significant leakage).

Spectral Domain-Optical Coherence Tomography:

Seven days after laser photocoagulation, a Bioptigen system was used to conduct spectral domain-optical coherence tomography (SD-OCT) as previously described (Yanai R, et al. (2014) Cytochrome P450-generated metabolites derived from omega-3 fatty acids attenuate neovascularization. Proc Natl Acad Sci USA 111(26):9603-9608). Mice were first anesthetized and placed on a freely rotating cassette customized for optimal eye alignment. AB-scan with an area size of 1.4×1.4 mm was obtained using 100 horizontal, raster, and consecutive B-scan lines, each composed of 1,000 A-scans. Cross-sectional CNV lesion size from these OCT images was measured in ImageJ using sections through the center (i.e., midline through the ruptured area of Bruch's membrane and the retinal pigment epithelium) of each CNV lesion.

Liquid Chromatography-Tandem Mass Spectrometry:

Seven days after CNV induction, plasma samples were obtained from mice fed ω-3, ω-6, or control diets for analysis of the CYP-mediated metabolite profile via liquid chromatography-tandem mass spectrometry (LC-MS/MS) as previously described (Arnold C, et al. (2010) Arachidonic acid-metabolizing cytochrome P450 enzymes are targets of {omega}-3 fatty acids. J Biol Chem 285(43):32720-32733). Plasma samples were combined with an internal standard solution (i.e., 10 ng each of 14,15-epoxyeicosatrienoic acid-d8, 20-hydroxyeicosatetraenoic acid-d6, and 14,15-dihydroxyeicosatrienoic acid-al; Cayman Chemical) for subsequent alkaline hydrolysis. Agilent Bond Elute Certify II columns were then used for the solid-phase extraction of metabolites. Metabolite analysis was performed in a solvent system (acetonitrile and 0.1% aqueous formic acid) with an Agilent 1200 HPLC system and Phenomenex Kinetex-C18 column (2.6 µm; 2.1 Å~150 mm). Starting at a 5% acetonitrile concentration, gradient elution was conducted by increasing the acetonitrile concentration to 90% in 10 min and then held at 90% for 10 min, with a flow rate of 0.3 mL/min. The HPLC system was linked to a mass spectrometer (Agilent 6460 triple quadrupole) with a source of electrospray ionization. As previously described (Arnold C, et al. (2010) Arachidonic acid-metabolizing cytochrome P450 enzymes are targets of {omega}-3 fatty acids. J Biol Chem 285(43):32720-32733), multiple reaction monitoring (negative mode) was used to analyze the CYP-mediated metabolites, and the results were calculated via Agilent Mass Hunter software. The concentrations of metabolites are expressed in ng/mL of serum or ng/mg of retina protein which were obtained with the Lowry assay.

Autoperfused Microflow Chamber Microscopy:

An autoperfused microflow chamber assay was used to assess leukocyte rolling velocity as previously described (Mulki L, Sweigard J H, & Connor K M (2014) Assessing leukocyte-endothelial interactions under flow conditions in an ex vivo autoperfused microflow chamber assay. J Vis Exp (94)). A combination of intercellular adhesion molecule 1 (ICAM-1) and P-selectin (R&D Systems), each at a concentration of 5 µg/mL, was used to coat translucent microchambers (0.4×0.04×50 mm, VitroCom) overnight at 4° C. Biocompatible polyester tubing (PE10; Becton Dickinson) was attached to both ends of each microchamber, and the apparatus was subsequently incubated for 1 hour with 0.1% BSA (Sigma-Aldrich) in order to prevent nonspecific leukocyte interaction with the inner surface of the apparatus. The left jugular vein and right carotid artery in an anesthetized mouse were surgically connected to the free ends of both tubes, thus allowing blood to flow from the right carotid artery and into the microchamber (via the inlet tube), and then into the left jugular vein (via the outlet tube) for recirculation. Blood flow rate through the microchamber was controlled via a screw valve on the inlet tube that could change the tube diameter. For continuous blood pressure measurements, three-way connectors were used to embed microtransducers (Harvard Apparatus) before and after the microchamber. Digitizing the analog output from these microtransducers required an A/D converter (ML785 PowerLab/8SP; ADInstruments) linked to a computer running CHART V7 software (ADInstruments). In terms of the hemodynamic conditions in the chamber, the pressure drop ($\Delta P$) was calculated as the difference between the recorded pressure readings before (inlet) and after (outlet) the microchamber, and $\Delta P$ was used to calculate shear stress ($\tau$) as previously described (Almulki L, et al. (2009) Surprising up-regulation of P-selectin glycoprotein ligand-1 (PSGL-1) in endotoxin-induced uveitis. FASEB J 23(3):929-939; Hafezi-Moghadam A, Thomas K L, & Cornelssen C (2004) A novel mouse-driven ex vivo flow chamber for the study of leukocyte and platelet function. Am J Physiol Cell Physiol 286(4):C876-892). A fixed-stage intravital microscope (Leica) with a 63× objective and a monochromic camera (DFC 360 FX; Leica) were used to observe and record leukocyte rolling along immobilized adhesion molecules. Recordings lasted at least 30 s and incorporated ten different fields of view. Using ImageJ software, leukocyte rolling velocity was calculated based on individual cell displacement along the surface of the chamber over time (i.e., $\Delta d/\Delta t$). Flux was calculated as the mean number of leukocytes interacting with the chamber surface per field of view (i.e., average of 10 independent fields of view). There were no significant differences in the flux of peripheral blood leukocytes (PBLs) from mice on either ω-3 or ω-6 fatty acid diets.

Isolation of PBLs for Flow Cytometric Analysis of CD11b and CD18:

An EDTA-treated syringe was used to obtain blood from mouse hearts. The blood was then incubated on ice for 30 min with phycoerythrin conjugated to rat monoclonal antibodies CD18 (C71/16; BD Biosciences) or CD11b (M1/70; BD Biosciences), or with isotype control antibodies (concentration of 1 µg per $1\times10^6$ total cells). After lysing red blood cells (Easy-Lyse, Leinco Technologies), the solution was centrifuged and the remaining cells were resuspended for flow cytometry (Cytomics FC500 instrument, Beckman Coulter). PBLs were gated based on their characteristic forward and side scatter pattern, and subsequent analysis was conducted with FlowJo 10.0 software (Beckman Coulter).

Laser-Capture Microdissection:

Immediately after enucleation, mouse eyes were placed in optimum cutting temperature (OCT) compound and swiftly frozen. Under RNase-free conditions, eyes were cryosectioned (10 µm thickness per section) and mounted on polyethylene naphthalate glass slides (Leica). After dehydrating with washes of 50, 75, and 100% ethanol, the slides were stained with isolectin B4 at a dilution of 1:50 in 1 mM CaCl2. Laser-capture microdissection (Leica LMD 7000 system) was used to isolate chorioretinal vessels in CNV lesions, which were then placed in RNA-stabilizing buffer (RNeasy Micro Kit; Qiagen). Reverse transcription of the extracted RNA was achieved with SuperScript III reverse transcriptase and random hexamer primers (Invitrogen). Real-time PCR was conducted on a StepOne real-time PCR System (Applied Biosystems) with mouse TaqMan expression assays for the following genes (Applied Biosystems): E-selectin (Mm00441278_m1), kam-1 (Mm00516023_m1), and β-actin (Mm00607939_s1). All data were normalized to β-actin cDNA.

Statistical Analysis:

Results are shown as means±SEM. The student t test was used to compare two groups while Dunnett's test was used to compare more than two groups. Statistical significance was defined as a P value of <0.05.

Example 1—Tie2-CYP2C8 Mice Overexpress Epoxygenase CYP2C8 in Endothelial Cells (Promoting Metabolism of LCPUFAs to their Active Eicosanoids in Endothelial Cells)

Figure 1B:
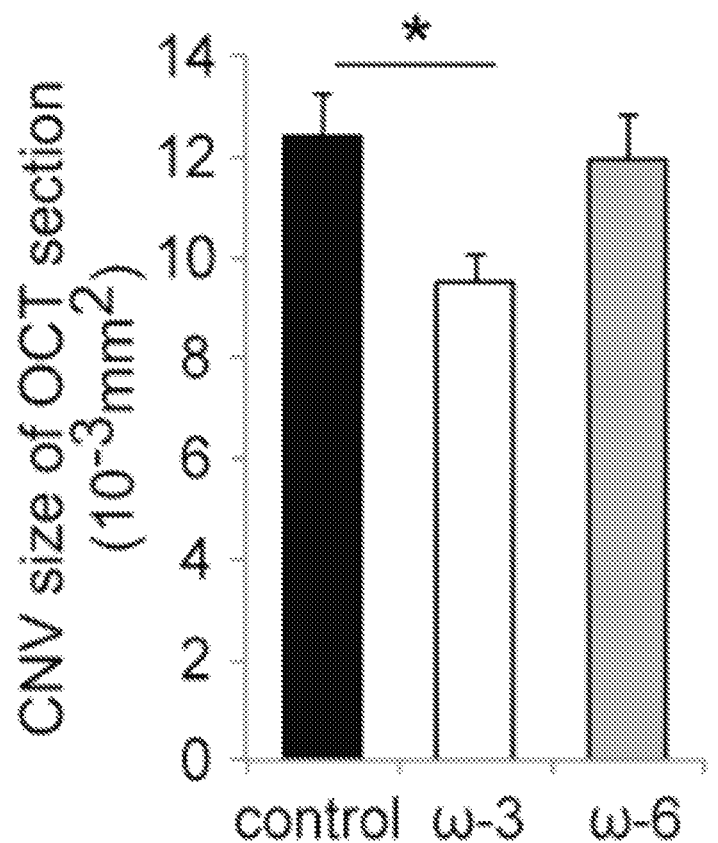
Figure 1B:
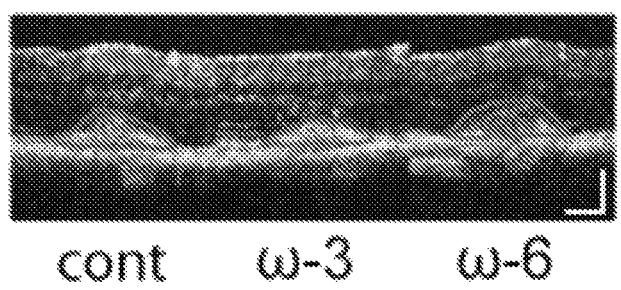
Figure 1C:
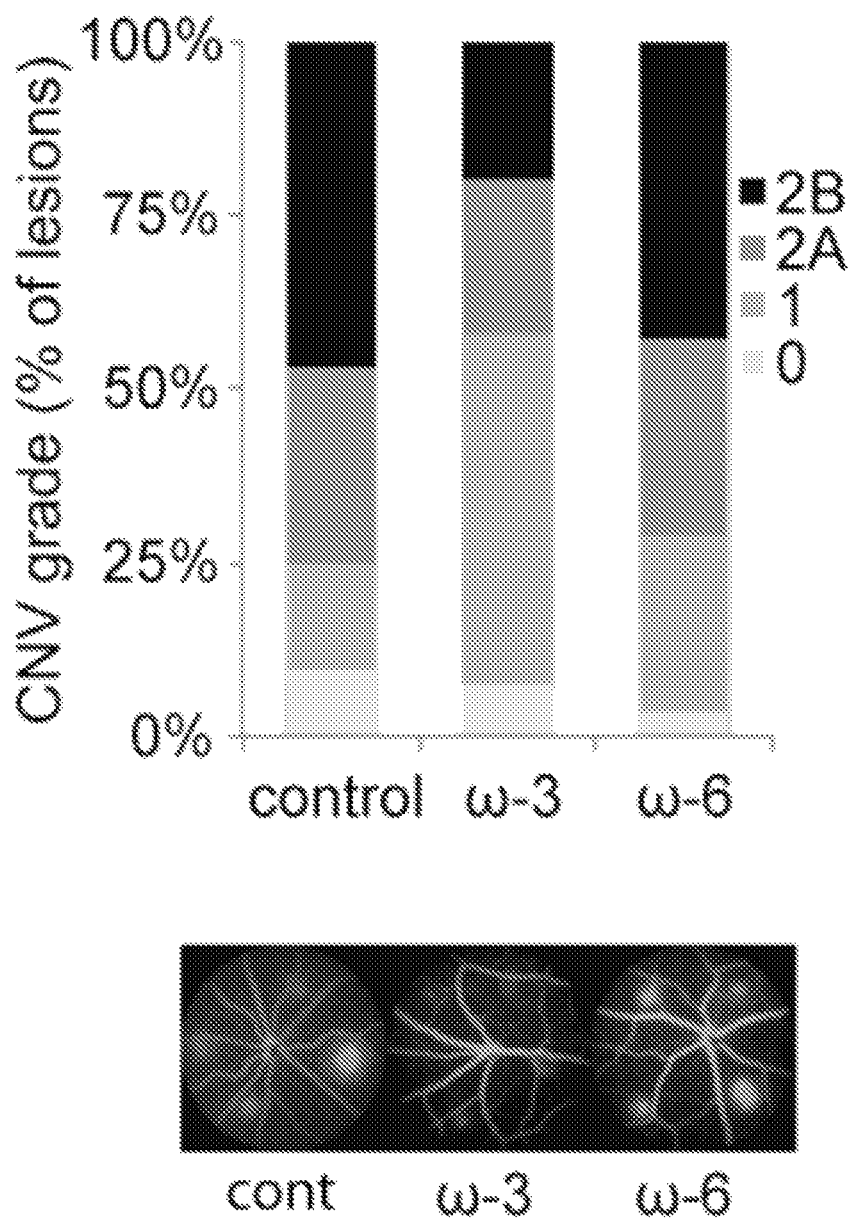

Tie2-CYP2C8-Tg mice overexpress the monooxygenase CYP2C8 in endothelial cells, which promotes the metabolism of the primary LCPUFAs to their active downstream fatty acids. FIGS. 1A-1C show: (A, B) Lesion size at 7 d after CNV induction was assessed by staining of choroidal flat-mount preparations with fluorescent isolectin B4 (A), and cross-sectional area of lesions was quantified by SD-OCT (demarcated by circling)(B), for Tie2-CYP2C8-Tg mice fed a control diet (n=25 lesions, respectively), ω-3 LCPUFAs enriched diet (n=38 lesions, respectively), or ω-6 LCPUFAs enriched diet (n=30 lesions, respectively) beginning 2 weeks before laser photocoagulation. Tie2-CYP2C8-Tg mice overexpress the monooxygenase CYP2C8 in endothelial cells, which promotes the metabolism of the primary LCPUFAs to their active downstream fatty acid metabolites. ω-3 LCPUFAs decreased CNV size in choroidal flatmounts and OCT sections compared to the control diet and ω-6 LCPUFAs diet groups. Data are presented as means±SEM. *P<0.05. Scale bars: 100 µm. (C) Fluorescein leakage in CNV lesions was graded at 7 d after CNV induction in Tie2-CYP2C8-Tg mice fed a control diet (n=25 lesions), ω-3 LCPUFAs enriched diet (n=38 lesions), or ω-6 LCPUFAs enriched diet (n=30 lesions) beginning 2 weeks before laser photocoagulation. ω-3 LCPUFAs attenuated fluorescein leakage from the CNV lesions compared to the control diet and ω-6 diet groups.

The size of CNV lesions 7 days after laser induction was significantly decreased in Tie2-CYP2C8-Tg mice fed a diet enriched with EPA and DHA compared to mice fed a control diet, as assessed in choroidal flatmounts and OCT cross-sectional images. Vascular leakage in CNV lesions, assessed by fluorescein angiography, was also significantly decreased in Tie2-CYP2C8-Tg mice fed a diet enriched with EPA and DHA compared to mice on a control diet.

Figure 2A:
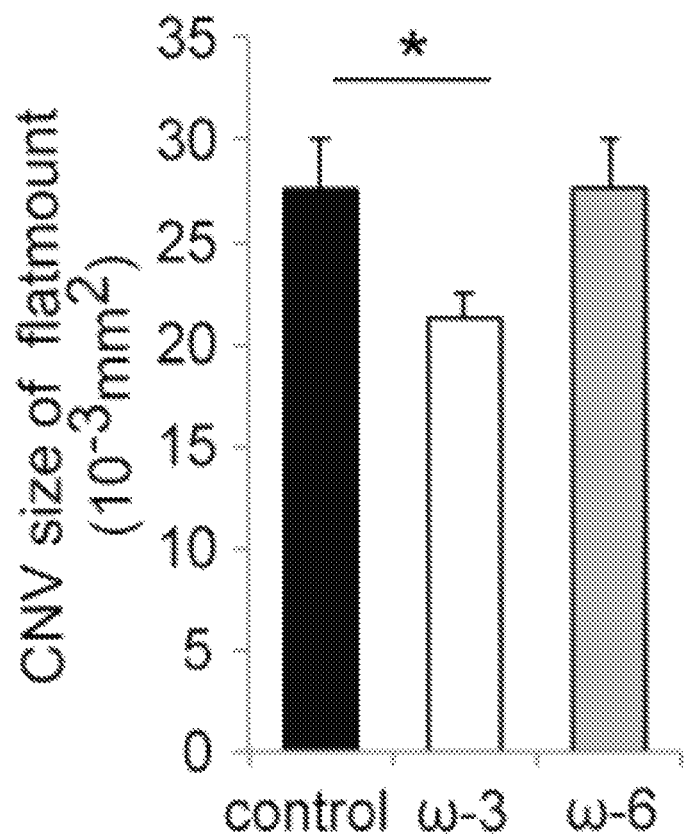
FIGS. 2A-2C. Lesion size at 7 d after CNV induction was assessed by staining of choroidal flat-mount preparations with fluorescent isolectin B4 (FIG. 2A), and cross-sectional area of lesions was quantified by SD-OCT (demarcated by circling) (FIG. 2B), for soluble epoxide hydrolase (sEH) null mice fed a control diet (n=49 lesions, respectively), ω-3 LCPUFAs enriched diet (n=57 lesions, respectively), or ω-6 LCPUFAs enriched diet (n=50 lesions, respectively) beginning 2 weeks before laser photocoagulation.
Figure 2A:
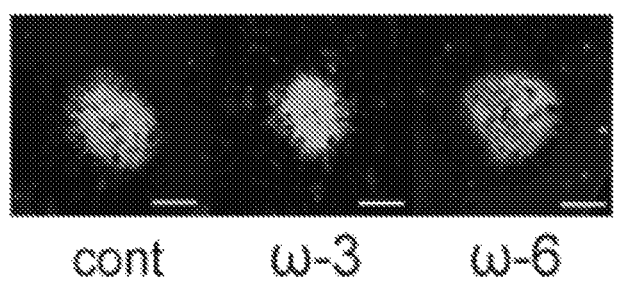
Figure 2B:
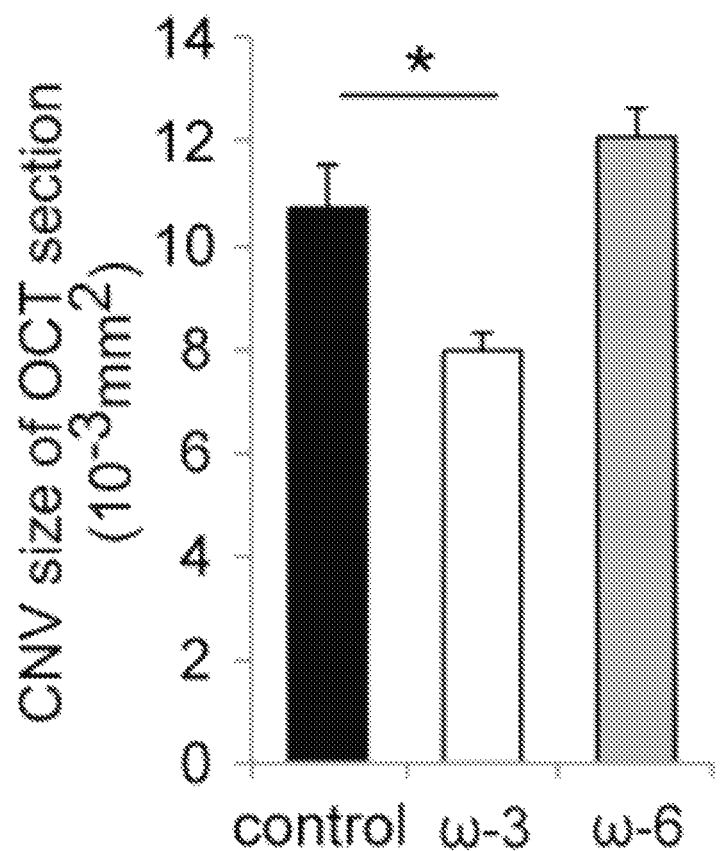
Figure 2B:
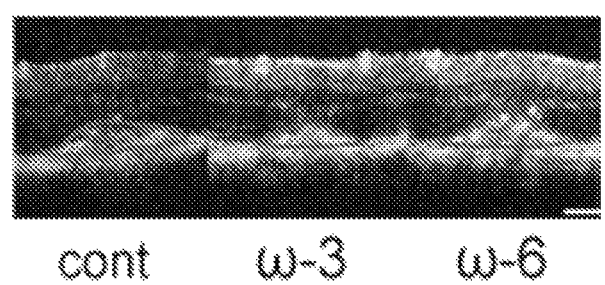
Figure 2C:
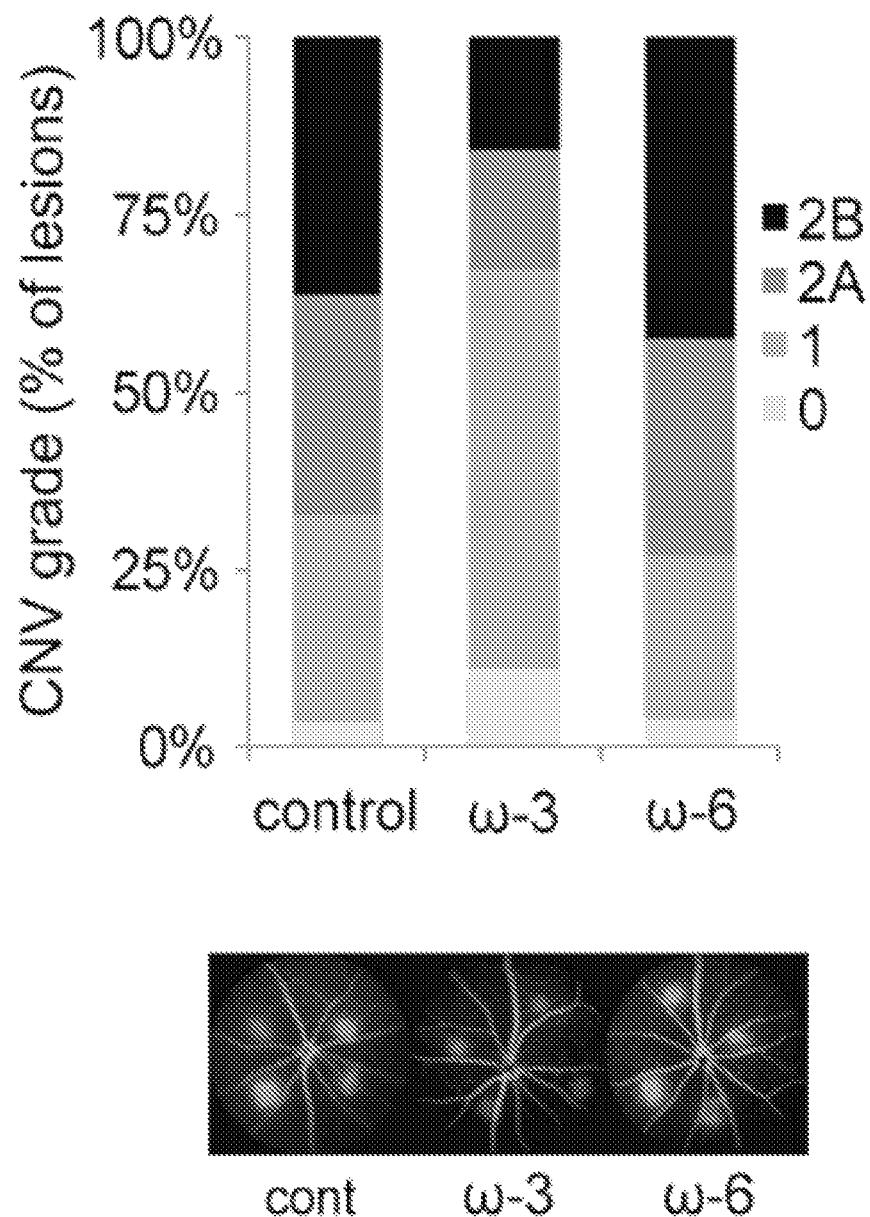

Example 2—sEH Null Mice Promote Metabolism of LCPUFAs to their Active Eicosanoids in Endothelial Cells Soluble epoxide hydrolase (sEH), an enzyme that functions downstream of the CYP pathway, metabolizes bioactive fatty acids derived from the primary LCPUFAs into less bioactive diols. FIGS. 2A-2C show: (A, B) Lesion size at 7 d after CNV induction was assessed by staining of choroidal flat-mount preparations with fluorescent isolectin B4 (A), and cross-sectional area of lesions was quantified by SD-OCT (demarcated by circling)(B), for sEH null mice fed a control diet (n=49 lesions, respectively), ω-3 LCPUFAs enriched diet (n=57 lesions, respectively), or ω-6 LCPUFAs enriched diet (n=50 lesions, respectively) beginning 2 weeks before laser photocoagulation. sEH null mice lack expression of sEH, an enzyme that degrades CYP-derived fatty acid metabolites into less bioactive diols. ω-3 LCPUFAs decreased CNV size in choroidal flatmount and OCT section compared to the control diet and ω-6 LCPUFAs diet groups. Data are presented as means±SEM. *P<0.05. Scale bars: 100 μm. (C) Fluorescein leakage in CNV lesions was graded at 7 d after CNV induction in sEH null mice fed a control diet (n=49 lesions), ω-3 LCPUFAs enriched diet (n=57 lesions), or ω-6 LCPUFAs enriched diet (n=50 lesions) beginning 2 weeks before laser photocoagulation. ω-3 LCPUFAs attenuated fluorescein leakage from the CNV lesions compared to the control diet and ω-6 diet groups.

The loss of sEH had a similar effect as the overexpression of the monooxygenase CYP2C8 in endothelial cells. The size of CNV lesions 7 days after laser induction was significantly decreased in sEH null mice fed a diet enriched with EPA and DHA compared to mice on a control diet, as assessed in choroidal flatmounts and OCT cross-sectional images. The severity of vascular leakage in CNV lesions was also significantly decreased in sEH null mice fed a diet enriched with EPA and DHA compared to mice on a control diet.

Example 3—Tie2-hsEH Mice Overexpress sEH Enzyme in Endothelial Cells (Promoting Breakdown of CYP-Derived Eicosanoids into Less Bioactive Metabolites)

Tie2-hsEH mice overexpress the sEH enzyme in endothelial cells, which rapidly breakdown CYP-derived fatty acids into less bioactive diols.

Figure 3A:
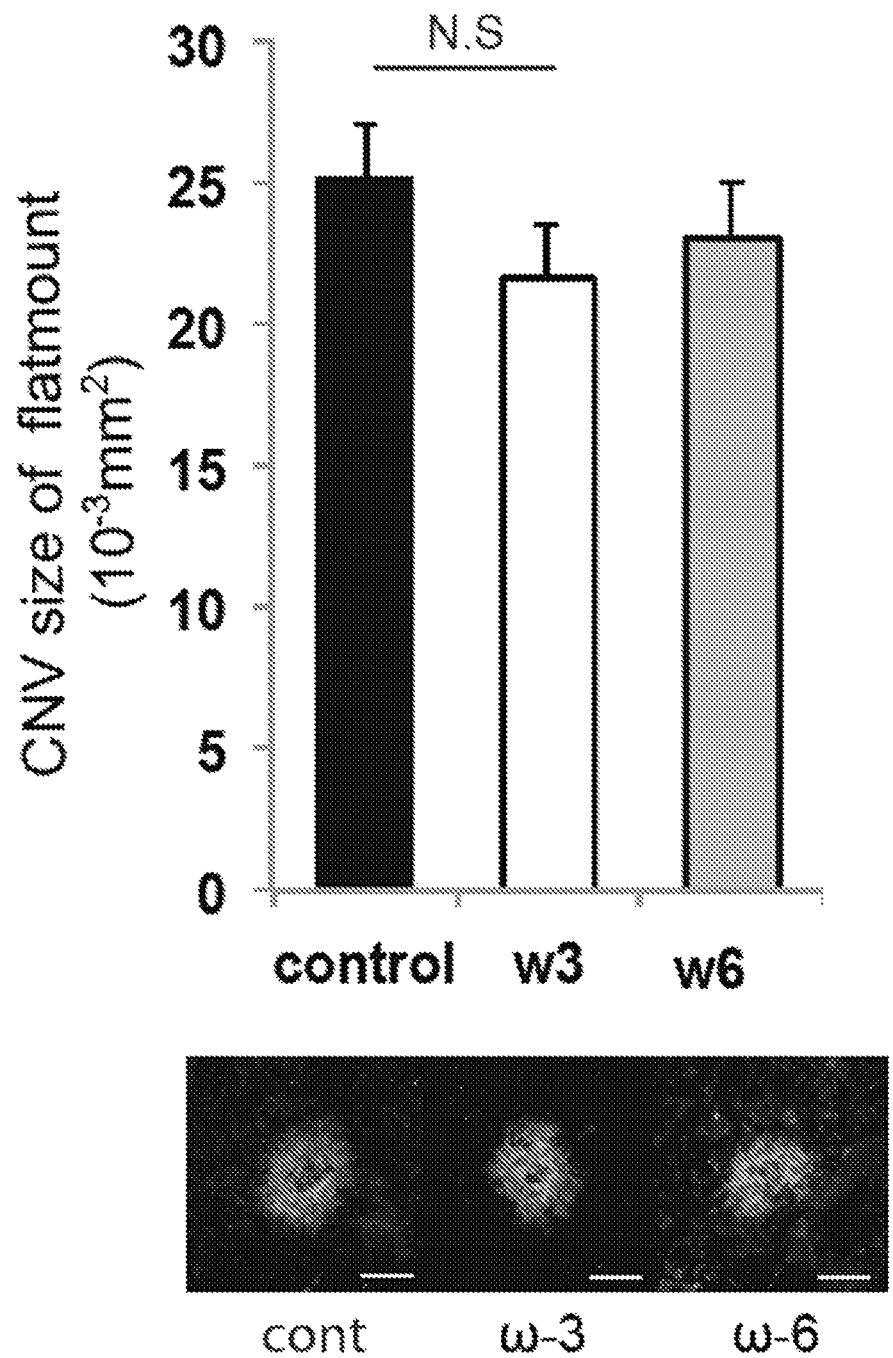
FIGS. 3A-3C. Lesion size at 7 d after CNV induction was assessed by staining of choroidal flat-mount preparations with fluorescent isolectin B4 (FIG. 3A), and cross-sectional area of lesions was quantified by SD-OCT (demarcated by circling) (FIG. 3B), for Tie2-sEH-Tg mice fed a control diet (n=21 lesions, respectively), ω-3 LCPUFAs enriched diet (n=44 lesions, respectively), or ω-6 LCPUFAs enriched diet (n=39 lesions, respectively) beginning 2 weeks before laser photocoagulation.
Figure 3B:
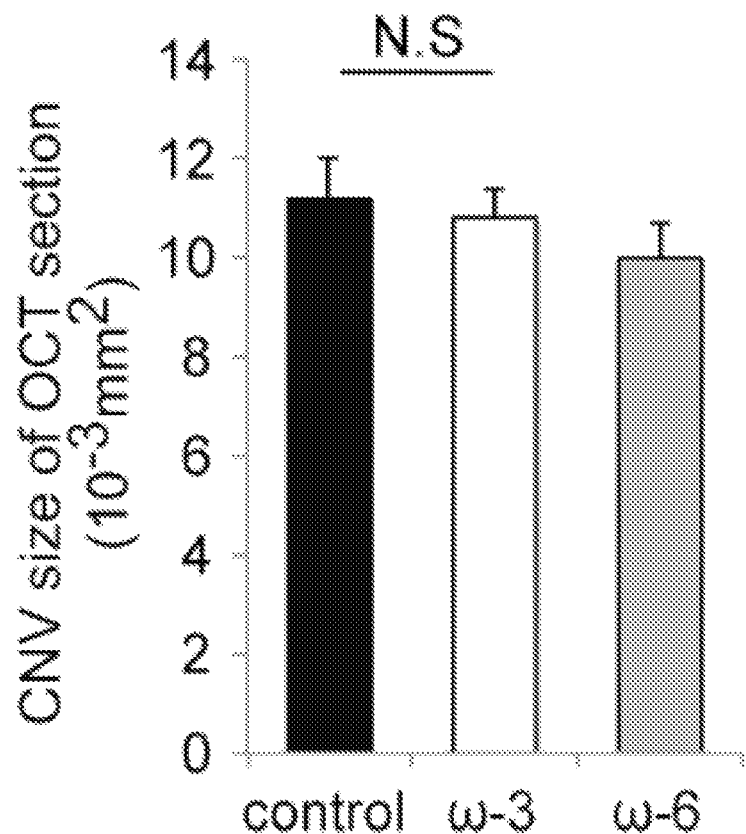
Figure 3B:
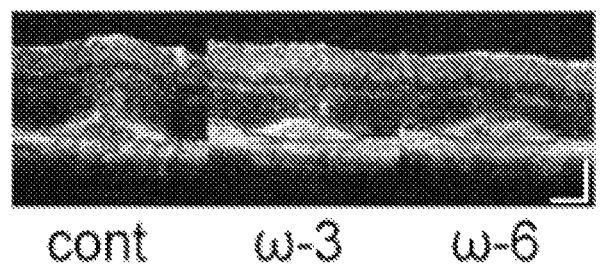
Figure 3C:
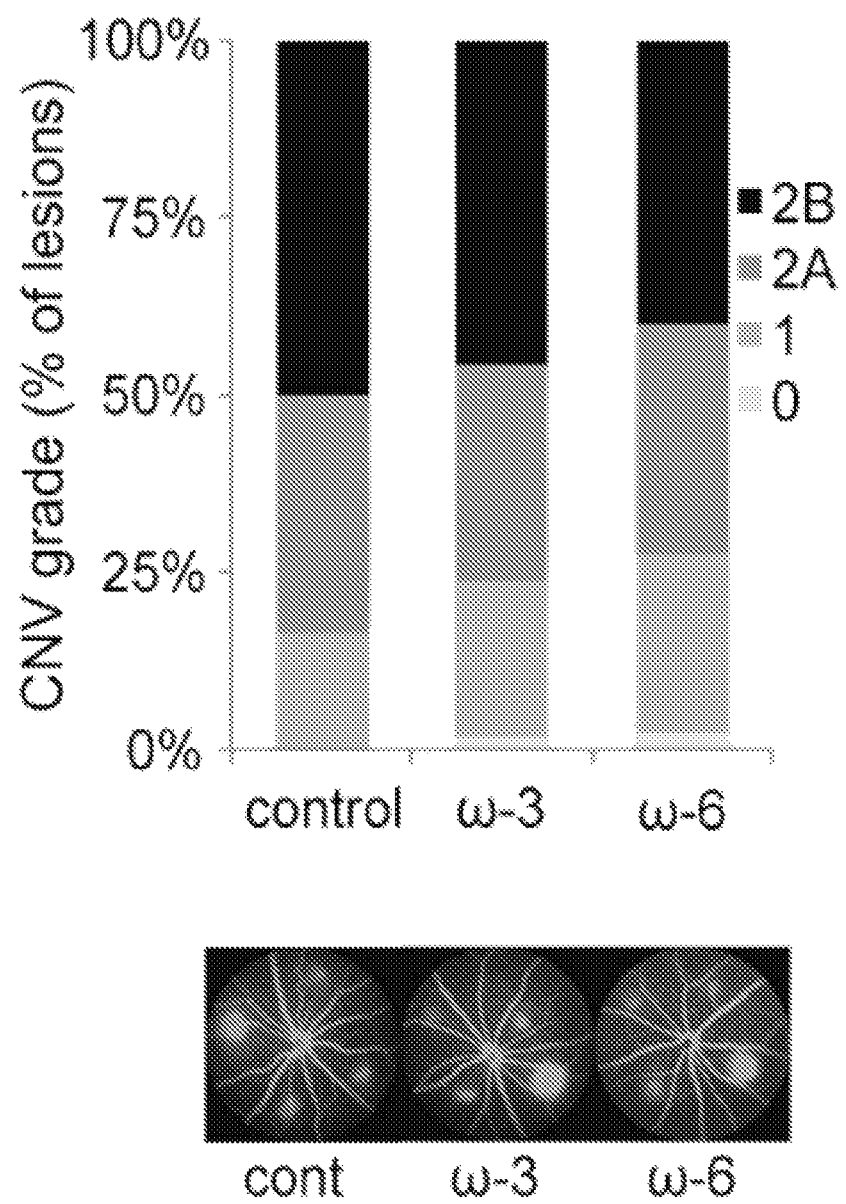

FIGS. 3A-3C show that dietary intake of ω-3 LCPUFAs in Tie2-sEH-Tg mice does not affect CNV: (A, B) Lesion size at 7 d after CNV induction was assessed by staining of choroidal flat-mount preparations with fluorescent isolectin B4 (A), and cross-sectional area of lesions was quantified by SD-OCT (demarcated by circling) (B), for Tie2-sEH-Tg mice fed a control diet (n=21 lesions, respectively), ω-3 LCPUFAs enriched diet (n=44 lesions, respectively), or ω-6 LCPUFAs enriched diet (n=39 lesions, respectively) beginning 2 weeks before laser photocoagulation. Despite sEH up-regulation in these Tie2-sEH-Tg mice, there were no significant differences in CNV size in choroidal flatmount and OCT section among the three diet groups. Data are presented as means±SEM. N.S: not significant. Scale bars: 100 μm. (C) Fluorescein leakage in CNV lesions was graded at 7 d after CNV induction in Tie2-sEH-Tg mice fed a control diet (n=21 lesions), ω-3 LCPUFAs enriched diet (n=44 lesions), or ω-6 LCPUFAs enriched diet (n=39 lesions) beginning 2 weeks before laser photocoagulation. The severity of fluorescein leakage did not change among the three groups.

Figure 4A:
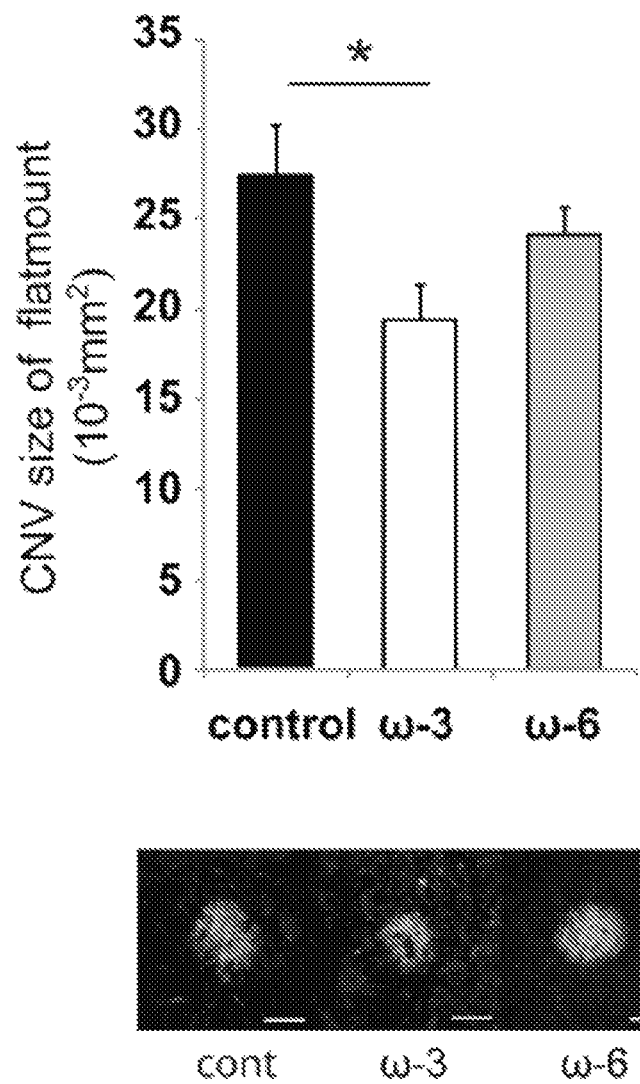
FIGS. 4A-4C. Lesion size at 7 d after CNV induction was assessed by staining of choroidal flat-mount preparations with fluorescent isolectin B4 (FIG. 4A), and cross-sectional area of lesions was quantified by SD-OCT (demarcated by circling) (FIG. 4B), for C57BL/6J background mice (common inbred strain of laboratory mouse) fed a control diet (n=20 lesions, respectively), ω-3 LCPUFAs enriched diet (n=26 lesions, respectively), or ω-6 LCPUFAs enriched diet (n=40 lesions, respectively) beginning 2 weeks before laser photocoagulation.
Figure 4B:
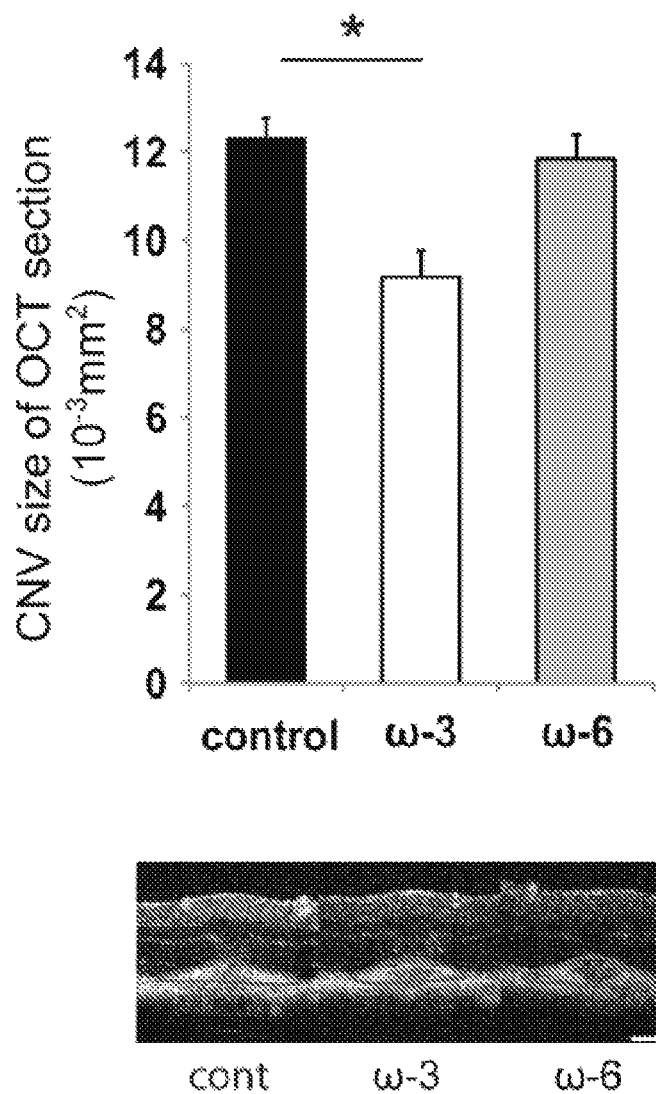
Figure 4C:
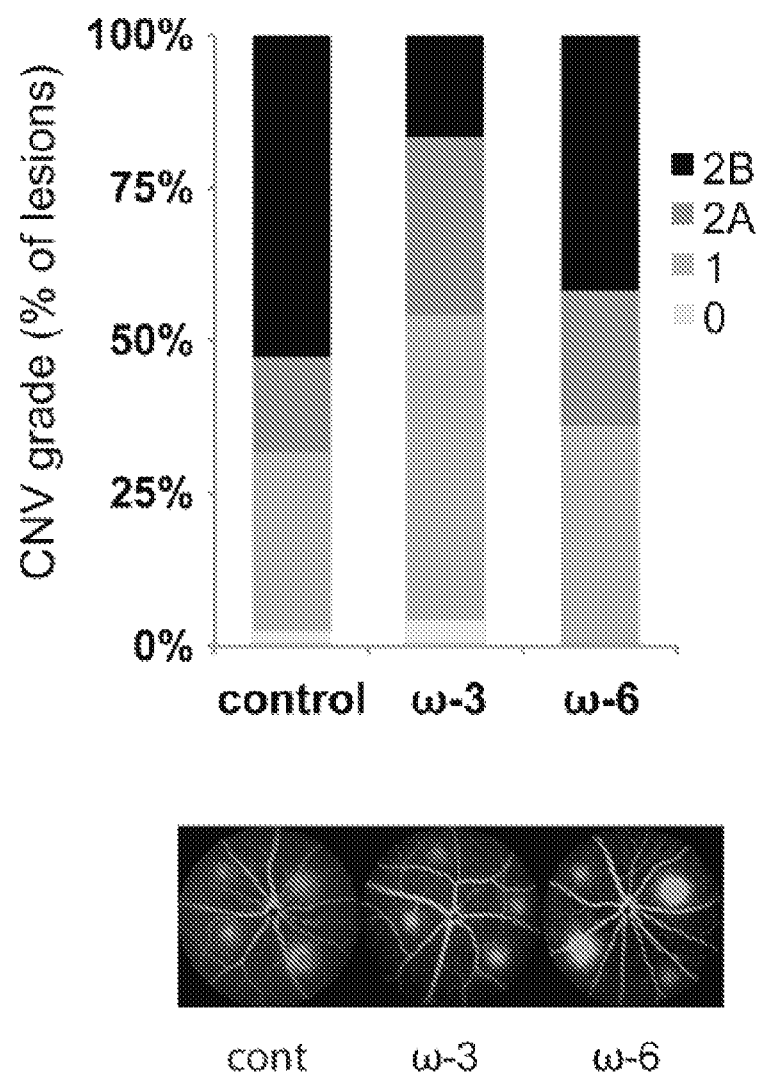
Figure 5A:
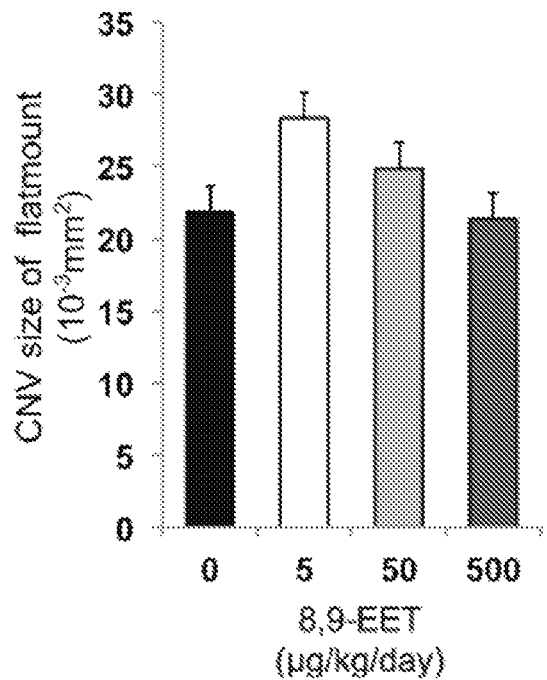
FIGS. 5A-5I. Lesion size at 7 d after CNV induction was assessed by staining of choroidal flat-mount preparations with fluorescent isolectin B4 (FIGS. 5A-5C), and cross-sectional area of lesions was quantified by SD-OCT (FIGS. 5D-5F), for C57BL/6 mice administered 8,9-EET (FIGS. 5A, 5D), 11,12-EET (FIGS. 5B, 5E), and 14,15-EET (FIGS. 5C, 5F) once a day immediately after laser photocoagulation.
Figure 5B:
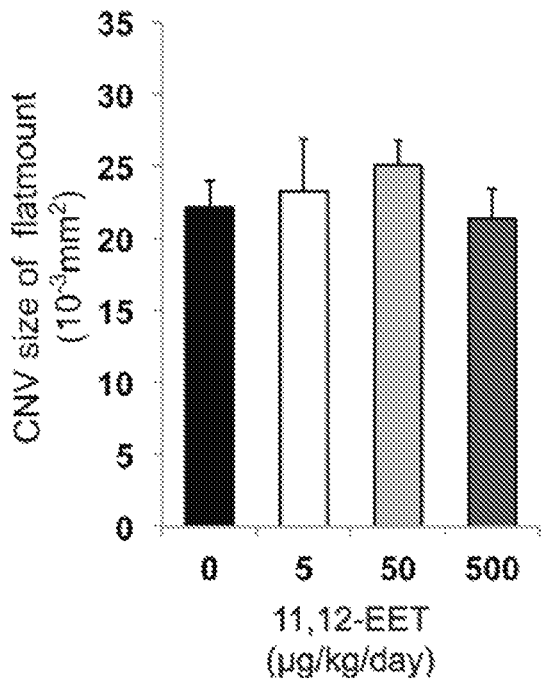
Figure 5C:
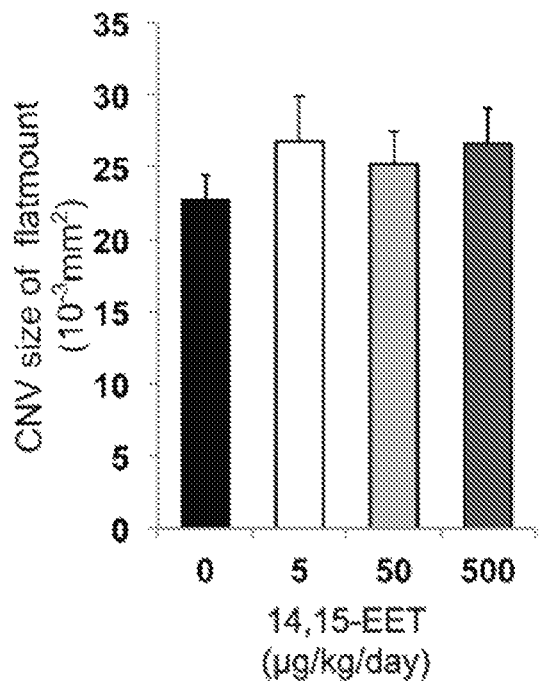
Figure 5D:
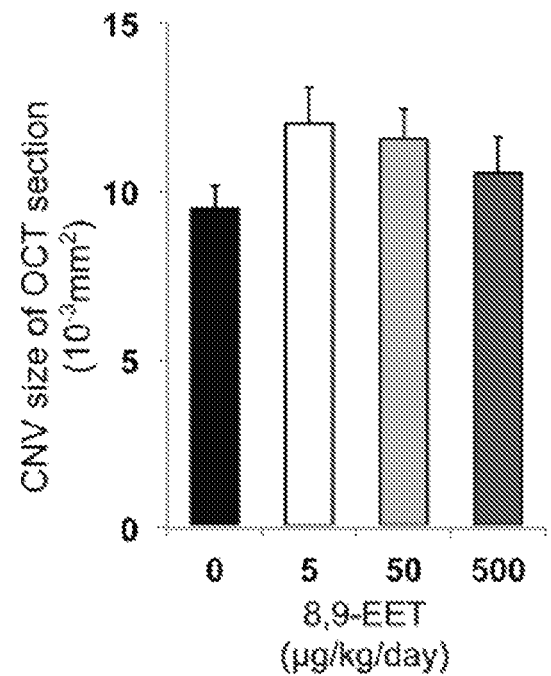
Figure 5E:
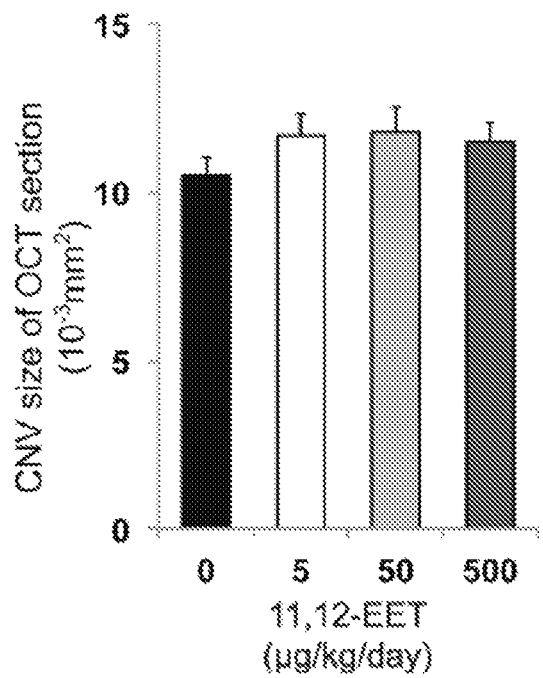
Figure 5F:
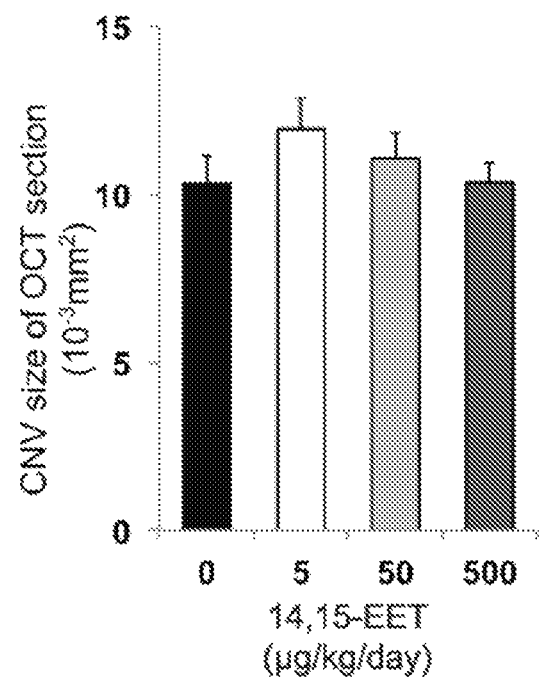
Figure 5G:
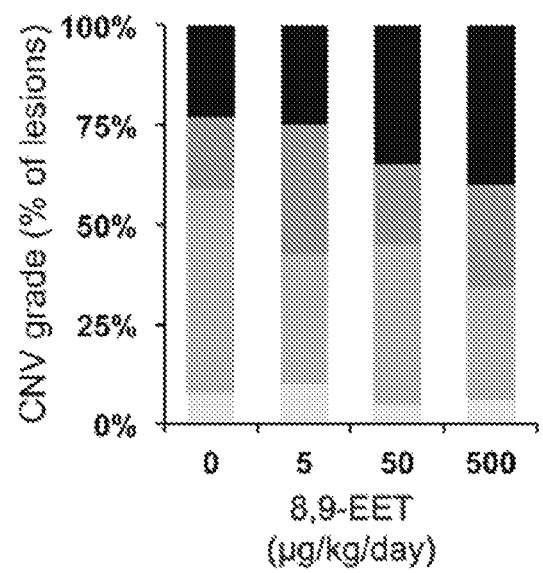
Figure 5H:
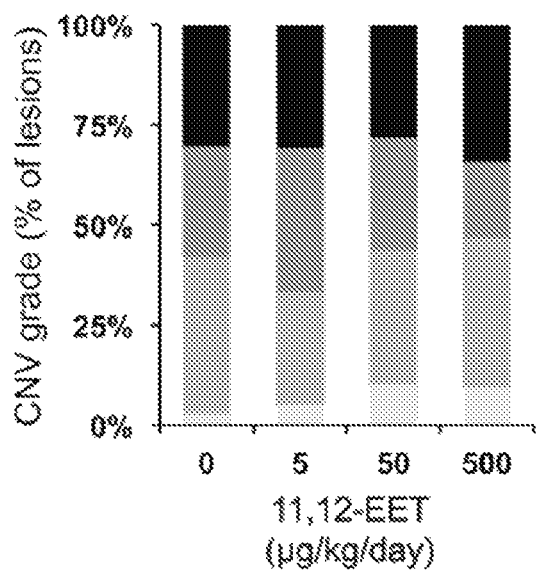
Figure 5I:
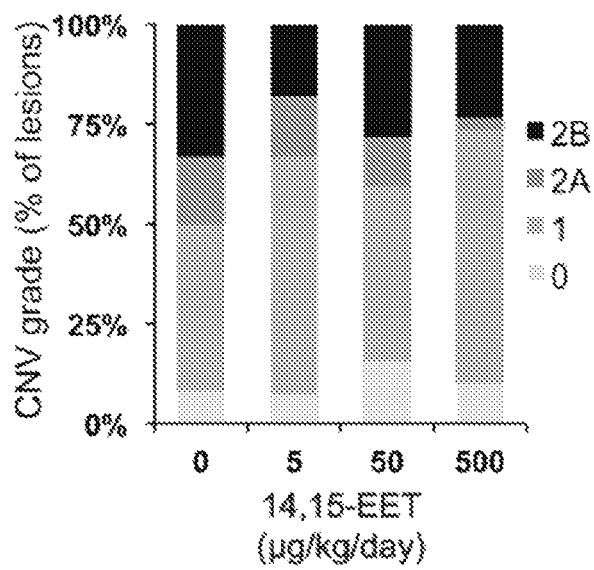

FIGS. 4A-4C show results of dietary intake of ω-3 LCPUFAs in C57BL/6 background mice attenuates CNV: (A, B) Lesion size at 7 d after CNV induction was assessed by staining of choroidal flat-mount preparations with fluorescent isolectin B4 (A), and cross-sectional area of lesions was quantified by SD-OCT (demarcated by circling)(B), for C57BL/6J background mice fed a control diet (n=20 lesions, respectively), ω-3 LCPUFAs enriched diet (n=26 lesions, respectively), or ω-6 LCPUFAs enriched diet (n=40 lesions, respectively) beginning 2 weeks before laser photocoagulation. ω-3 LCPUFAs decreased CNV size in choroidal flatmounts and OCT sections compared to control diet and ω-6 LCPUFAs diet groups. Data are presented as means±SEM. *P<0.05. Scale bars: 100 μm. (C) Fluorescein leakage in CNV lesions was graded at 7 d after CNV induction in C57BL/6 background mice fed a control diet (n=20 lesions), ω-3 LCPUFAs enriched diet (n=26 lesions), or ω-6 LCPUFAs enriched diet (n=40 lesions) beginning 2 weeks before laser photocoagulation. ω-3 LCPUFAs attenuated fluorescein leakage from the CNV lesions compared to the control diet and ω-6 diet groups.

When Tie2-hsEH mice were fed a diet enriched with EPA and DHA, the protective effects against CNV seen with this diet were lost. When Tie2-hsEH mice were fed ω-3 diet, the protective effects against CNV obtained from the ω-3 diet were reversed in choroidal flatmount (FIG. 3A), OCT cross-sectional image (FIG. 3B), and the severity of vascular leakage (FIG. 3C). Littermate control animals, on a C57BL/6 background, confirmed that a diet enriched with EPA and DHA was still protective against increased CNV disease severity (FIGS. 4A-4C). The protective effect observed from CYP-derived fatty acids of EPA and DHA is lost by their metabolic degradation.

Example 4—EETs Did not Alter CNV Size or Severity Compared to their Respective Base Line Controls Feeding a diet enriched with AA in CYP Tg Mice and administration of EETs in C57BL/6 mice did not alter CNV size or severity compared to their respective base line controls. See FIGS. 5A-5I.

FIGS. 5A-5I show that CYP-derived ω-6 eicosanoids do not affect CNV: (A-F) Lesion size at 7 d after CNV induction was assessed by staining of choroidal flat-mount preparations with fluorescent isolectin B4 (A-C), and cross-sectional area of lesions was quantified by SD-OCT (D-F), for C57BL/6 mice administered 8,9-EET (A, D), 11,12-EET (B, E), and 14,15-EET (C, F) once a day immediately after laser photocoagulation. Data are presented as means±SEM. (G-I) Fluorescein leakage in CNV lesions was graded at 7 d after CNV induction in C57BL/6 mice administered 8,9-EET (G), 11,12-EET (H), and 14,15-EET (I). n=55-63 lesions per experimental group.

AA-derived EETs do not lead to progression of disease severity but do not affect CNV, while CYP-derived EEQs and EDPs confer protection.

Example 5—Plasma Concentrations of 17,18-EEQ and 19,20-EDP in Transgenic Mice

Figure 6A:
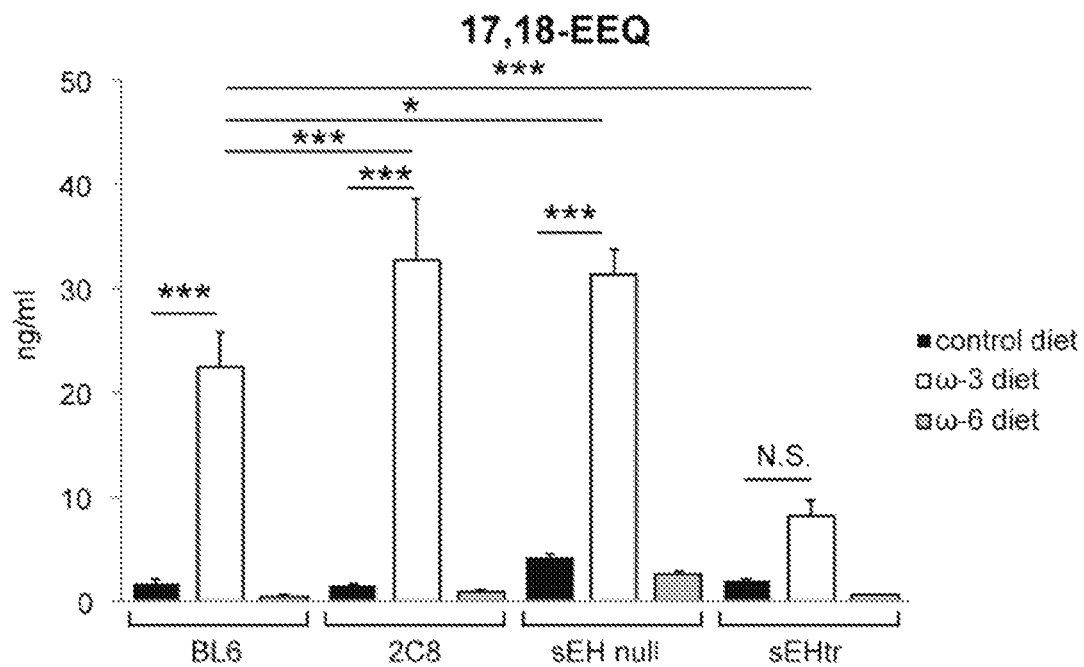
FIGS. 6A and 6B show plasma profile of CYP-derived fatty acids in Cytochrome P (CYP) enzyme genetically modified (Tg) mice: the plasma levels of 17,18-EEQ (FIG. 6A) and 19,20-EDP (FIG. 6B) in CYP-Tg mice (C57BL/6 background [abbreviated as BL6], Tie2-CYP2C8-Tg [abbreviated as 2C8], sEH null, and Tie2-sEH-Tg [abbreviated as sEHtr], respectively) were determined at 7 d after CNV induction by LC/MS/MS.
Figure 6B:
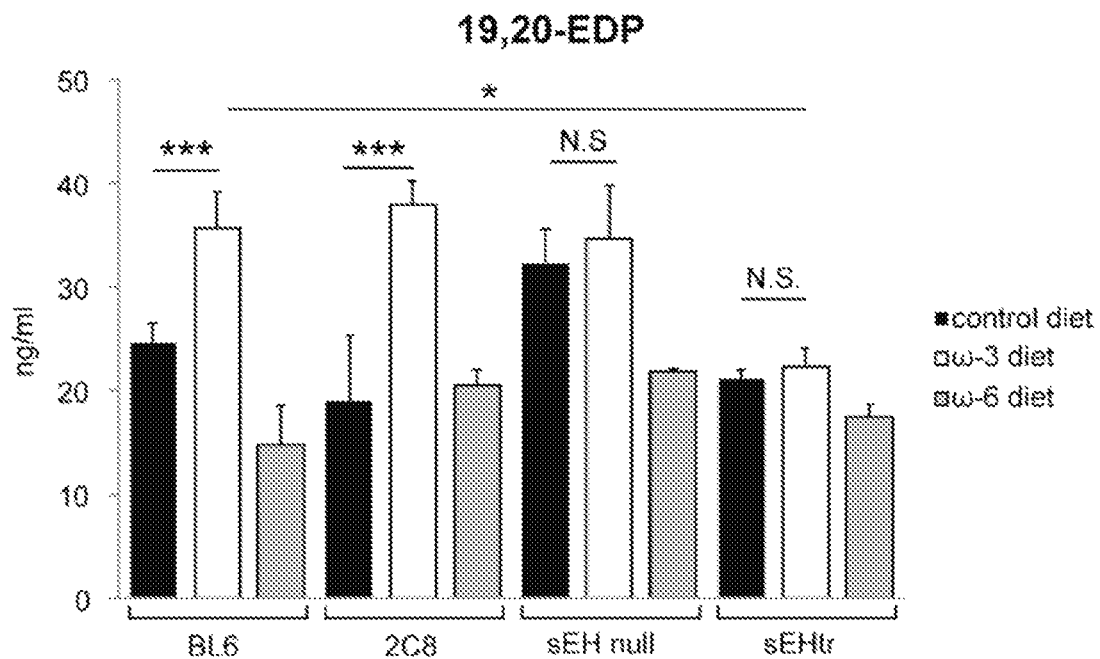

Plasma concentrations of 17,18-EEQ and 19,20-EDP was measured in animals on experimental diets 7 days after laser induction of CNV. LC-MS/MS revealed that EPA-derived 17,18-EEQ was significantly increased in both Tie2-CYP2C8-Tg and sEH null mice fed an EPA and DHA enriched diet compared to their respective strain-matched mice fed a control diet (FIG. 6A). DHA-derived 19,20-EDP was significantly increased in Tie2-CYP2C8-Tg mice fed an EPA and DHA enriched diet compared to Tie2-CYP2C8-Tg mice fed a control diet (FIG. 6B). The plasma levels of 17,18-EEQ in Tie2-CYP2C8-Tg mice and sEH null mice on an EPA and DHA enriched diet were significantly up-regulated compared to C57BL/6 mice on an EPA and DHA enriched diet. In contrast, Tie2-sEH-Tg mice on an EPA and DHA enriched diet did not exhibit a significant increase in either 17,18-EEQ or 19,20-EDP compared to Tie2-sEH-Tg mice on a control diet (FIGS. 6A, 6B).

FIGS. 6A and 6B show plasma profile of CYP-derived fatty acids in CYP enzyme Tg mice: the plasma levels of 17,18-EEQ (A) and 19,20-EDP (B) in CYP-Tg mice (C57BL/6 background [abbreviated as BL6], Tie2-CYP2C8-Tg [abbreviated as 2C8], sEH null, and Tie2-sEH-Tg [abbreviated as sEHtr], respectively) were determined at 7 d after CNV induction by LC/MS/MS. Tie2-CYP2C8-Tg mice overexpress the monooxygenase CYP2C8 in endothelial cells, which promotes the metabolism of the primary LCPUFAs to their active downstream fatty acid metabolites (e.g., 17,18-EEQ and 19,20-EDP). sEH null mice lack expression of sEH, an enzyme that degrades these CYP-derived fatty acid metabolites into less bioactive diols. Conversely, Tie2-sEH-Tg mice overexpress sEH. Mice were fed either a ω-3 LCPUFAs enriched diet, ω-6 LCPUFAs enriched diet, or control diet. Data are presented as means±SEM. *P<0.05 P<0.01 *P<0.001. N.S.: not significant. n=3-4 mice per experimental group.

17,18-EEQ and 19,20-EDP are the primary effector metabolites in CNV disease resolution (not the COX or LOX metabolites), and the protective effect of an enriched EPA and DHA diet is lost with over-expression of sEH, an enzyme that degrades these bioactive fatty acid metabolites.

Example 6—Administration of C21 Reduced CNV Size

Figure 21:
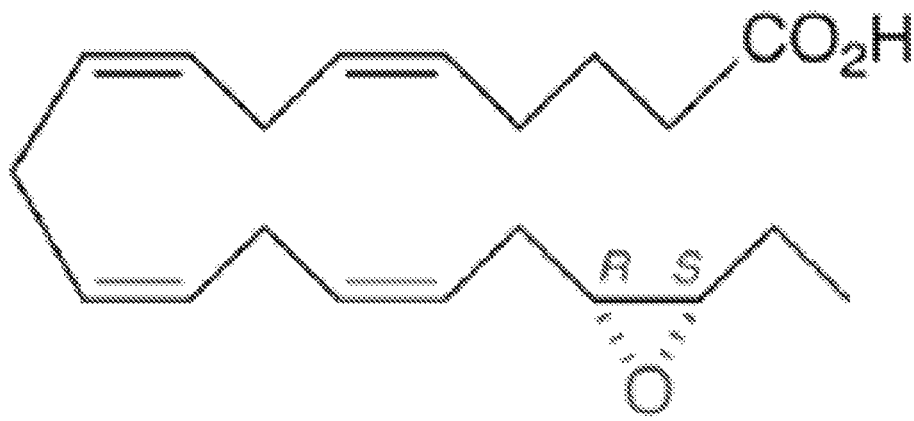
FIG. 21 shows a chemical structure of 17(R),18(S)-EEQ.
Figure 22:
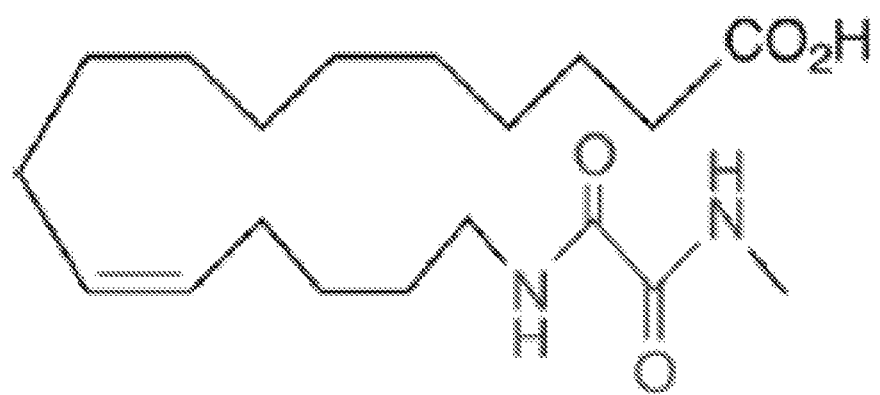
FIG. 22 shows chemical structure of compound C21.

Stable analog of 17,18-EEQ (compound C21, (Z)-16-(2-(methylamino)-2-oxoacetamido)hexadec-11-enoic acid) having the following chemical structure:

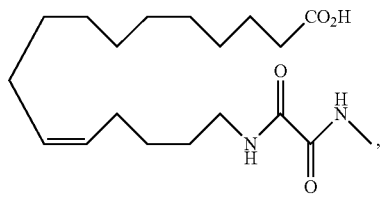 [SMILES: CNC(=O)C(=O)NCCCC/C=C\CCCCCCCCCC(=O)O]

contains oxamide functional group (as opposed to the epoxide group in 17, 18-EEQ) and maintains its potent bioactive functions but is unable to be degraded by sEH. See Falck J R et al. 17(R),18(S)-epoxyeicosatetraenoic acid, a potent eicosapentaenoic acid (EPA) derived regulator of cardiomyocyte contraction: structure-activity relationships and stable analogues. *J Med Chem,* 2011, 54(12), 4109-4118. FIG. 21 depicts chemical structure of 17R,18S-EEQ, while FIG. 22 depicts chemical structure of the stable analog C21.

Figure 7A:
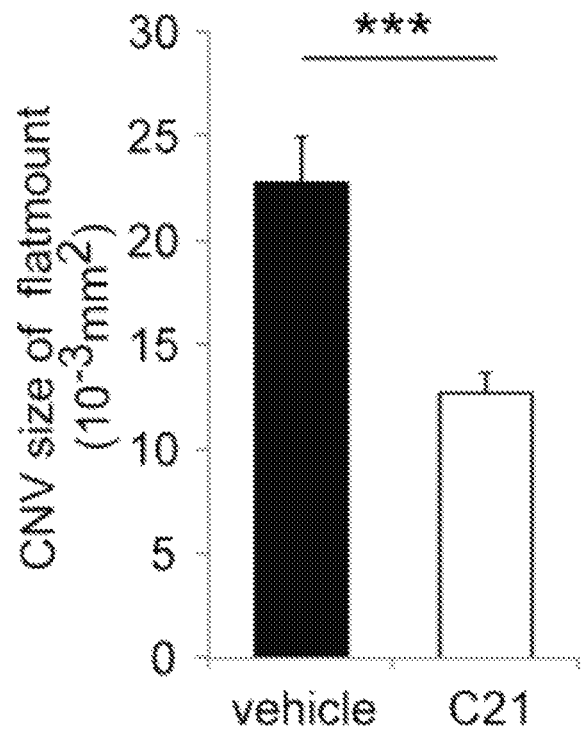
FIGS. 7A-7C. Lesion size at 7 d after CNV induction was assessed by staining of choroidal flat-mount preparations with fluorescent isolectin B4 (FIG. 7A), and cross-sectional area of lesions was quantified by SD-OCT (FIG. 7B), for C57BL/6 mice administered control vehicle or C21 (50 µg/kg/day) once a day immediately after laser photocoagulation.
Figure 7B:
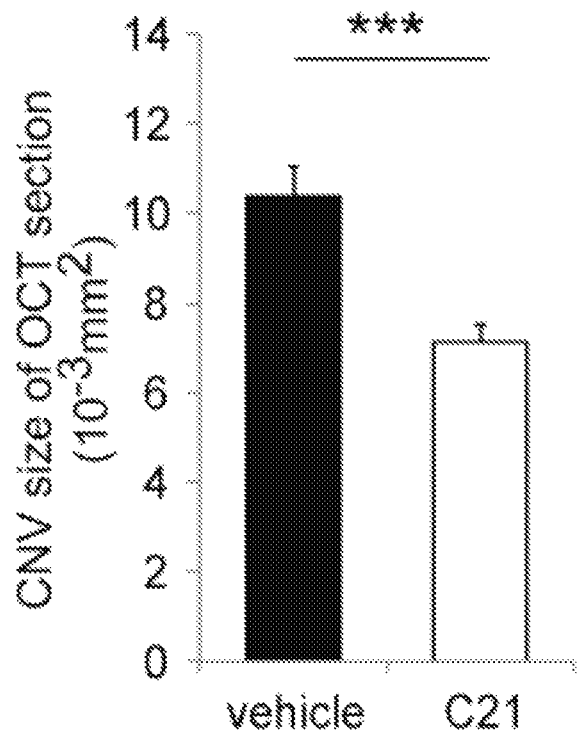
Figure 7C:
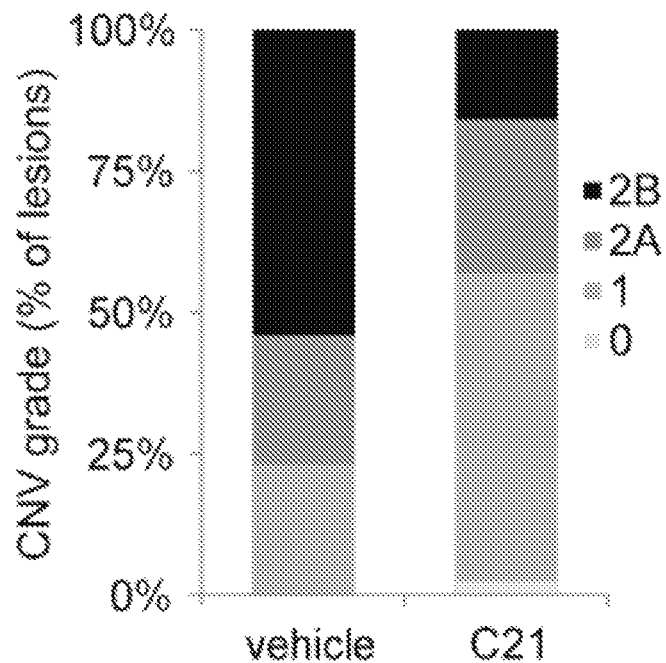

FIGS. 7A-7C show that administration of C21 in C57BL/6 mice attenuates CNV: (A, B) Lesion size at 7 d after CNV induction was assessed by staining of choroidal flat-mount preparations with fluorescent isolectin B4 (A), and cross-sectional area of lesions was quantified by SD-OCT (B), for C57BL/6 mice administered control vehicle or C21 (50 µg/kg/day) once a day immediately after laser photocoagulation. Data are presented as means±SEM. ***P<0.001. n=37-48 lesions per experimental group. (C) Fluorescein leakage in CNV lesions was graded at 7 d after CNV induction in C57BL/6 mice administered control vehicle or C21 (50 µg/kg/day) once a day immediately after laser photocoagulation. n=37-48 lesions per experimental group.

Figure 8A:
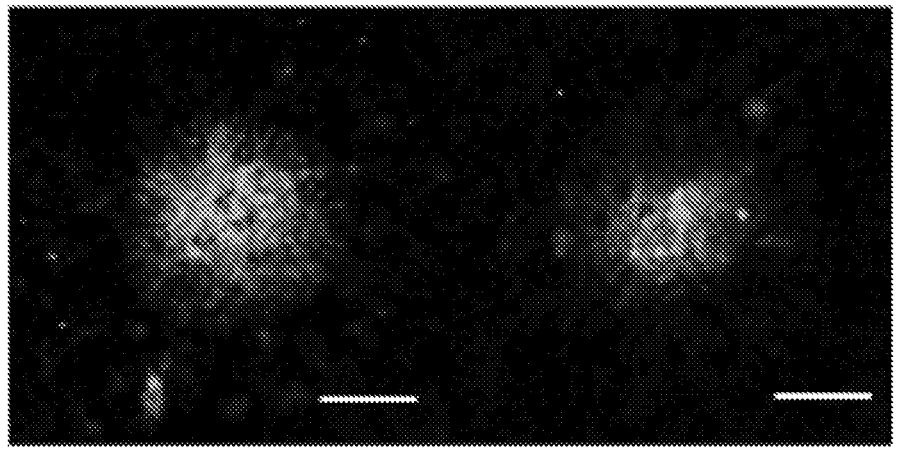
FIGS. 8A-8C. CNV lesions at 7 d after laser photocoagulation were assessed by staining of choroidal flat-mount with fluorescent isolectin B4 (FIG. 8A), cross-sectional area of lesions quantified by SD-OCT (demarcated by circling) (FIG. 8B), and fluorescein angiography (FIG. 8C), for C57BL/6J mice administered control vehicle or C21 (50 µg/kg/day) once a day immediately after laser photocoagulation.
Figure 8B:
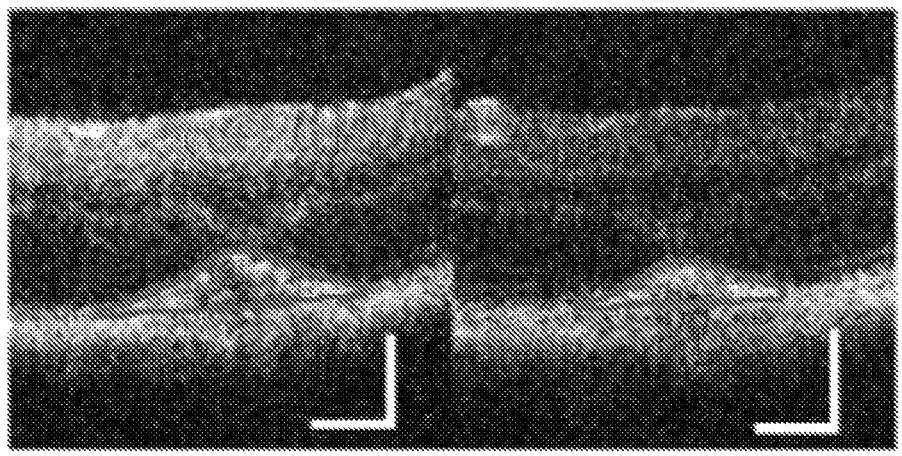
Figure 8C:
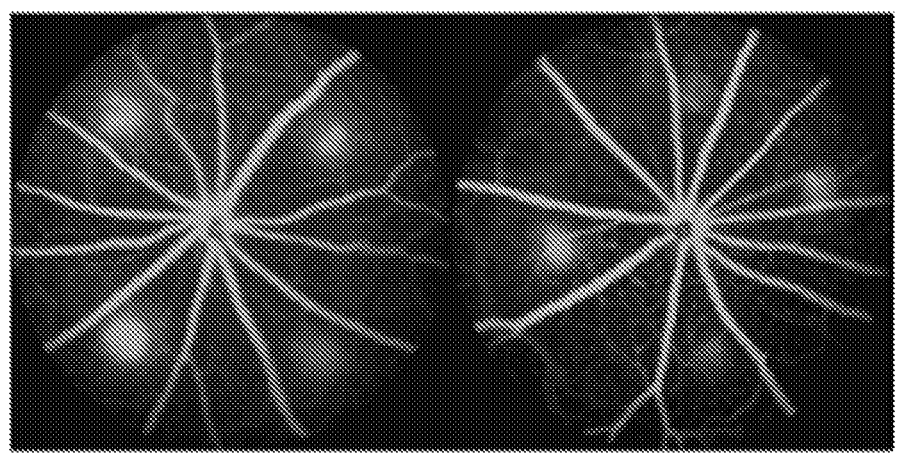
Figure 9A:
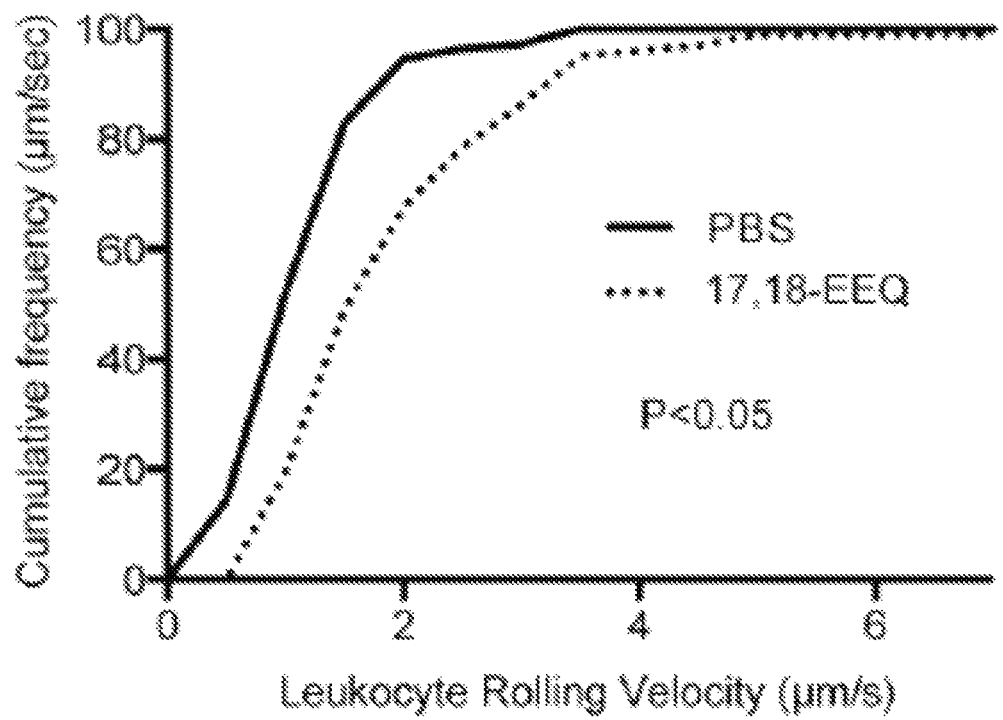
FIGS. 9A-9I. Cumulative frequency of leukocyte rolling velocity in a chamber coated with both P-selectin and intercellular adhesion molecule 1 (ICAM-1) was assessed at day 3 after CNV induction, mice were injected by intraperitoneal injection (i.p.) with (FIG. 9A) 17,18-EEQ (50 µg/kg/day), (FIG. 9B) 19,20-EDP (50 µg/kg/day), or PBS daily beginning immediately after CNV induction.
Figure 9B:
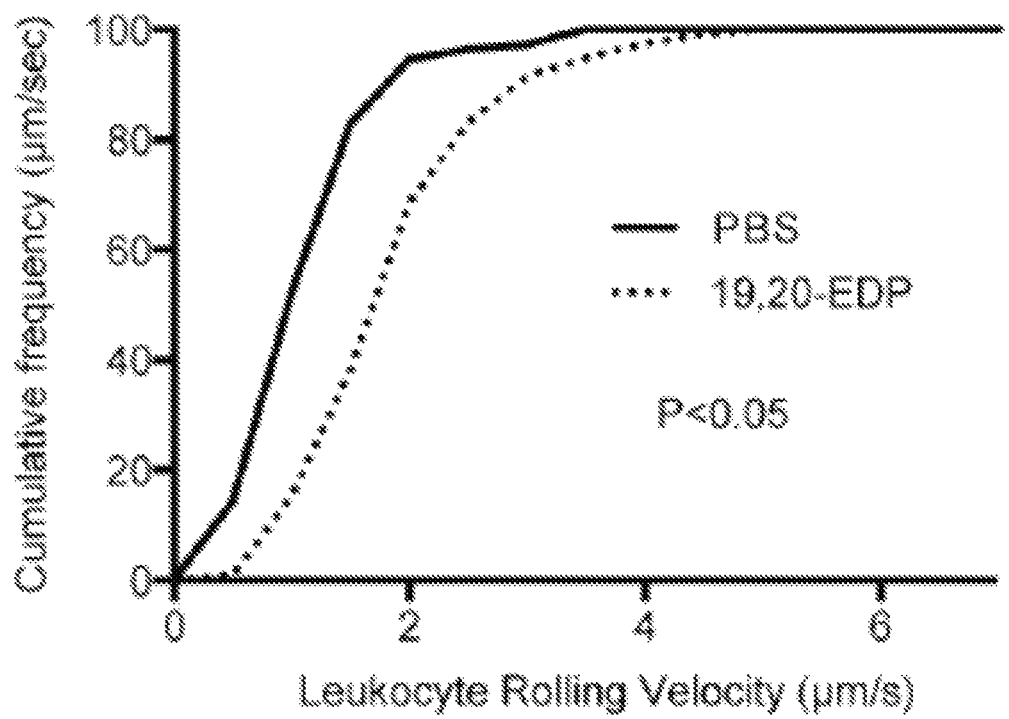
Figure 9C:
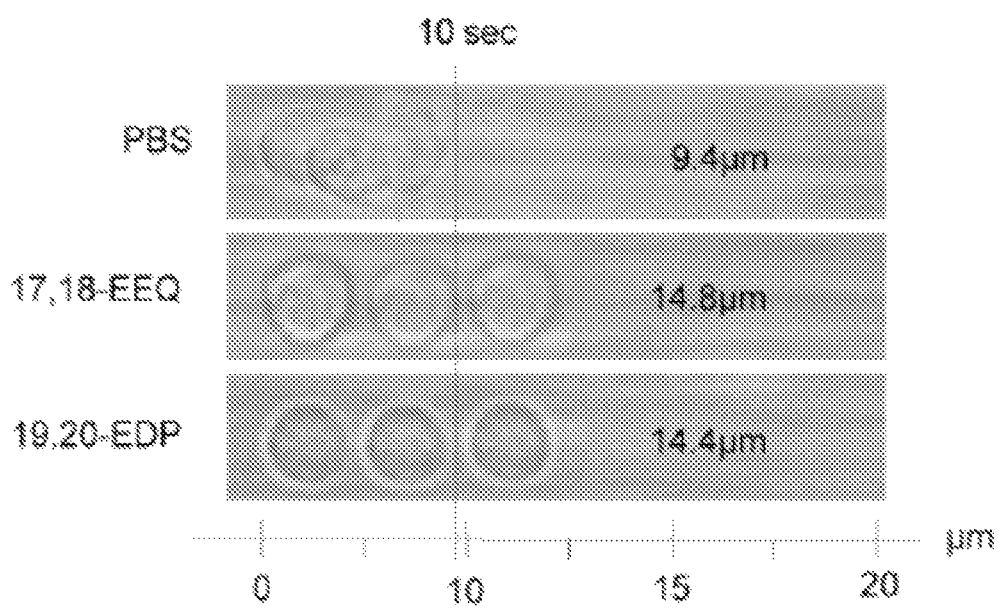
Figure 9D:
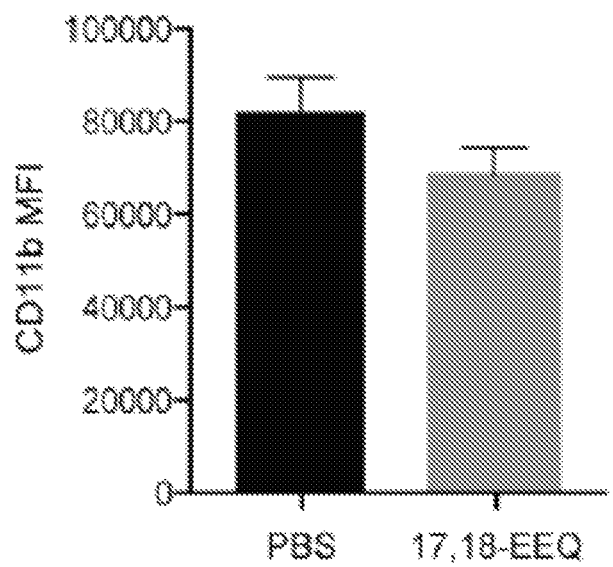
Figure 9E:
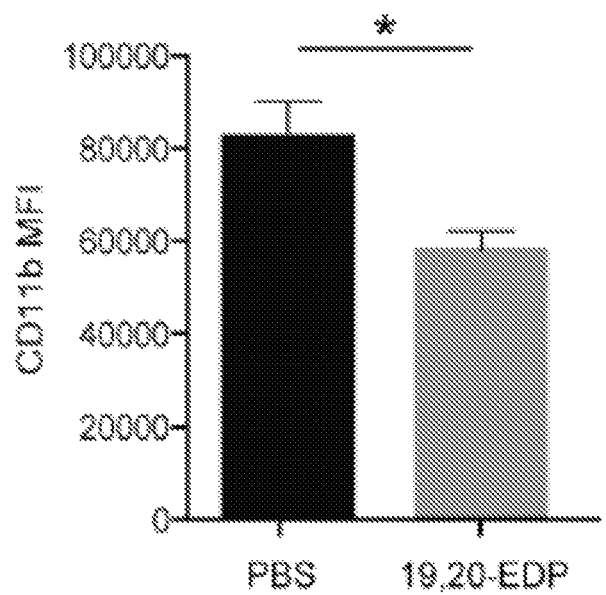
Figure 9F:
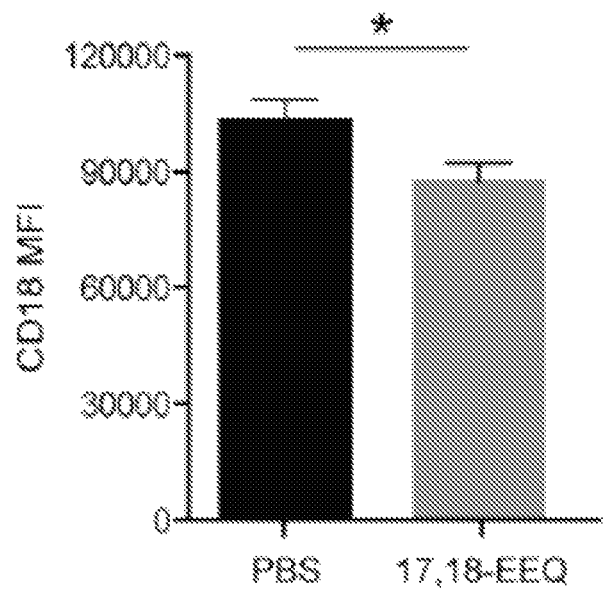
Figure 9G:
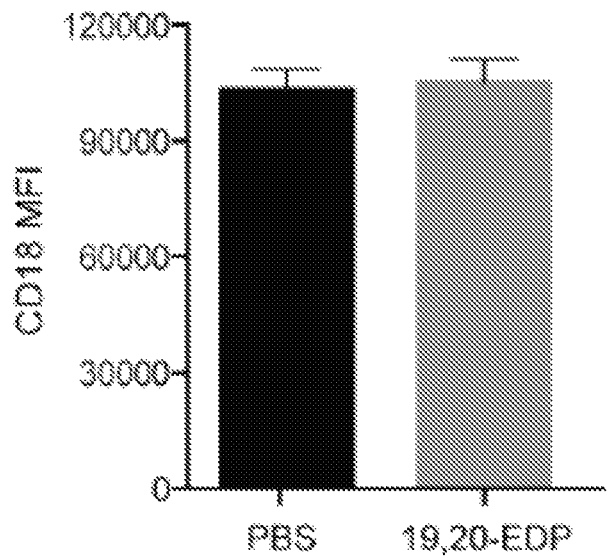
Figure 9H:
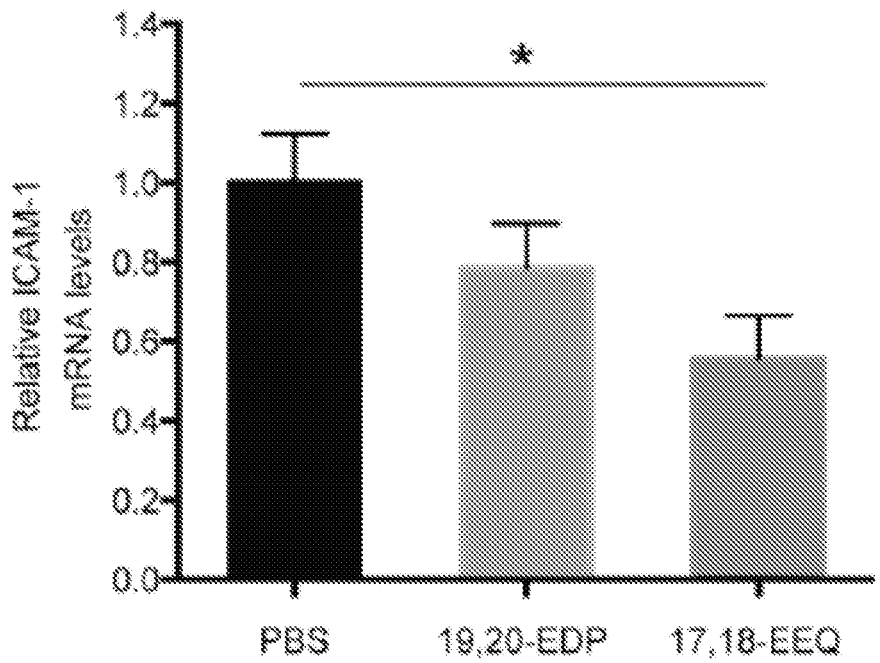
Figure 9I:
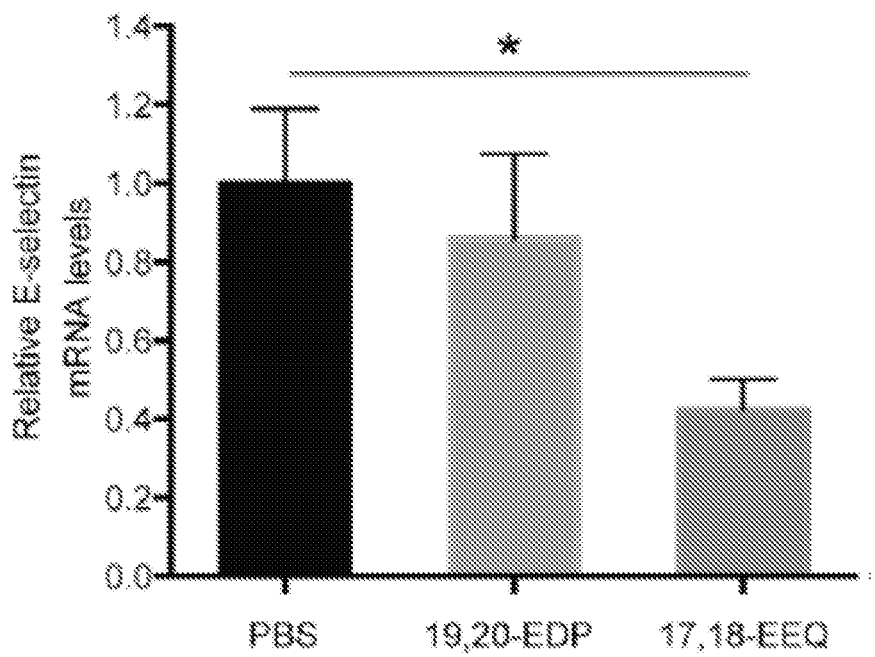
Figure 10A:
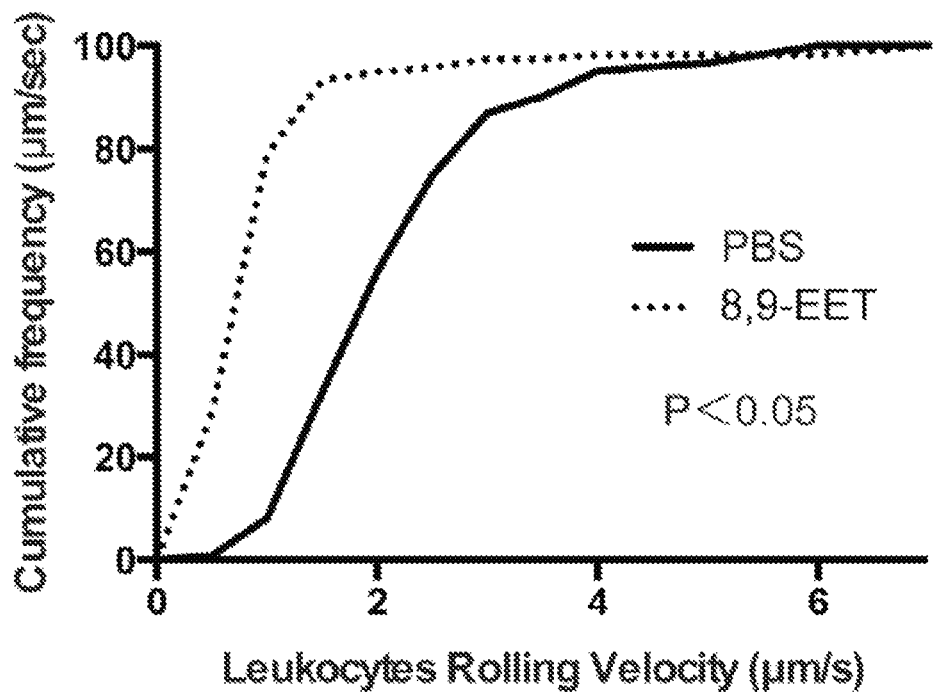
FIGS. 10A-10L. Cumulative frequency of leukocyte rolling velocity in a chamber coated with both P-selectin and ICAM-1 were assessed at day 3 after CNV induction, mice were injected i.p. with (FIG. 10A) 8,9-EET (50 µg/kg/day), (FIG. 10B) 11,12-EET (50 µg/kg/day), (FIG. 10C) 14,15-EET (50 µg/kg/day), or PBS daily beginning immediately after CNV induction.
Figure 10B:
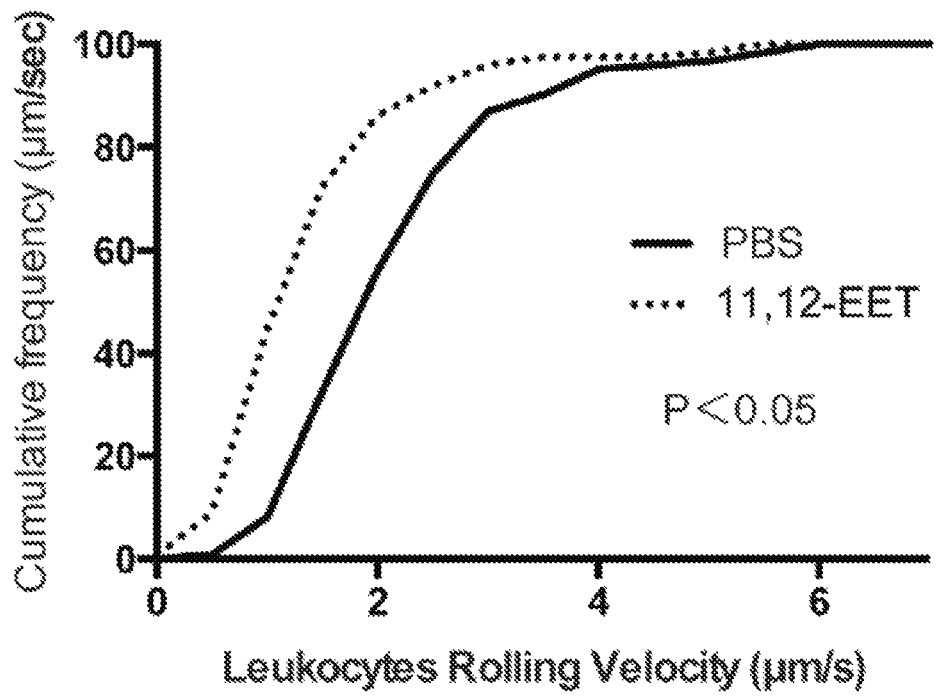
Figure 10C:
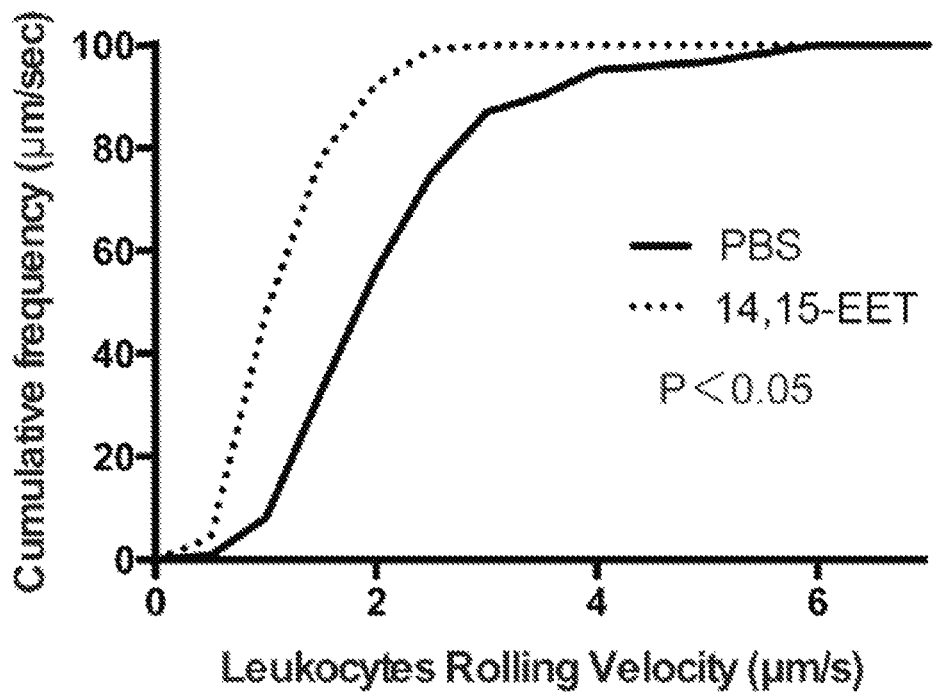
Figure 10D:
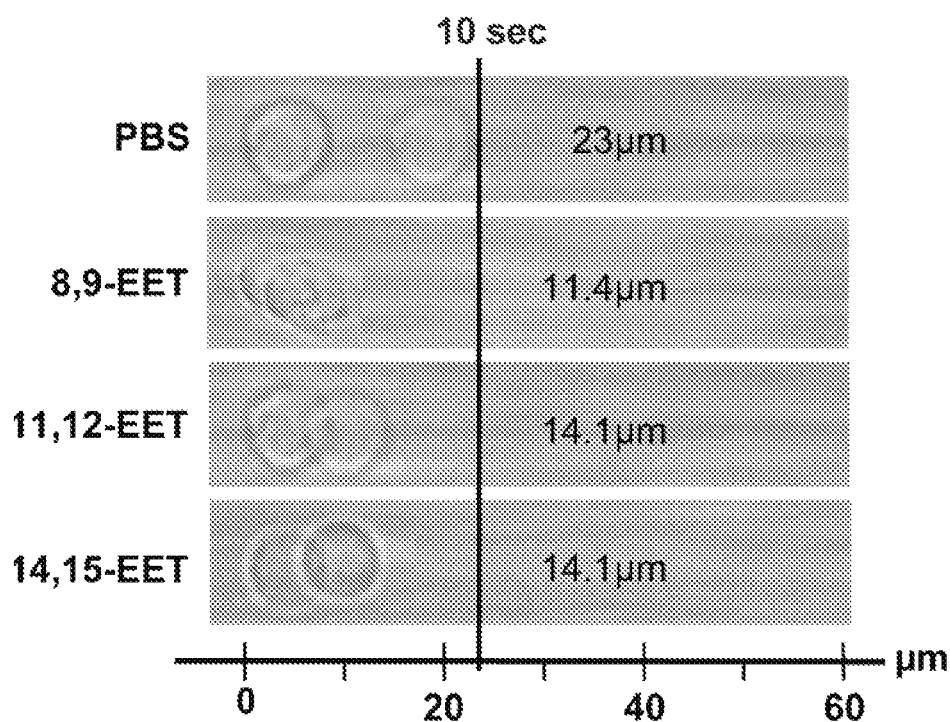
Figure 10E:
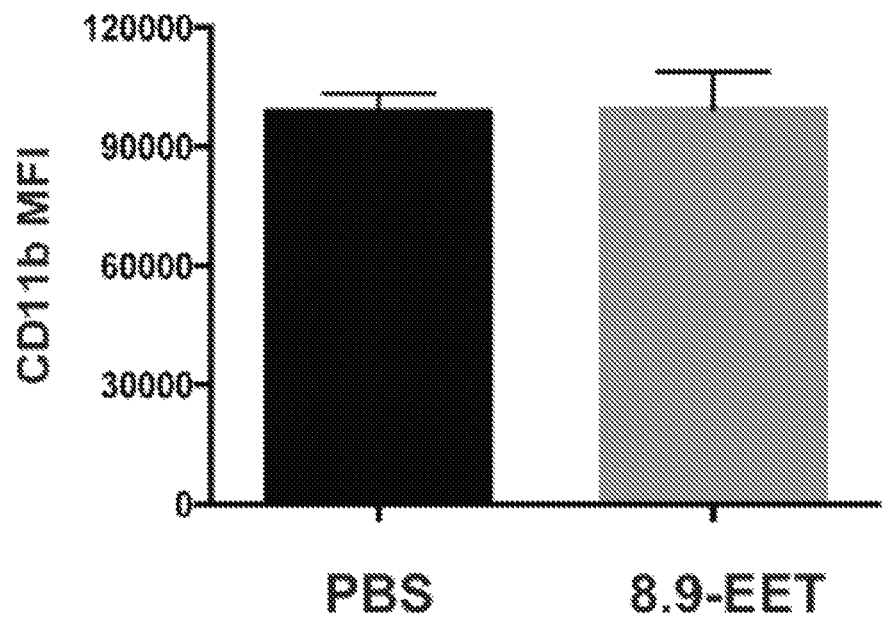
Figure 10F:
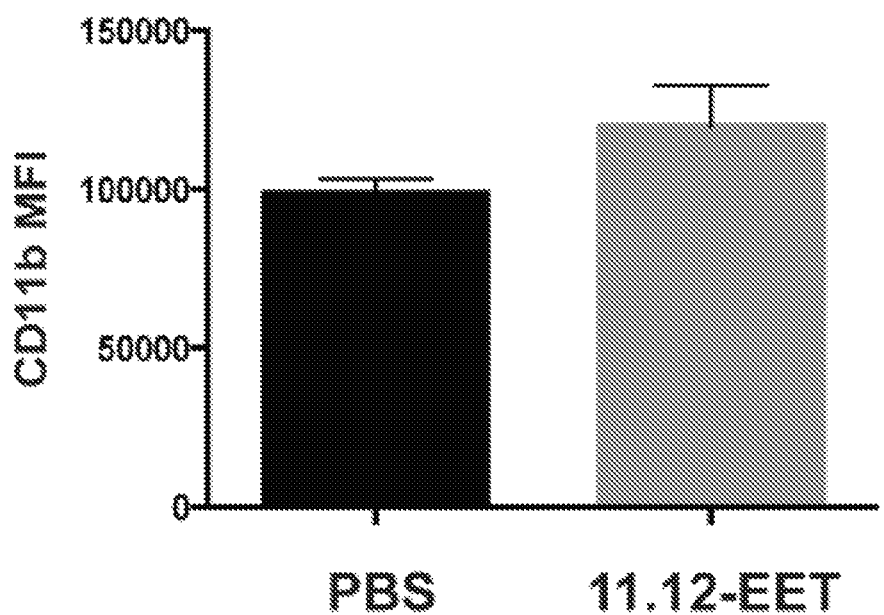
Figure 10G:
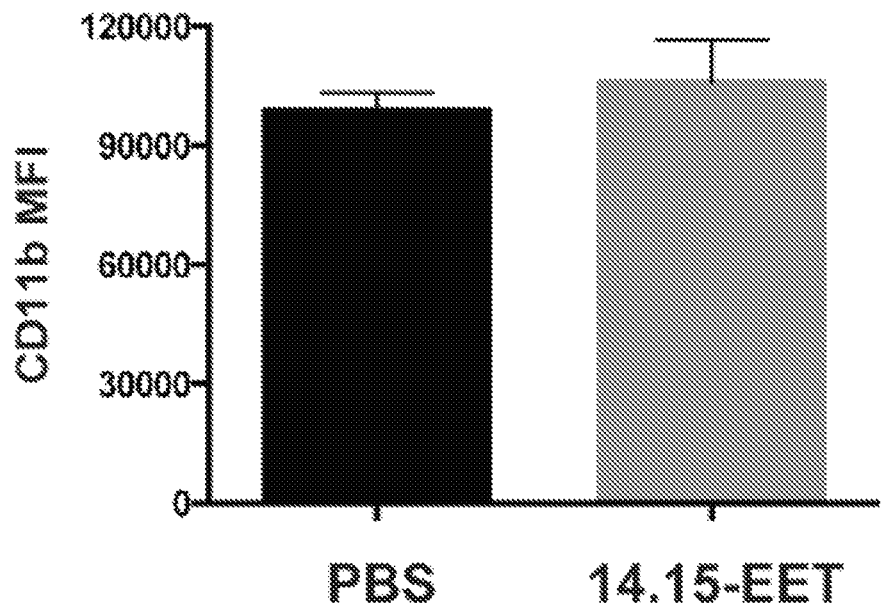
Figure 10H:
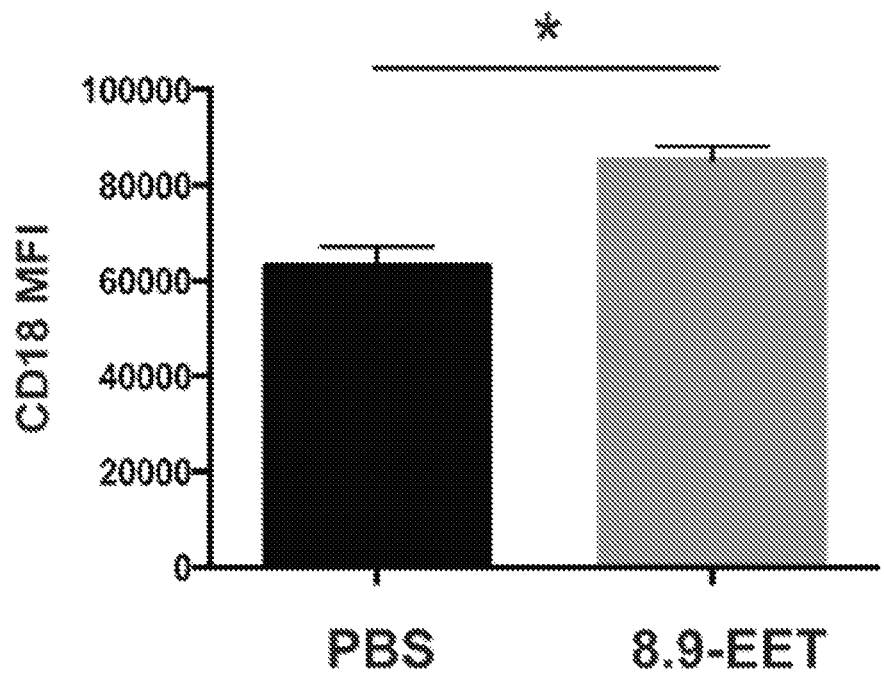
Figure 10I:
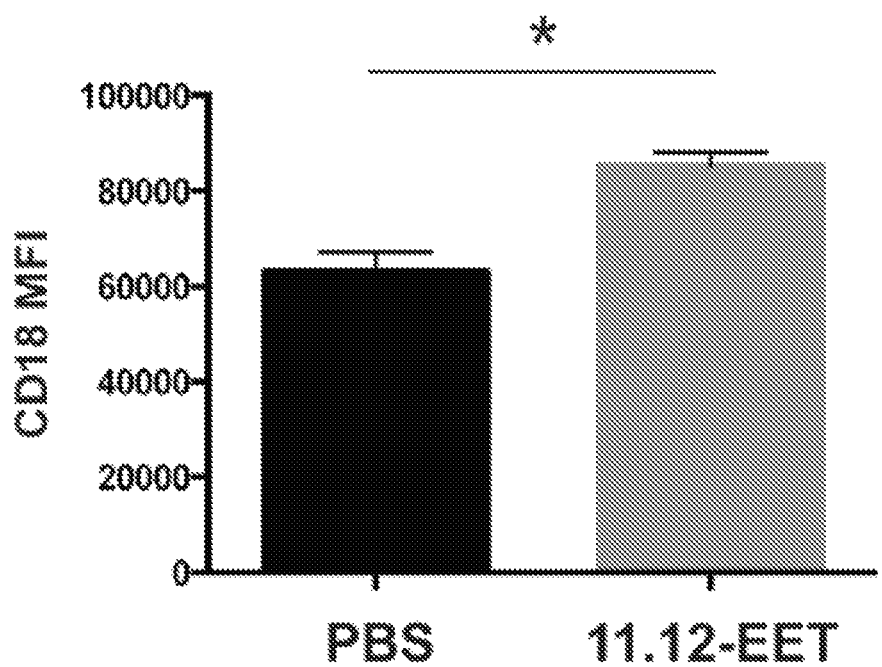
Figure 10J:
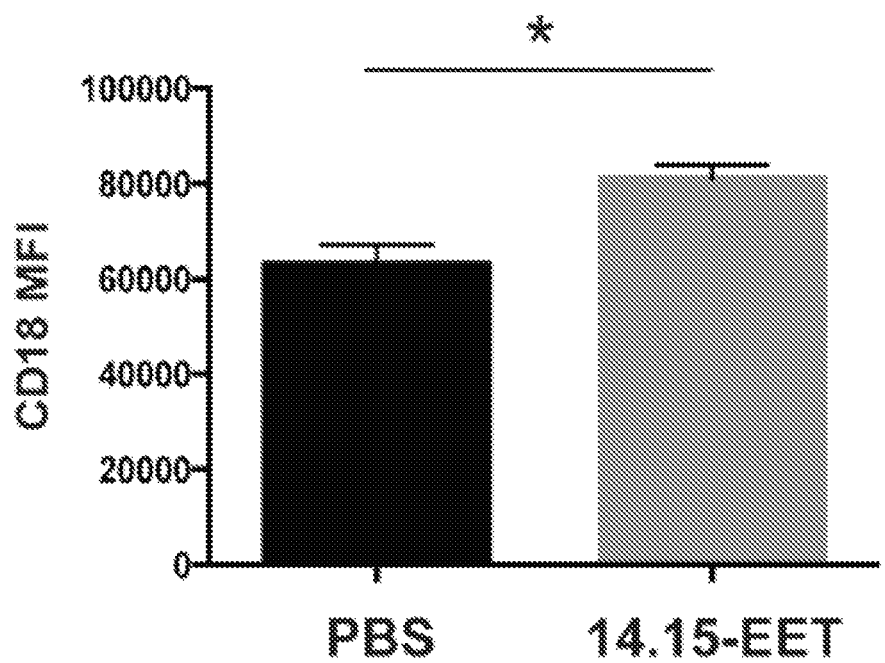
Figure 10K:
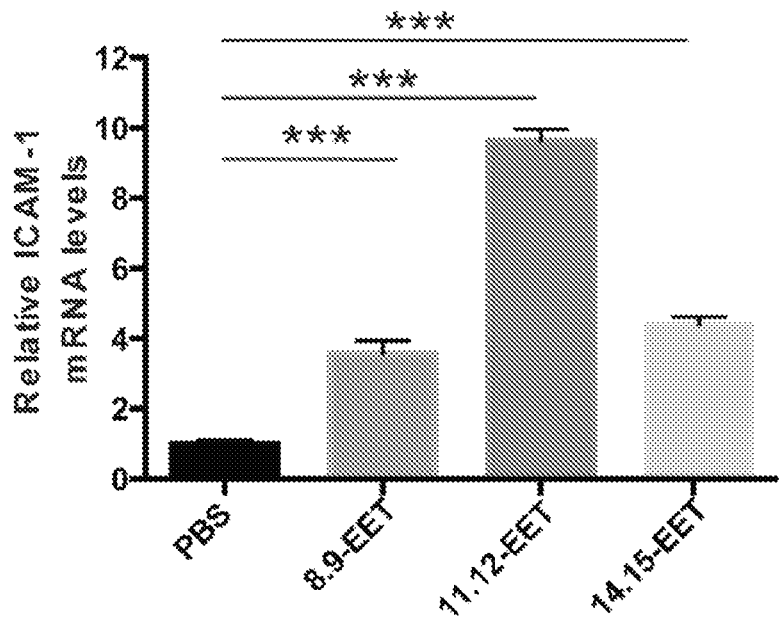
Figure 10L:
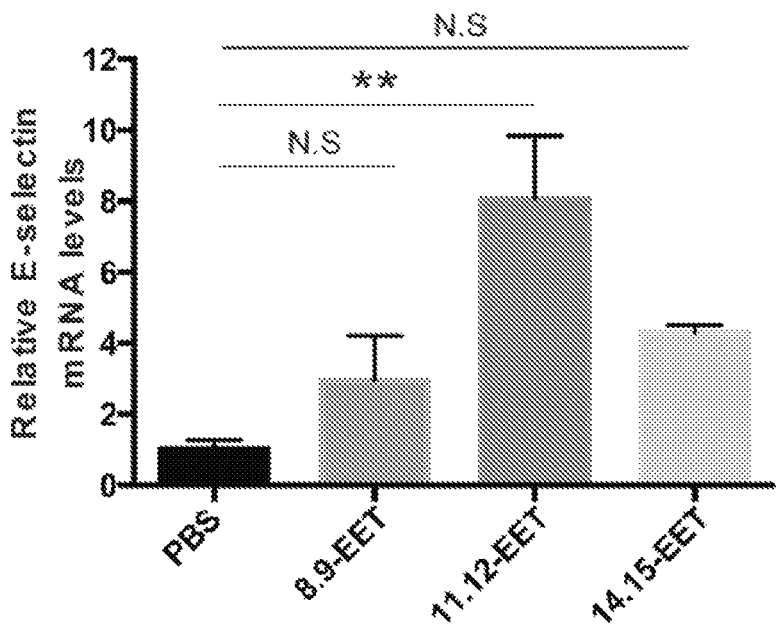

FIGS. 8A-8C show representative images of fundus, OCT, and FA images of CNV experiment using C21 in FIGS. 7A-7C: (A-C) CNV lesions at 7 d after laser photocoagulation were assessed by staining of choroidal flat-mount with fluorescent isolectin B4 (A), cross-sectional area of lesions quantified by SD-OCT (demarcated by circling) (B), and fluorescein angiography (C), for C57BL/6J mice administered control vehicle or C21 (50 µg/kg/day) once a day immediately after laser photocoagulation. Mice were fed a control diet over the course of the experiment. Scale bars: 100 µm.

Administration of C21 significantly reduced CNV size compared to administration of control vehicle as assessed in both choroidal flat mounts and SD-OCT. C21 significantly reduced the extent of vascular leakage observed in these lesions. Increasing resistance to degradation of ω-3 LCPUFA metabolites as well as increasing their corresponding bioavailability enhance protection against CNV.

Figure 20A:
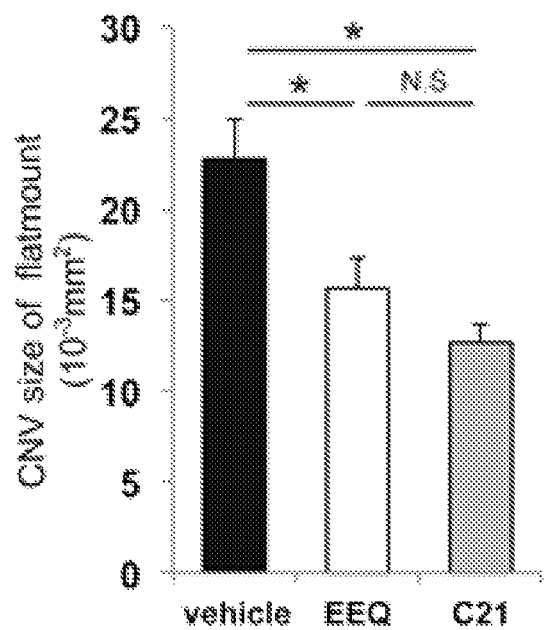
FIG. 20A is bar graph showing CNV lesion size quantified according to choroidal flat-mount size after administration of 17,18-EEQ, compound C21, and control vehicle.
Figure 20B:
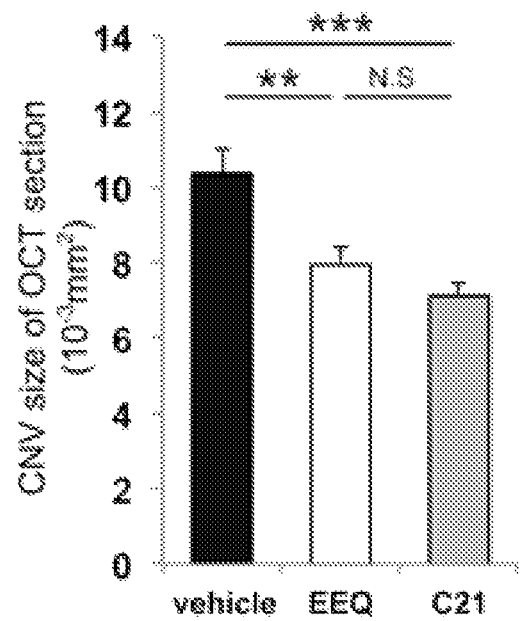
FIG. 20B is a bar graph showing cross-sectional area of lesions quantified by SD-OCT after administration of 17,18-EEQ, compound C21, and control vehicle.
Figure 20C:
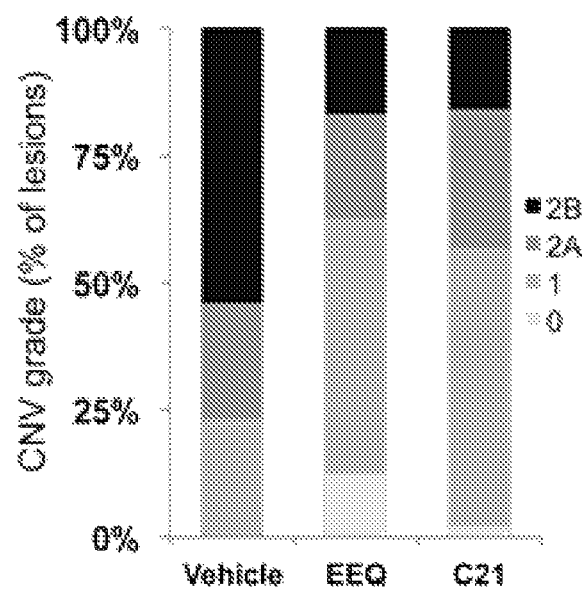
FIG. 20C is a bar graph showing grading of fluorescein leakage in CNV lesions post-CNV induction after administration of 17,18-EEQ, compound C21, and control vehicle.

FIGS. 20A-20C show that administration of C21 and EEQ attenuates CNV. C21 was administered intraperitoneally once a day for 7 days. *P<0.05; P<0.01; *P<0.001; n=37-48. As shown in FIGS. 20A-20C, administration of C21 significantly reduced CNV size compared to administration of control vehicle. C21 did not show a significant difference compared to EEQ administered alone.

Example 7—the Adhesion Ability of Leukocyte is Down-Regulated by Administration of CYP-Derived LCPUFA Eicosanoids Systemic leukocyte recruitment to extravascular areas plays crucial role in the inflammatory process and the pathophysiology of several diseases. Leukocytes in the blood stream attach and roll on the surface of endothelial cells via interactions between adherent molecules and their ligands, such as intercellular cell-adhesion molecules (ICAM) or selectins, leading to leukocyte crawling and transendothelial migration. Leukocyte recruitment to CNV lesions is a critical step in increasing the severity of exudative AMD. Consuming an EPA and DHA enriched diet down-regulates CNV by reducing leukocyte infiltration into the CNV lesions. (See Yanai R, et al. (2014) Cytochrome P450-generated metabolites derived from omega-3 fatty acids attenuate neovascularization. *Proc Natl Acad Sci USA* 111(26):9603-9608; Mitroulis I, et al. (2015) Leukocyte integrins: role in leukocyte recruitment and as therapeutic targets in inflammatory disease. *Pharmacol Ther* 147:123-135; Ambati J & Fowler B J (2012) Mechanisms of age-related macular degeneration. *Neuron* 75(1):26-39; Noda K, et al. (2008) Vascular adhesion protein-1 blockade suppresses choroidal neovascularization. *FASEB J* 22(8):2928-2935).

Autoperfused Microflow Chamber assay was used to assess the impact of 17,18-EEQ and 19,20-EDP on systemic leukocyte recruitment during CNV development. The rolling velocity of peripheral blood leukocytes (PBLs) in the circulating blood was measured 3 days post CNV induction, as this reflects the peak of immune cell infiltration in this model.

FIGS. 9A-9I show that administration of CYP-derived ω-3 LCPUFA metabolites modulates leukocyte rolling velocity and adhesion molecule expression: (A,B) Cumulative frequency of leukocyte rolling velocity in a chamber coated with both P-selectin and ICAM-1 was assessed at day 3 after CNV induction. Mice were injected i.p. with (A) 17,18-EEQ (50 μg/kg/day), (B) 19,20-EDP (50 μg/kg/day), or PBS daily beginning immediately after CNV induction. Administration of both EEQ and EDP increased leukocyte rolling velocity compared to PBS groups (n=3 mice per group). (C) Representative overlay images of individual leukocytes tracked over 10 s. (D-G) Flow cytometric analysis of (D, E) CD11b and (F, G) CD18 expression on peripheral blood leukocytes 3 days after CNV induction in C57BL/6 mice injected i.p. with (D, F) 17,18-EEQ (50 μg/kg/day) or (E, G) 19,20-EDP (50 μg/kg/day). Administration of EEQ decreased CD18 expression and EDP decreased CD11b expression on leukocytes compared to PBS injected groups. Data are presented as means±SEM. n=10 mice per group. MFI: mean fluorescence intensity values. *P<0.05. (H, I) Real-time PCR analysis of (H) ICAM-1 and (I) E-selectin mRNAs in laser-captured CNV lesions at 7 days after CNV induction in C57BL/6 mice injected i.p. with EEQ (50 μg/kg/day) and EDP (50 μg/kg/day). Administration of EEQ significantly decreased ICAM-1 and E-selectin expression compared to PBS injected groups. Data are presented as means±SEM. n=6 mice per group. *P<0.05.

The rolling velocity of PBLs on the chamber, which is coated with adherent molecules ICAM-1 and P-selectin, was significantly faster for mice administered 17,18-EEQ (1.48±0.16 μm/s) than for those administered PBS (0.94±0.06 μm/s). The rolling velocity of PBLs along the chamber was also significantly faster in mice administered 19,20-EDP (1.44±0.12 μm/s) than in mice administered PBS (0.94±0.06 μm/s). the functional down-regulation of ICAM-1 and P-selectin ligands on the surface of leukocytes in mice administered 17,18-EEQ and 19,20-EDP results in increased rolling velocity and decreased recruitment. To investigate the increase in ICAM-1-dependent rolling velocity of PBLs in mice administered 17,18-EEQ and 19,20-EDP, the expression of the ICAM-1 ligand, CD11b/CD18, on circulating leukocytes was measured. Flow cytometry analysis revealed that the surface expression level of CD11b on PBLs was significantly lower for mice administered 19,20-EDP, but not 17,18-EEQ, than for those administered PBS. On the contrary, the surface expression level of CD18 on PBLs was significantly lower for mice administered 17,18-EEQ, but not 19,20-EDP, than for those administered PBS. The effects of 17,18-EEQ and 19,20-EDP on the expression of adhesion molecules in CNV lesions were also examined. CNV lesions were collected using laser-capture microdissection. Mice administered 17,18-EEQ had significantly reduced mRNA levels of ICAM-1 and E-selectin in the CNV lesions 7 days post CNV induction compared to PBS injected controls. The increased rolling velocity of leukocytes from mice administered 17,18-EEQ and 19,20-EDP is attributable to the down-regulation of the expression of adhesion molecules (furthermore, each lipid metabolite has differential regulation on leukocytes or endothelial cells in CNV lesions).

Example 8—the Adhesion Ability of Leukocyte is Up-Regulated by Administration of CYP-Derived LCPUFAs Eicosanoids The effect of CYP-derived eicosanoids of AA, EETs, on leukocyte recruitment was also determined.

FIGS. 10A-10L show that administration of CYP-derived ω-6 LCPUFA metabolites modulates leukocyte rolling velocity and adhesion molecule expression: (A-C) Cumulative frequency of leukocyte rolling velocity in a chamber coated with both P-selectin and ICAM-1 were assessed at day 3 after CNV induction. Mice were injected i.p. with (A) 8.9-EET (50 μg/kg/day), (B) 11.12-EET (50 μg/kg/day), (C) 14.15-EET (50 μg/kg/day), or PBS daily beginning immediately after CNV induction. Administration of EETs decreased leukocyte rolling velocity compared to PBS groups (n=3 mice per group). (D) Representative overlay images of individual leukocytes tracked over 10 s. (E-J) Flow cytometric analysis of (E-G) CD11b and (H-J) CD18 expression on peripheral blood leukocytes 3 days after CNV induction in mice injected i.p. with (E, H) 8,9-EET (50 μg/kg/day), (F, I) 11,12-EET (50 μg/kg/day), or (G, J) 14,15-EET (50 μg/kg/day). Administration of EETs significantly increased CD18 expression on leukocytes compared to PBS injected groups. Data are presented as means±SEM. n=10 mice per experimental group. MFI: mean fluorescence intensity values. *P<0.05. (K, L) Real-time PCR analysis of (K) ICAM-1 and (L) E-selectin mRNAs in laser-captured CNV lesions at 7 days after CNV induction in injected i.p. with EETs (50 μg/kg/day for each group). Administration of EETs significantly increased ICAM-1 expressions and administration of 11,12-EET increased E-selectin expressions compared to PBS injected group. Data are presented as means±SEM. n=6 mice per experimental group. P<0.01 *P<0.001. N.S: not significant.

The rolling velocity of PBLs along the chamber was significantly decreased for mice administered 8,9-EET (1.14±0.15 μm/s) than those administered PBS (2.30±0.13 μm/s). The rolling velocity of PBLs on the chamber was also significantly decreased in mice administered other regioisomeric EETs, 11,12-EET (1.41±0.45 μm/s) and 14,15-EET (1.41±0.11 μm/s), than in mice administered PBS (2.30±0.13 μm/s). The surface expression levels of CD11b on PBLs were unchanged for mice administered each EET compared to those administered PBS. Conversely, the surface expression levels of CD18 on PBLs were significantly higher for mice administered EETs compared to those administered PBS. Mice administered EETs had significantly increased levels of ICAM-1 mRNAs in the CNV lesions 7 days post CNV induction compared to PBS injected controls. In contrast, only 11,12-EET showed significant increase in the mRNA level of E-selectin compared to mice administered PBS. the decreased rolling velocity and increased recruitment of leukocytes from mice administered EETs are attributable to the up-regulation of the expression of adhesion molecules both on the surface of leukocytes and on endothelial cells in CNV lesions.

Example 9—Blockade of the Metabolic Degradation of CYP-Derived Fatty Acids of EPA and DHA Enhances the Protective Effect Against CNV To elucidate the effect of CYP-derived fatty acids of EPA and DHA on CNV, the sEH inhibitor was utilized (1-trifluoromethoxyphenyl-3-(1-propionylpiperidin-4-yl) urea), which can block the degradation of 17,18-EEQ and 19,20-EDP by sEH (See Rose T E, et al. (2010) 1-Aryl-3-(1-acylpiperidin-4-yl)urea inhibitors of human and murine soluble epoxide hydrolase: structure-activity relationships, pharmacokinetics, and reduction of inflammatory pain. J Med Chem 53(19):7067-7075). Daily intraperitoneal injections of 17,18-EEQ and 19,20-EDP were administered to mice on a control diet with or without sEH inhibitor administered orally in the drinking water.

Figure 11A:
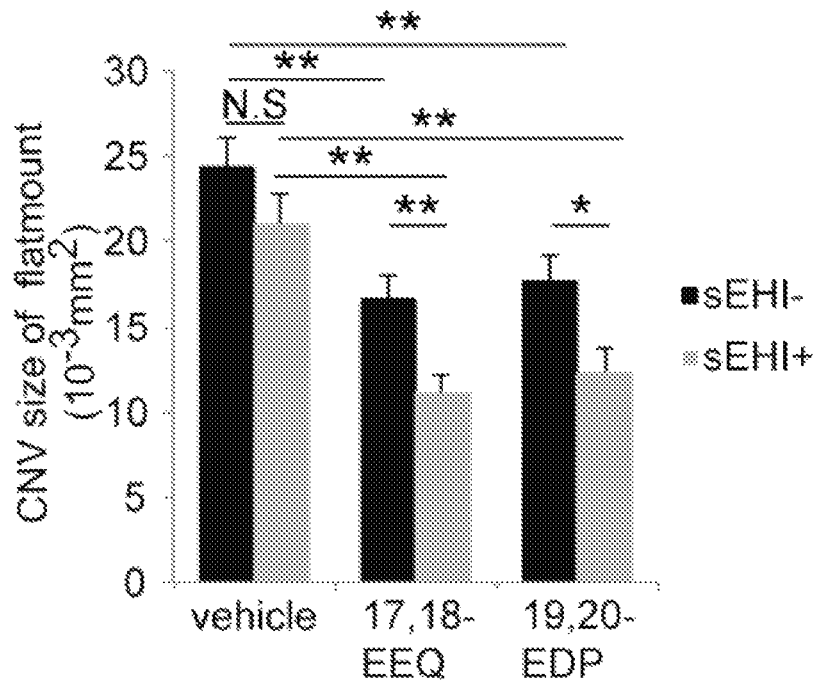
FIGS. 11A-11D. Lesion size at 7 d after CNV induction was assessed by staining of choroidal flat-mount preparations with fluorescent isolectin B4 (FIG. 11A), and cross-sectional area of lesions was quantified by SD-OCT (FIG. 11B), for C57BL/6 mice administered control vehicle, 17,18-EEQ (50 µg/kg/day), or 19,20-EDP (50 µg/kg/day) once a day without sEH Inhibitor (Black bars) or with sEH Inhibitor (1 mg/kg/day, Gray bars).
Figure 11B:
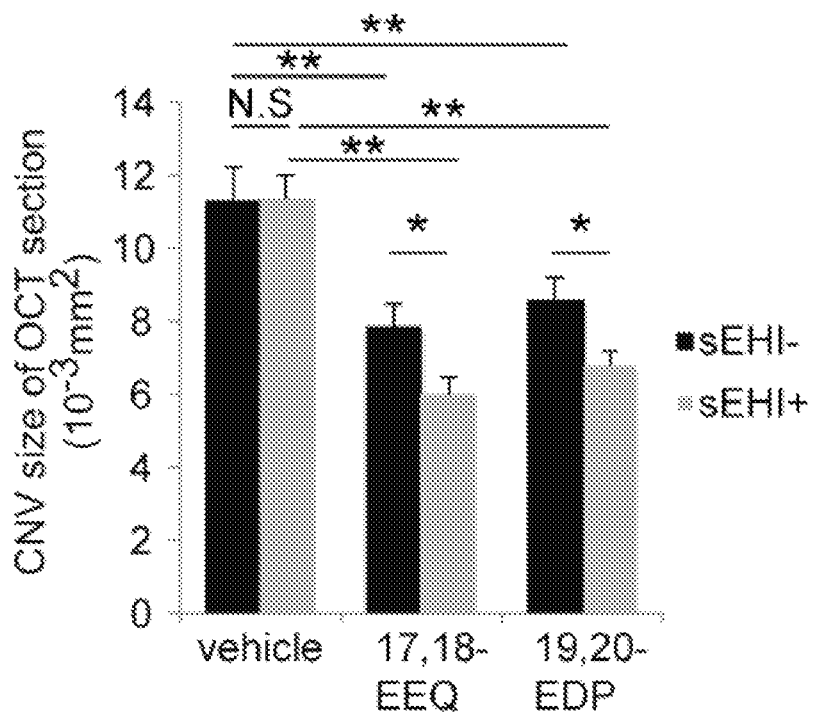
Figure 11C:
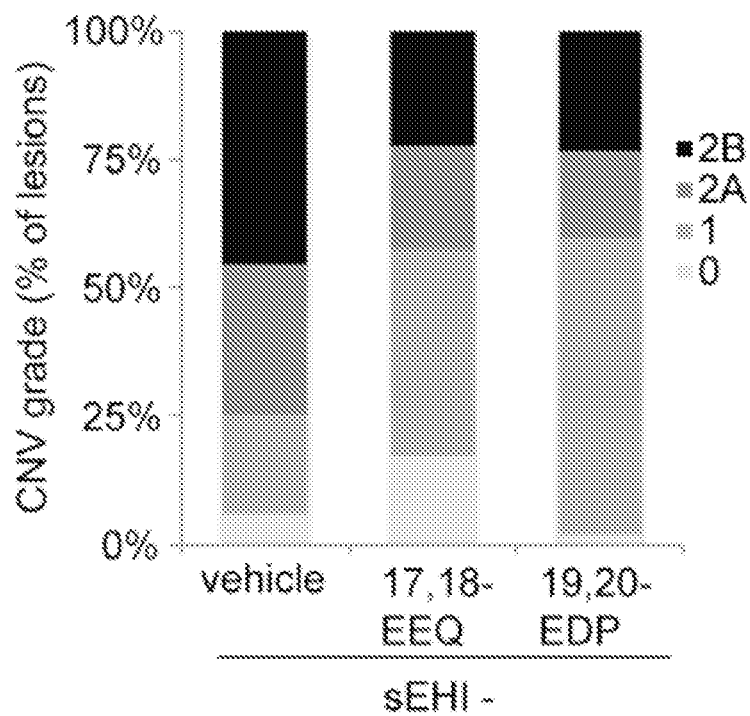
Figure 11D:
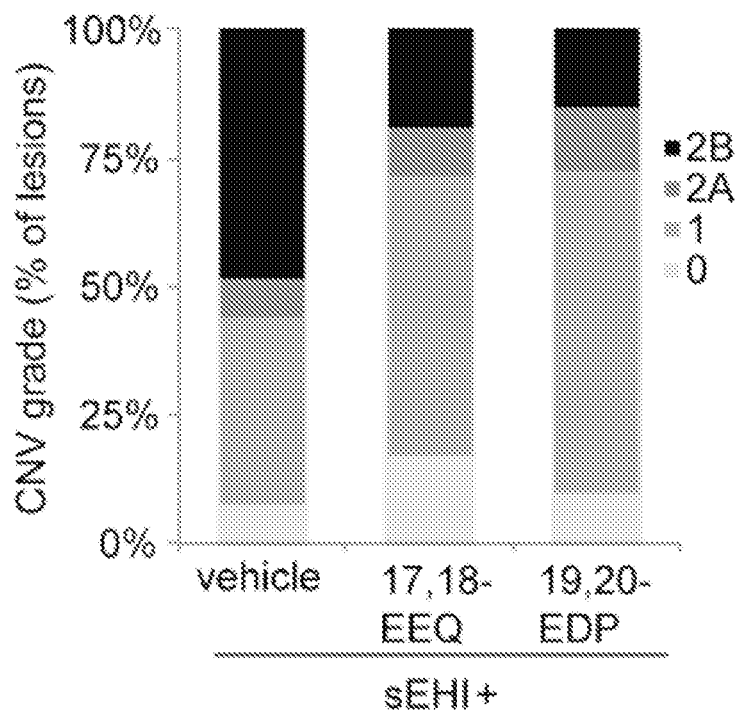

FIGS. 11A-11C shows that sEH inhibitor (1-trifluoromethoxyphenyl-3-(1-propionylpiperidin-4-yl) urea) enhances the inhibitory effect of CYP-derived ω-3 fatty acids on CNV: (A, B) Lesion size at 7 d after CNV induction was assessed by staining of choroidal flat-mount preparations with fluorescent isolectin B4 (A), and cross-sectional area of lesions was quantified by SD-OCT (B), for C57BL/6 mice administered control vehicle, 17,18-EEQ (50 μg/kg/day), or 19,20-EDP (50 μg/kg/day) once a day without sEH Inhibitor (Black bars) or with sEH Inhibitor (1 mg/kg/day, Gray bars). Mice were fed a control diet over the course of the experiment. Data are presented as means±SEM. *P<0.05. **P<0.01. n=35-43 lesions per experimental group. (C, D) Fluorescein leakage in CNV lesions was graded at 7 d after CNV induction in C57BL/6 mice administered control vehicle, 17,18-EEQ (50 μg/kg/day), or 19,20-EDP (50 μg/kg/day) once a day without sEH inhibitor (C) or with sEH inhibitor (1 mg/kg/day)(D). Mice were fed a control diet over the course of the experiment. n=35-43 lesions per experimental group.

Figure 12A:
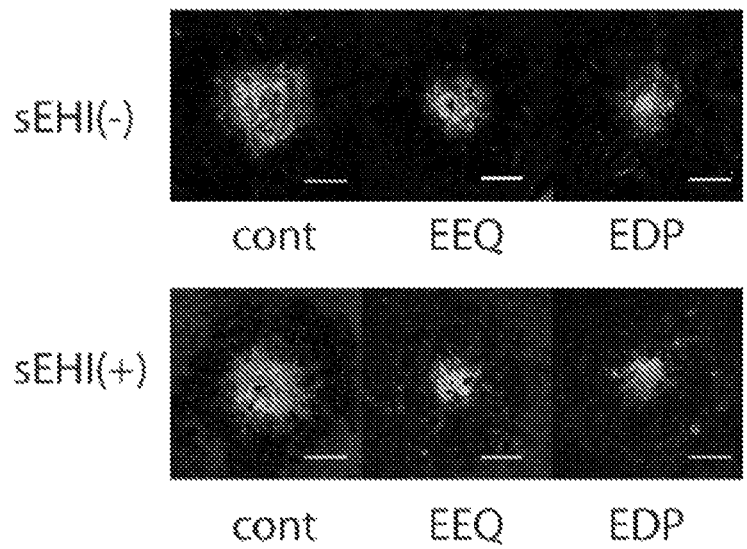
FIGS. 12A-12C. CNV lesions at 7 d after laser photocoagulation were assessed by staining of choroidal flat-mounts with fluorescent isolectin B4 (FIG. 12A), cross-sectional area of lesions quantified by SD-OCT (demarcated by red lines) (FIG. 12B), and fluorescein angiography (FIG. 12C), for C57BL/6J mice administered control vehicle, 17,18-EEQ (50 µg/kg/day), or 19,20-EDP (50 µg/kg/day) once a day with or without sEH Inhibitor (1 mg/kg/day).
Figure 12B:
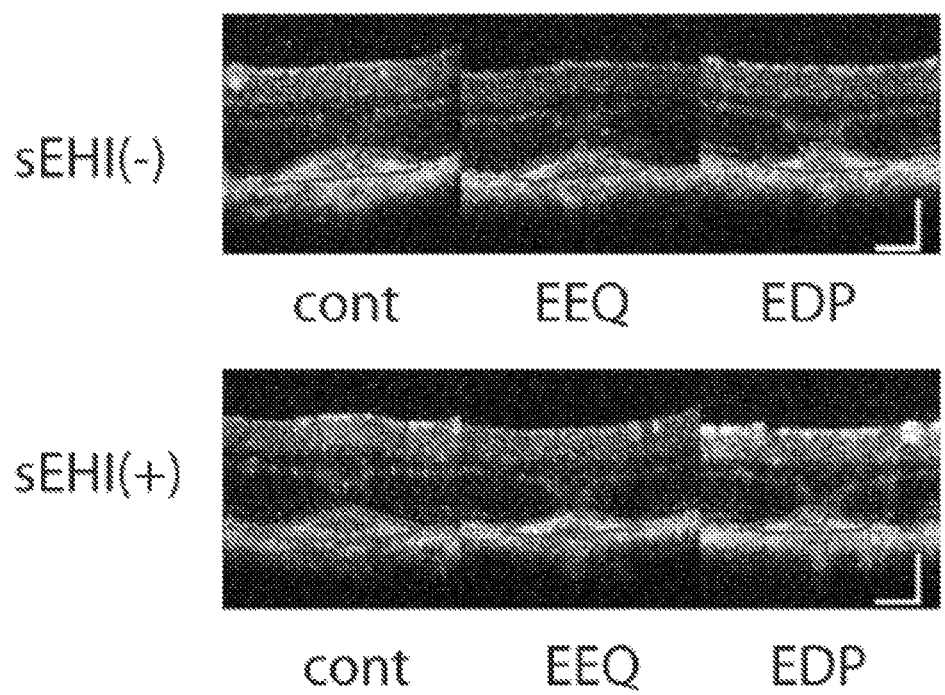
Figure 12C:
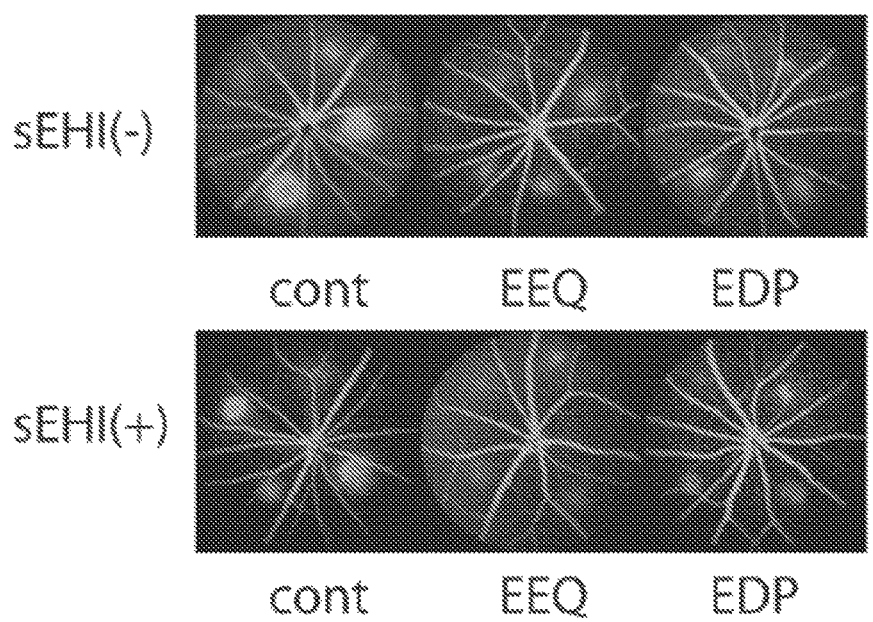

FIGS. 12A-12C show representative images of fundus, OCT, and FA images of CNV experiment using sEH inhibitor in FIGS. 11A-11D. (A-C) CNV lesions at 7 d after laser photocoagulation were assessed by staining of choroidal flat-mounts with fluorescent isolectin B4 (A), cross-sectional area of lesions quantified by SD-OCT (demarcated by red lines)(B), and fluorescein angiography (C), for C57BL/6J mice administered control vehicle, 17,18-EEQ (50 μg/kg/day), or 19,20-EDP (50 μg/kg/day) once a day with or without sEH Inhibitor (1 mg/kg/day). Mice were fed a control diet over the course of the experiment. Scale bars: 100 μm.

The administration of both 17,18-EEQ and 19,20-EDP alone significantly attenuated CNV size in choroidal flat mounts (FIG. 11A, black bars) and in cross-sectional OCT images compared to the administration of vehicle control (FIG. 11B, black bars). The administration of both 17,18-EEQ and 19,20-EDP alone also significantly reduced the severity of vascular leakage in CNV lesions (FIG. 11C). However, co-administration of the sEH inhibitor with either 17,18-EEQ or 19,20-EDP further attenuated CNV size (FIGS. 11A and 11B, gray bars, 12A, 12B) and also decreased the severity of vascular leakage in CNV lesions (FIG. 11D, 12C) compared with 17,18-EEQ or 19,20-EDP administration alone.

Example 10—sEH Inhibitor 1-adamantanyl-3-{5-[2-(2-ethoxyethoxy)ethoxy]pentyl]}urea (AEPU)

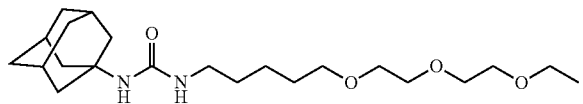 [SMILES: CCOCCOCCOCCCCCNC(=O)NC12CC3CC(CC(C3)C1)C2]

Synthesis and General Information

See, e.g.: Kim I H, Tsai H J, Nishi K, Kasagami T, Morisseau C, Hammock B D. 1,3-Disubstituted Ureas Functionalized with Ether Groups are Potent Inhibitors of the Soluble. Epoxide Hydrolase with Improved Pharmacokinetic Properties. J. Med. Chem. 2007; 50: 5217-5226; Chiamvimonvat N, Ho C M, Tsai H J and Hammock B D. The soluble epoxide hydrolase as a pharmaceutical target for hypertension. J Cardiovasc Pharmacol 2007; 50:225-237; Hwang S H, Tsai H J, Liu J Y, Morisseau C, Hammock B D. Orally bioavailable potent soluble epoxide hydrolase inhibitors. J Med Chem. 2007; 50(16):3825-40; Inceoglu B, Jinks S L, Schmelzer K R, Waite T, Kim I H, Hammock B D. Inhibition of soluble epoxide hydrolase reduces LPS-induced thermal hyperalgesia and mechanical allodynia in a rat model of inflammatory pain. Life Sci. 2006; 79(24):2311-9; Ulu A, Davis B B, Tsai H J, Kim I H, Morisseau C, Inceoglu B, Fiehn O, Hammock B D, Weiss R H. Soluble epoxide hydrolase inhibitors reduce the development of atherosclerosis in apolipoprotein e-knockout mouse model. J Cardiovasc Pharmacol. 2008; 52(4):314-23.

Chemical Information

Melting Point: 78.5-79° C.

Physical state: White powder

Solubility

Water solubility: 121.3±13.4 μg/mL, 250<x<500 μM

Solubility in DMSO: Soluble, >10 mM

Solubility in PEG400: Soluble

Solubility in other solvents: Triglyceride solubility 2 mg/mL

Experimental log P: 2.6

Calculated log P: 5.8 sEH Inhibition Data ($IC_{50}$)

|  | Mouse | Rat | Cat | Dog | Hamster | Human |
| --- | --- | --- | --- | --- | --- | --- |
| $IC_{50}$ (nM) | 3 | 5 | 27 | 86 | 2 | 14 |
| Relative Potency* | 3.3 | 2.2 | 0.1 | 0.03 | 2.5 | 0.2 |

*AUDA used as a reference
Relative potency: AUDA $IC_{50}$/Compound $IC_{50}$
$IC_{50}$ data are obtained from fluorescent substrate, CMNPC, α-cyanocarbonate.

Pharmacokinetics

Figure 13:
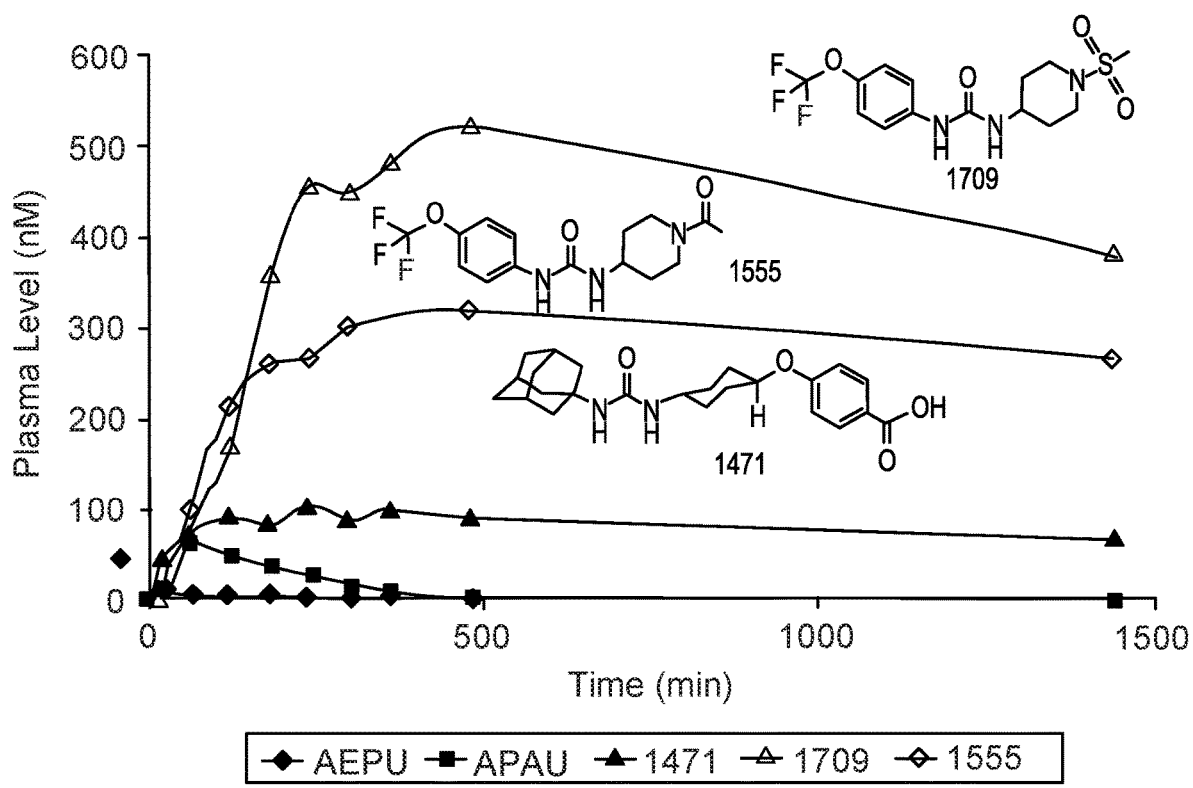
FIG. 13 is a line graph showing pharmacokinetic profile of sEH inhibitors 1709, 1555, 1471, AEPU and APAU in dogs, oral gavage.

FIG. 13 shows pharmacokinetic profile in dogs, oral gavage. Canine model, oral administration, dose 0.3 mg/kg body weight (Data from Chiamvimonvat N et al., J Cardiovasc Pharmacol 2007; 50:225-237.)

Figure 14:
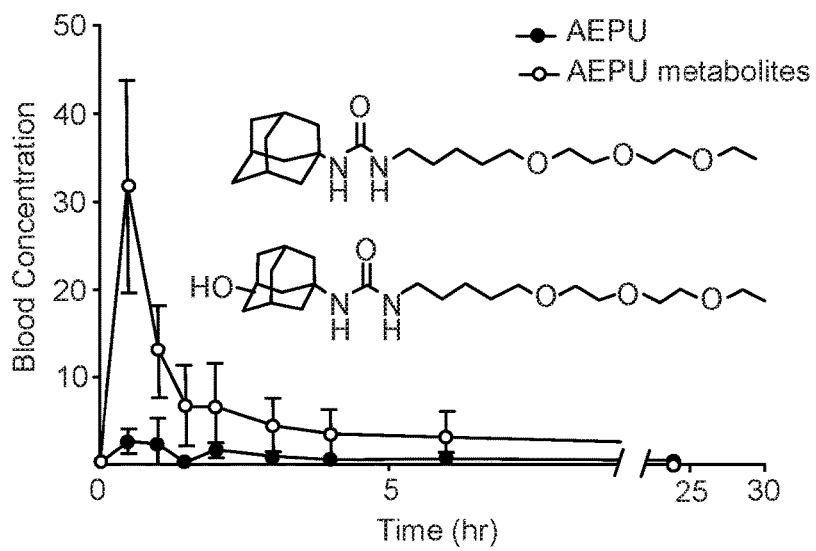
FIG. 14 is a line graph showing pharmacokinetic profile of sEH inhibitor AEPU and its metabolite in mice, oral gavage.

FIG. 14 shows pharmacokinetic profile in mice, oral gavage. Male CFW mice were treated with 10 mg/kg of AEPU in 100 μl of oleate rich triglyceride by oral gavage. Ten μl of blood was collected from tail vein at 0, 0.5, 1, 2, 3, 4, 6, and 24 h after the AEPU administration. Data from Ulu A, Davis B B, Tsai H J, Kim I H, Morisseau C, Inceoglu B, Fiehn O, Hammock B D, Weiss R H. Soluble epoxide hydrolase inhibitors reduce the development of atherosclerosis in apolipoprotein e-knockout mouse model. J Cardiovasc Pharmacol 2008; 52(4), 314-23.

Formulation in Triglyceride

Dissolve 4.5 mg of AEPU in 3 ml of oleic ester rich triglyceride to a final concentration of 1.5 mg/ml.

Formulation in Drinking Water

Unlike AUDA, AEPU dissolve in water without a cosolvent. Dissolve AEPU in ethanol to a final concentration of 0.1% v/v ethanol and 90 µg/ml in drinking water.

Example 11—sEH Inhibitor 1-trifluoromethoxyphenyl-3-(1-propionylpiperidin-4-yl) urea (TPPU)

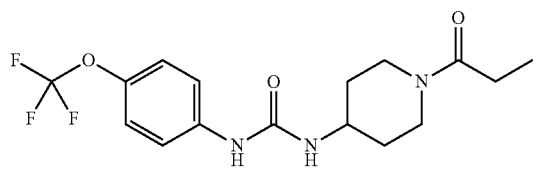 [SMILES: CCC(=O)N1CCC(NC(=O)Nc2ccc(OC(F)(F)F)cc2)CC1]

Synthesis and Pharmacokinetics:

See, e.g.: Rose, T. E., C. Morisseau, J-Y. Liu, B. Inceoglu, P. D. Jones, J. R. Sanborn and B. D. Hammock. 2010. 1-Aryl-3-(1-acylpiperidin-4-yl)urea inhibitors of human and murine soluble epoxide hydrolase: structure—activity relationships, pharmacokinetics, and reduction of inflammatory pain. J. Med. Chem. 53(19):7067-7075; Tsai, H-J., S. H. Hwang, C. Morisseau, J. Yang, P. D. Jones, T. Kasagami, I-H. Kim and B. D. Hammock. 2010. Pharmacokinetic screening of soluble epoxide hydrolase inhibitors in dogs. Eur. J. Pharm. Sci. 40(3):222-238; Ulu A, Appt S, Morisseau C, Hwang Sh, Jones P, Rose T, Dong H, Lango J, Yang J, Tsai H, Miyabe C, Fortenbach C, Adams M, Hammock B. 2012. Pharmacokinetics and in vivo potency of soluble epoxide hydrolase inhibitors in cynomolgus monkeys. Br J Pharmacol. 165(5):1401-12.

Chemical Information:

Melting Point: 198.2-200.8° C.

Physical state: White powder

Solubility:

Water solubility: 60 µg/ml

Solubility in DMSO: >10 mM

Solubility in PEG400: 90 mg/ml

Solubility in other solvents: Methanol

Experimental log P: 2.5±0.5

Calculated log P: 1.5

Plasma protein binding: 77% sEH Inhibition Data ($IC_{50}$, nM):

|  | Human | Mouse |
| --- | --- | --- |
| IC50 (nM) | 2.1 | 1.1 |
| Relative Potency* | 1.42 | 9.09 |

*AUDA used as a reference
Relative potency: AUDA $IC_{50}$/Compound $IC_{50}$
$IC_{50}$ data are obtained from fluorescent substrate, CMNPC, a-cyanocarbonate.

Formulation

TPPU may be dissolved in pure PEG (may require overnight warming at 50° C.). TPPU may be formulated in 20% PEG in oleic acid rich oil for oral administration.

Example 12—Pharmacokinetic Data of sEH Inhibitors (TPPU (1770), 1709, 1153, 1471, 1555) in Mice Male Swiss Webster mice (8 week old, 24-30 g) were used for PK studies. Inhibitors for oral administration were dissolved in oleic acid-rich triglyceride containing 20% PEG400 (v/v) to give a clear solution. Blood (10 µL) was collected from the tail vein using a pipette tip rinsed with 7.5% EDTA(K3) at 0, 0.5, 1, 1.5, 2, 4, 6, 8, 24 h after administration of the inhibitor. In addition to the above-mentioned time points, blood was collected at additional 15 minutes after administration for i.v. injection of sEHI. Each blood sample was immediately transferred to a tube containing 50 µL of water containing 0.1% EDTA. After mixing strongly on a Vortex for 1 min, all samples were stored at −80° C. until analysis.

Figure 15:
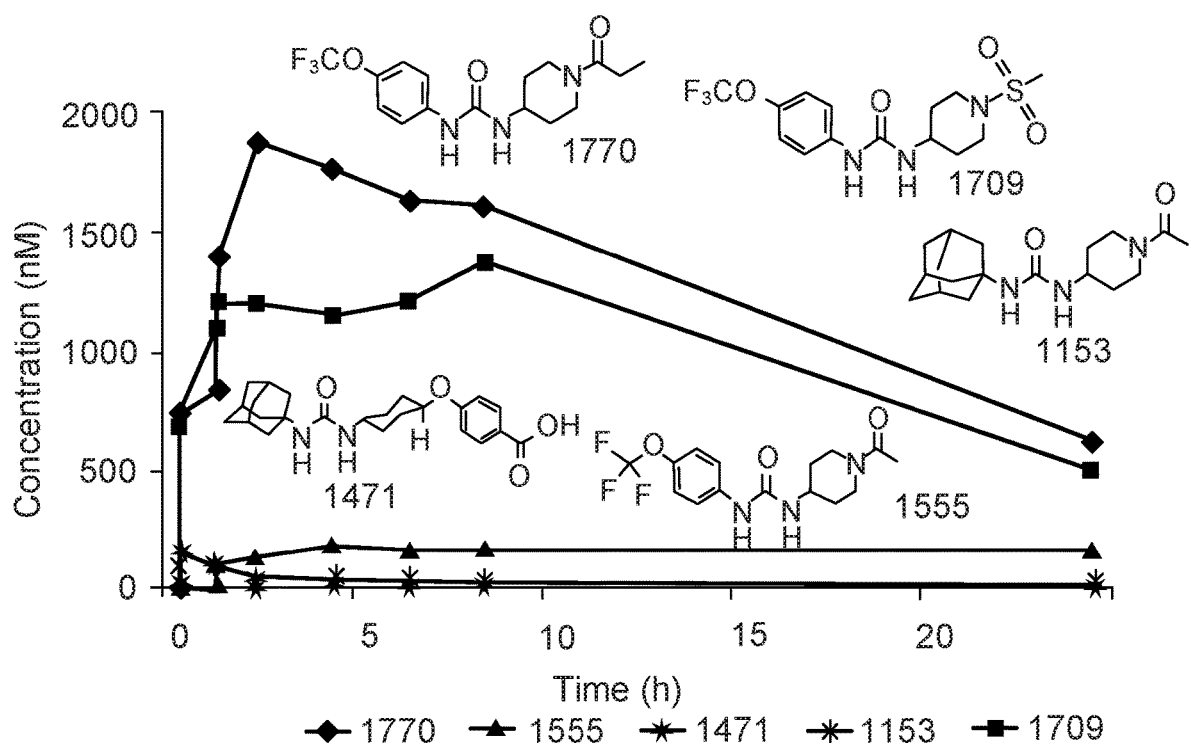
FIG. 15 is a line graph showing pharmacokinetic profile of sEH inhibitors TPPU (1770), 1555, 1471, 1153 and 1709 with oral dosing at 1 mg/kg.
Figure 16:
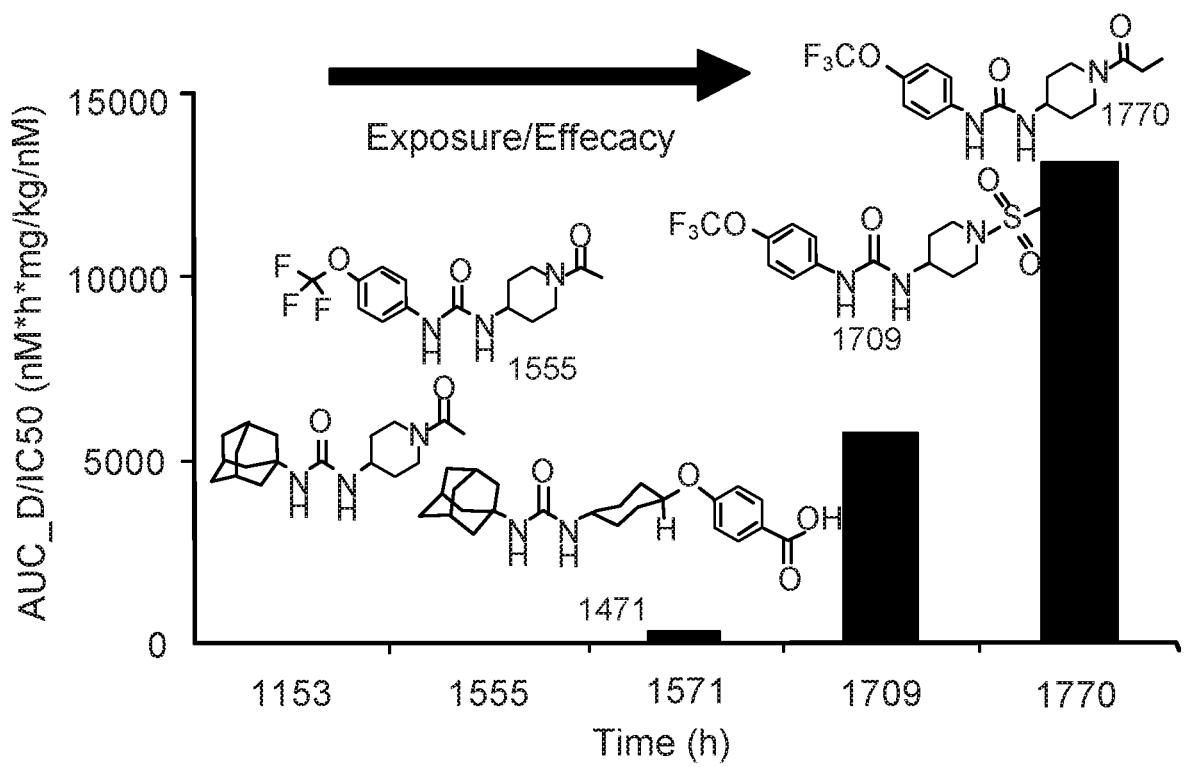
FIG. 16 is a bar graph showing exposure of mice to sEH inhibitors 1770, 1153, 1471, 1555, 1709 at 1 mg/kg and in vitro efficacy ($IC_{50}$ of hSEH).

See FIG. 15 (Pharmacokinetic profile of compounds with oral dosing at 1 mg/kg). See FIG. 16 (sEH inhibitor exposure of mice at 1 mg/kg/in vitro efficacy, $IC_{50}$ of hSEH).

Example 13—Pharmacokinetic Data of TPPU in Primates

Figure 17:
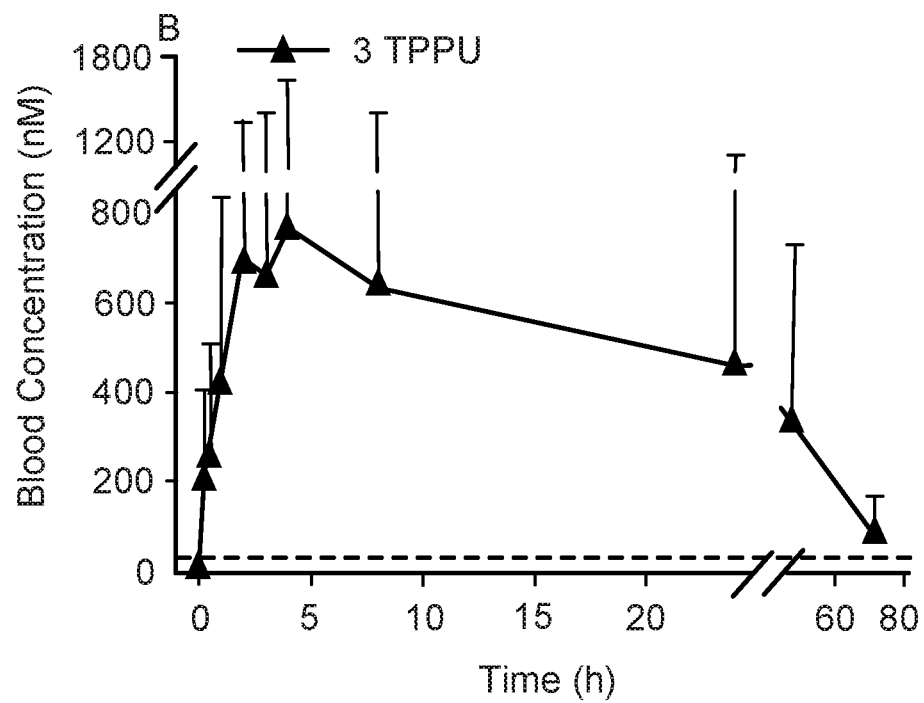
FIG. 17 is a line graph showing blood concentration of TPPU (1770) over time in primates.

Four female cynomolgus monkeys (*Macaca fascicularis*, long-tailed or crab-eating macaque), ranging in age between 16-18 years (based on their dental examination) and weighing between ~2.5-4 kg, were used for the dosing of the sEHIs. The animals were fasted during the experiments and were sedated with ketamine (15 mg/kg I.M.) to administer the sEHIs by gastric intubation. TPPU was given at 0.3 mg/kg dose via cassette dosing. Blood was collected from tail vein of the four cynomolgus monkeys at time points 0, 0.25, 0.5, 1, 2, 3, 4, 8, 24, 48 and 72 h upon oral cassette dosing at 0.3 mg/kg. Each time point represents mean±sem on the graph. The dotted line represents the $IC_{50}$ of the inhibitor in hepatic cytosol of cynomolgus monkeys. See FIG. 17 (blood concentration of TPPU over time)

Figure 18:
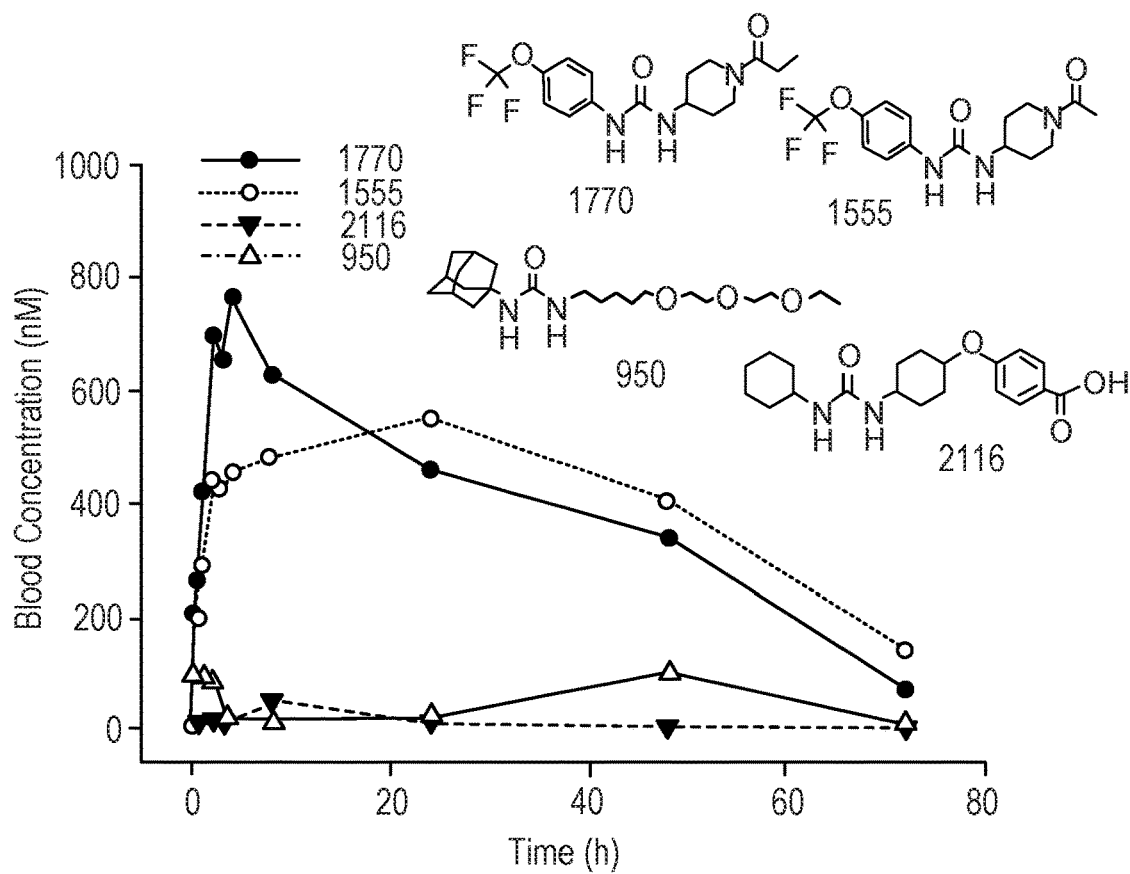
FIG. 18 is a line graph showing pharmacokinetics of sEH inhibitors TPPU (1770), 1555, 2116 and 950 in primates, oral dosing at 0.3 mg/kg. Line plot showing blood concentration (nM) over time.

Example 14—Pharmacokinetic Data of sEH Inhibitors (TPPU (1770), 950, 1555, 2116) in Primates See FIG. 18 (Pharmacokinetics of she inhibitors TPPU (1770), 1555, 2116 and 950 in primates, oral dosing at 0.3 mg/kg). Line plot showing blood concentration (nM) over time.

Figure 19:
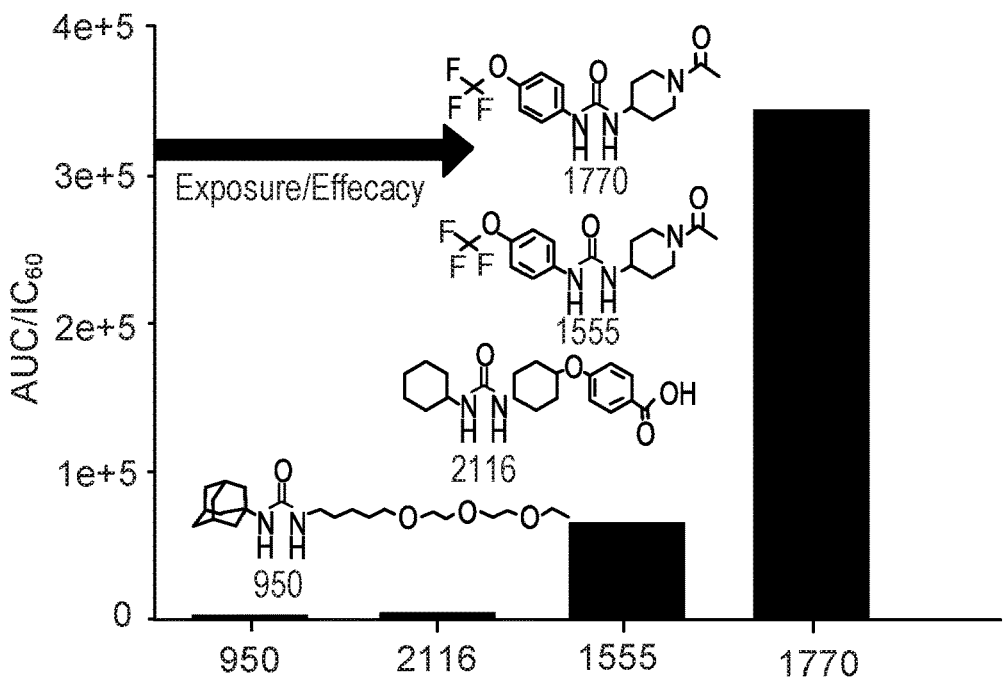
FIG. 19 is a bar graph showing exposure of primates to sEH inhibitors 950, 2116, 1555 and 1770 (AUC) and potency of hsEH ($IC_{50}$).

See FIG. 19 (sEH inhibitor exposure (AUC)/potency of hSEH ($IC_{50}$)). Referring to FIG. 19, the bars indicate exposure expressed as AUC for plasma levels in rhesus following oral administration at 0.1 mg·kg as a function of $IC_{50}$ of the human enzyme. A high bar indicates both potency and exposure. Four rhesus monkeys (4 to 7 years old) were used for each study. The arrow indicates the potency level reached by APAU.

Example 15—Formulations of Selected Inhibitors of sEH

| Inhibitor | Formulation (mg/mL) | | |
|---|---|---|---|
| | EtOH | PEG400 | Trioleate |
| 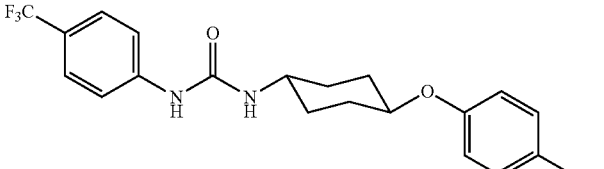 | 20 | 20 | 0.625 |
| 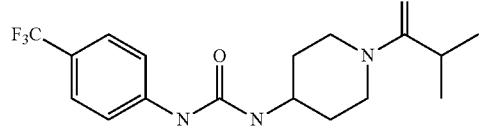 | 20 | 20 | 0.625 |
| 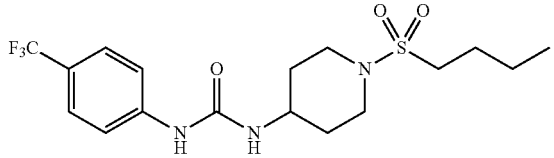 [SMILES: CCCCS(=O)(=O)N1CCC(NC(=O)Nc2ccc(C(F)(F)F)cc2)CC1] | 13 | 13 | 1.25 |

Example 16—sEH Inhibitory Potency and Physical Properties of Ureas Found in Brassicales

| | $R_1$ | $R_1'$ | $R_2$ | $R_2'$ | Human sEH $IC_{50}$ (nM)[a] | Rat sEH $IC_{50}$ (nM)[a] | Solubility[b] (μM) | Melting point (° C.) |
|---|---|---|---|---|---|---|---|---|
| 1 | H | H | H | H | 1900[c] | 385 | 43 ± 5 | 168-170 |
| BMU | OCH₃ | H | H | H | 400[c] | 182 | 9 ± 4 | 139.6-140.2[c] |
| 2 | H | OCH₃ | H | H | 534 | 308 | 77 ± 9 | 108.3-109.1 |
| MMU | OCH₃ | H | OCH₃ | H | 92[c] | 218 | 11 ± 2[c] | 177.7-178.4[c] |
| 3 | H | OCH₃ | H | OCH₃ | 222 | 155 | 101 ± 37 | 112.6-113.8 |

[a]Measured using CMNPC as a substrate. The fluorescent-based assay as performed here has a standard error between 10% and 20%, suggesting that differences of two-fold or greater are significant.
[b]Solubility in sodium phosphate buffer (pH7.4). Mean ± SD (n = 3) are shown.
[c]Data from Kitamura et al., (2015).

The results presented herein show that CYP-derived ω-3 metabolites modulate CNV disease progression and severity (e.g., using transgenic mice that either overexpress or lack CYP-specific enzymes, see, e.g., Examples 1-3). Overexpression of the monooxygenase CYP2C8 (see, e.g., Example 1) or genetic ablation or inhibition of the soluble epoxide hydrolase (sEH) enzyme (see, e.g., Example 2) leads to increased levels of EDP and EEQ with attenuated CNV development. In contrast, degradation of these CYP-derived metabolites was promoted by transgenic overexpression of she (see, e.g., Example 3), the protective effect against CNV was lost. As shown herein, endothelium-specific overexpression of human CYP2C8, coupled with a EPA and DHA enriched diet, markedly attenuated CNV development with a corresponding increase in the plasma levels of 17,18-EEQ and 19,20-EDP (See, e.g., Example 5). Pharmacological inhibition of sEH (see, e.g., Example 9) and chemical stabilization of 17,18-EEQ (see, e.g., Example 6) were shown to be effective in attenuating CNV development.

Without being bound by any particular theory, it is believed that the present application provides results showing contribution of the CYP monooxygenases and their metabolites on CNV, and the effect of CYP-dependent fatty acids on leukocyte recruitment during CNV formation. The results show that CYP-dependent fatty acids regulate the leukocyte rolling velocity by modulating the expression of adhesion molecules both on the surface of circulating leukocytes and in the CNV lesions. (see, e.g., Examples 7 and 8). The results presented in these examples show that 17,18-EEQ and 19,20-EDP down-regulate peripheral blood leukocyte adhesion ability. The interaction between β2-integrins on leukocytes and their endothelial ligands, such as ICAM-1 and E-selectin, is required for modulating adhesion, migration, and infiltration of leukocytes into inflammatory sites (41). Integrin CD11b/CD18, which consists of a heterodimer of the αM (CD11b) and β2 (CD18) subunits, is the most crucial β2-integrin for leukocyte recruitment (41). The present data shows that 17,18-EEQ and 19,20-EDP reduced CD11b/CD18 expression in PBLs, and that 17,18-EEQ reduced ICAM-1 and E-selectin expression in endothelial cells in CNV lesions (see, e.g., Example 7). These findings indicate that the inhibitory effect of 17,18-

EEQ and 19,20-EDP on CNV may be due to their inhibitory effect on leukocyte recruitment by reducing the expression of adherent molecules on both leukocytes and endothelial cells.

The major dietary ω-6 LCPUFA is arachidonic acid (AA). The results presented herein show that dietary intake of AA (see, e.g., Example 1-3) and direct administration of its epoxy metabolites (EETs) (see, e.g., Example 4) did not have a significant effect on CNV development. Rather, EETs promoted PBL adhesion, increased CD18 expression in PBLs, and increased ICAM-1 and E-selectin expression in endothelial cells in CNV lesions (see, e.g., Example 8). These results are consistent with the general idea that ω-6 LCPUFAs and their metabolites are pro-inflammatory as opposed to ω-3 LCPUFAs and their metabolites.

REFERENCES

1. Miller J W (2013) Age-related macular degeneration revisited—piecing the puzzle: the LXIX Edward Jackson memorial lecture. *Am J Ophthalmol* 155(1):1-35 e13.
2. Lim L S, Mitchell P, Seddon J M, Holz F G, & Wong T Y (2012) Age-related macular degeneration. *Lancet* 379 (9827):1728-1738.
3. Gragoudas E S, Adamis A P, Cunningham E T, Jr., Feinsod M, & Guyer D R (2004) Pegaptanib for neovascular age-related macular degeneration. *The New England journal of medicine* 351 (27): 2805-2816.
4. Ng E W & Adamis A P (2006) Anti-VEGF aptamer (pegaptanib) therapy for ocular vascular diseases. *Ann N Y Acad Sci* 1082:151-171.
5. Rosenfeld P J, et al. (2006) Ranibizumab for neovascular age-related macular degeneration. *N Engl J Med* 355 (14): 1419-1431.
6. Lois N, McBain V, Abdelkader E, Scott N W, & Kumari R (2013) Retinal pigment epithelial atrophy in patients with exudative age-related macular degeneration undergoing anti-vascular endothelial growth factor therapy. *Retina* 33(1):13-22.
7. SanGiovanni J P & Chew E Y (2005) The role of omega-3 long-chain polyunsaturated fatty acids in health and disease of the retina. *Prog Retin Eye Res* 24(1): 87-138.
8. Schmitz G & Ecker J (2008) The opposing effects of n-3 and n-6 fatty acids. *Prog Lipid Res* 47(2):147-155.
9. Serhan C N & Savill J (2005) Resolution of inflammation: the beginning programs the end. *Nature immunology* 6(12):1191-1197.
10. Funk C D (2001) Prostaglandins and leukotrienes: advances in eicosanoid biology. *Science* 294(5548):1871-1875.
11. Capra V, et al. (2015) Transcellular biosynthesis of eicosanoid lipid mediators. *Biochim Biophys Acta* 1851 (4): 377-382.
12. Arnold C, Konkel A, Fischer R, & Schunck W H (2010) Cytochrome P450-dependent metabolism of omega-6 and omega-3 long-chain polyunsaturated fatty acids. *Pharmacol Rep* 62(3):536-547.
13. Arnold C, et al. (2010) Arachidonic acid-metabolizing cytochrome P450 enzymes are targets of {omega}-3 fatty acids. *J Biol Chem* 285(43):32720-32733.
14. Askari A, Thomson S J, Edin M L, Zeldin D C, & Bishop-Bailey D (2013) Roles of the epoxygenase CYP2J2 in the endothelium. *Prostaglandins Other Lipid Mediat*.
15. Souied E H, et al. (2013) Oral Docosahexaenoic Acid in the Prevention of Exudative Age-Related Macular Degeneration: The Nutritional AMD Treatment 2 Study. *Ophthalmology*.
16. SanGiovanni J P, et al. (2013) DNA sequence variants in PPARGC1A, a gene encoding a coactivator of the omega-3 LCPUFA sensing PPAR-RXR transcription complex, are associated with N V AMD and AMD-associated loci in genes of complement and VEGF signaling pathways. *PLoS One* 8(1):e53155.
17. Reynolds R, Rosner B, & Seddon J M (2013) Dietary omega-3 Fatty acids, other fat intake, genetic susceptibility, and progression to incident geographic atrophy. *Ophthalmology* 120(5): 1020-1028.
18. Yanai R, et al. (2014) Cytochrome P450-generated metabolites derived from omega-3 fatty acids attenuate neovascularization. *Proc Natl Acad Sci USA* 111 (26): 9603-9608.
19. Edin M L, et al. (2011) Endothelial expression of human cytochrome P450 epoxygenase CYP2C8 increases susceptibility to ischemia-reperfusion injury in isolated mouse heart. *FASEB J* 25(10):3436-3447.
20. Wagner K, Vito S, Inceoglu B, & Hammock B D (2014) The role of long chain fatty acids and their epoxide metabolites in nociceptive signaling. *Prostaglandins Other Lipid Mediat* 113-115:2-12.
21. Rose T E, et al. (2010) 1-Aryl-3-(1-acylpiperidin-4-yl) urea inhibitors of human and murine soluble epoxide hydrolase: structure-activity relationships, pharmacokinetics, and reduction of inflammatory pain. *J Med Chem* 53(19):7067-7075.
22. Falck J R, et al. (2011) 17(R),18(S)-epoxyeicosatetraenoic acid, a potent eicosapentaenoic acid (EPA) derived regulator of cardiomyocyte contraction: structure-activity relationships and stable analogues. *J Med Chem* 54(12): 4109-4118.
23. Mitroulis I, et al. (2015) Leukocyte integrins: role in leukocyte recruitment and as therapeutic targets in inflammatory disease. *Pharmacol Ther* 147:123-135.
24. Ambati J & Fowler B J (2012) Mechanisms of age-related macular degeneration. *Neuron* 75(1):26-39.
25. Noda K, et al. (2008) Vascular adhesion protein-1 blockade suppresses choroidal neovascularization. *FASEB J* 22(8):2928-2935.
26. Mulki L, Sweigard J H, & Connor K M (2014) Assessing leukocyte-endothelial interactions under flow conditions in an ex vivo autoperfused microflow chamber assay. *J Vis Exp* (94).
27. Simmons D L, Batting R M, & Hla T (2004) Cyclooxygenase isozymes: the biology of prostaglandin synthesis and inhibition. *Pharmacol Rev* 56(3):387-437.
28. Rinaldo-Matthis A & Haeggstrom J Z (2010) Structures and mechanisms of enzymes in the leukotriene cascade. *Biochimie* 92(6):676-681.
29. Panigrahy D, Greene E R, Pozzi A, Wang D W, & Zeldin D C (2011) EET signaling in cancer. *Cancer Metastasis Rev* 30(3-4):525-540.
30. Wang D & Dubois R N (2012) Epoxyeicosatrienoic acids: a double-edged sword in cardiovascular diseases and cancer. *J Clin Invest* 122(1):19-22.
31. Imig J D (2012) Epoxides and soluble epoxide hydrolase in cardiovascular physiology. *Physiol Rev* 92(1): 101-130.
32. Arnold C, Konkel A, Fischer R, & Schunck W H (2010) Cytochrome P450-dependent metabolism of omega-6 and omega-3 long-chain polyunsaturated fatty acids. *Pharmacol Rep* 62(3):536-547.

33. Fer M, et al. (2008) Metabolism of eicosapentaenoic and docosahexaenoic acids by recombinant human cytochromes P450. *Arch Biochem Biophys* 471(2):116-125.
34. Westphal C, et al. (2013) CYP2J2 overexpression protects against arrhythmia susceptibility in cardiac hypertrophy. *PLoS One* 8(8):e73490.
35. Westphal C, Konkel A, & Schunck W H (2011) CYP-eicosanoids—a new link between omega-3 fatty acids and cardiac disease? *Prostaglandins Other Lipid Mediat* 96(1-4):99-108.
36. Cui P H, Petrovic N, & Murray M (2011) The omega-3 epoxide of eicosapentaenoic acid inhibits endothelial cell proliferation by p38 MAP kinase activation and cyclin D1/CDK4 down-regulation. *Br J Pharmacol* 162(5): 1143-1155.
37. Zhang G, et al. (2013) Epoxy metabolites of docosahexaenoic acid (DHA) inhibit angiogenesis, tumor growth, and metastasis. *Proc Natl Acad Sci USA* 110(16): 6530-6535.
38. Liu J Y, et al. (2013) Substituted phenyl groups improve the pharmacokinetic profile and anti-inflammatory effect of urea-based soluble epoxide hydrolase inhibitors in murine models. *Eur J Pharm Sci* 48(4-5):619-627.
39. Ulu A, et al. (2014) An omega-3 epoxide of docosahexaenoic acid lowers blood pressure in angiotensin-II-dependent hypertension. *J Cardiovasc Pharmacol* 64(1): 87-99.
40. Harris T R, et al. (2015) Inhibition of soluble epoxide hydrolase attenuates hepatic fibrosis and endoplasmic reticulum stress induced by carbon tetrachloride in mice. *Toxicol Appl Pharmacol* 286(2):102-111.
41. Ley K, Laudanna C, Cybulsky M I, & Nourshargh S (2007) Getting to the site of inflammation: the leukocyte adhesion cascade updated. *Nat Rev Immunol* 7 (9):678-689.
42. Sakurai E, et al. (2003) Targeted disruption of the CD18 or ICAM-1 gene inhibits choroidal neovascularization. *Invest Ophthalmol Vis Sci* 44(6):2743-2749.
43. Panigrahy D, Greene E R, Pozzi A, Wang D W, & Zeldin D C (2011) EET signaling in cancer. *Cancer Metastasis Rev* 30(3-4):525-540.
44. Wang D & Dubois R N (2010) Eicosanoids and cancer. *Nat Rev Cancer* 10(3):181-193.
45. Hui Y, et al. (2010) Targeted deletions of cyclooxygenase-2 and atherogenesis in mice. *Circulation* 121(24): 2654-2660.
46. Wang M, et al. (2011) Microsomal prostaglandin e2 synthase-1 modulates the response to vascular injury. *Circulation* 123(6):631-639.
47. Wang Y, et al. (2005) Arachidonic acid epoxygenase metabolites stimulate endothelial cell growth and angiogenesis via mitogen-activated protein kinase and phosphatidylinositol 3-kinase/Akt signaling pathways. *J Pharmacol Exp Ther* 314(2):522-532.
48. Webler A C, et al. (2008) Epoxyeicosatrienoic acids are part of the VEGF-activated signaling cascade leading to angiogenesis. *Am J Physiol Cell Physiol* 295(5):C1292-1301.
49. Pritchard K A, Jr., Tota R R, Stemerman M B, & Wong P Y (1990) 14, 15-Epoxyeicosatrienoic acid promotes endothelial cell dependent adhesion of human monocytic tumor U937 cells. *Biochem Biophys Res Commun* 167 (1):137-142.
50. Node K, et al. (1999) Anti-inflammatory properties of cytochrome P450 epoxygenase-derived eicosanoids. *Science* 285(5431):1276-1279.
51. Deng Y, et al. (2011) Endothelial CYP epoxygenase overexpression and soluble epoxide hydrolase disruption attenuate acute vascular inflammatory responses in mice. *FASEB J* 25(2):703-713.
52. Falck J R, et al. (2003) 11,12-epoxyeicosatrienoic acid (11,12-EET): structural determinants for inhibition of TNF-alpha-induced VCAM-1 expression. *Bioorg Med Chem Lett* 13(22):4011-4014.
53. Seddon J M, et al. (2001) Dietary fat and risk for advanced age-related macular degeneration. *Archives of ophthalmology* 119(8): 1191-1199.
54. Smith W, Mitchell P, & Leeder S R (2000) Dietary fat and fish intake and age-related maculopathy. *Archives of ophthalmology* 118(3):401-404.
55. Anonymous (2013) Lutein+Zeaxanthin and Omega-3 Fatty Acids for Age-Related Macular Degeneration: The Age-Related Eye Disease Study 2 (AREDS2) Randomized Clinical Trial. *JAMA:* 1-11.
56. Merle B M, et al. (2014) Circulating omega-3 fatty acids and neovascular age-related macular degeneration. *Investigative ophthalmology & visual science*.
57. SanGiovanni J P, et al. (2007) The relationship of dietary lipid intake and age-related macular degeneration in a case-control study: AREDS Report No. 20. *Archives of ophthalmology* 125 (5): 671-679.
58. Merle B M, et al. (2014) Circulating omega-3 Fatty acids and neovascular age-related macular degeneration. *Invest Ophthalmol Vis Sci* 55(3):2010-2019.
59. Souied E H, et al. (2013) Oral docosahexaenoic acid in the prevention of exudative age-related macular degeneration: the Nutritional AMD Treatment 2 study. *Ophthalmology* 120(8): 1619-1631.
60. Lee C R, et al. (2010) Endothelial expression of human cytochrome P450 epoxygenases lowers blood pressure and attenuates hypertension-induced renal injury in mice. *FASEB J* 24(10):3770-3781.
61. Sinal C J, et al. (2000) Targeted disruption of soluble epoxide hydrolase reveals a role in blood pressure regulation. *J Biol Chem* 275(51):40504-40510.
62. Arnold C, et al. (2010) Arachidonic acid-metabolizing cytochrome P450 enzymes are targets of {omega}-3 fatty acids. *J Biol Chem* 285(43):32720-32733.
63. Almulki L, et al. (2009) Surprising up-regulation of P-selectin glycoprotein ligand-1 (PSGL-1) in endotoxin-induced uveitis. *FASEB J* 23(3):929-939.
64. Hafezi-Moghadam A, Thomas K L, & Cornelssen C (2004) A novel mouse-driven ex vivo flow chamber for the study of leukocyte and platelet function. *Am J Physiol Cell Physiol* 286(4):$C_{876-892}$.
65. Ota, K. and B. D. Hammock. 1980. Cytosolic and microsomal epoxide hydrolases: differential properties in mammalian liver. Science. 207:1479-1481.
66. Borhan, B., A. D. Jones, F. Pinot, D. F. Grant, M. J. Kurth and B. D. Hammock. 1995. Mechanism of soluble epoxide hydrolase: Formation of an a-hydroxy ester-enzyme intermediate through Asp-333. J. Biol. Chem. 270(45): 26923-26930.
67. Morisseau C, Hammock B D (2013) Impact of soluble epoxide hydrolase and epoxyeicosanoids on human health. Annu. Rev. Pharmacol. Toxicol. 53:37-58.
68. Lee, K. S. S., J. Y. Liu, K. Wagner, S. Pakhomova, H. Dong, C. Morissuea, J. Yang, P. Wang, A. Ulu, C. Mate, L. Nguyen, S. H. Hwang, M. Edin, A. Mara, H. Wulff, M. Newcomer, D. Zeldin and B. D. Hammock. 2014 Optimized inhibitors of soluble epoxide hydrolase improve in vitro target residence time and in vivo efficacy. J Med Chem. 57(16):7016-30.

69. Morisseau, C., M. H. Goodrow, D. Dowdy, J. Zheng, J. F. Greene, J. R. Sanborn, and B. D. Hammock. 1999. Potent urea and carbamate inhibitors of soluble epoxide hydrolases. Proc. Natl. Acad. Sci. USA 96(16):8849-8854.
70. Shen H C and Hammock B D (2012) Discovery of inhibitors of soluble epoxide hydrolase: a target with multiple potential therapeutic indications. J. Med. Chem. 55(5):1789-1808.
71. Lee, K. S. S., C. Morisseau, J. Yang, P. Wang, S. H. Hwang and B. D. Hammock. 2013. Förster resonance energy transfer (FRET) competitive displacement assay for human soluble epoxide hydrolase. Anal Biochem. 434(2):259-268.
72. Sirish, P., N. Li, J. Y. Liu, K. S. S. Lee, S. H. Hwang, H. Qiu, S. M. Ma, J. E. Lópezl, B. D. Hammock and N. Chiamvimonvat. 2013. Unique mechanistic insights into the beneficial effects of soluble epoxide hydrolase inhibitors in the prevention of cardiac fibrosis. Proc Natl Acad Sci U.S.A. 110(14):5618-23.
73. Zhou, Y., G. Y. Sun, T. Liu, J. X. Duan, H. F. Zhou, K. S. S. Lee, B. D. Hammock, X. Fang, J. X. Jiang and C. X. Guan. 2015. Soluble epoxide hydrolase inhibitor 1-trifluoromethoxyphenyl-3-(1-propionylpiperidin-4-yl) urea attenuates bleomycin-induced pulmonary fibrosis in mice. Cell Tissue Res. Epub ahead of print. August 2015. PMID: 26310139.
74. Yu, Z., Xu, F., Huse, L. M., Morisseau, C., Draper, A., Newman, J. W., Parker, C., Graham, L., Engler, M., Hammock, B. D., Zeldin, D. C., and Kroetz, D. L. Soluble Epoxide Hydrolase Regulates Hydrolysis of Vasoactive Epoxyeicosatrienoic Acids. Circulation Research 87: 992-998, 2000.
75. Stahl, A., Sapieha, M., Connor, K. M., SanGiovanni, JP., Chen, J., Aderman, C., Willett, K., Krah, N., Dennison, R., Seaward, M., Guerin, K., Hua, J., Smith, L. E. PPARγ mediates the anti-angiogenic effects of ω3-PUFAs in proliferative retinopathy. Circulation Research. 2010; 107 (4):495-500.
76. Sapieha P, Stahl A, Chen J, Seaward M R, Willett K L, Krah N M, Dennison R J, Connor K M, Aderman C M, Liclican E, Carughi A, Perelman D, Kanaoka Y, Sangiovanni J P, Gronert K, Smith L E. 5-Lipoxygenase Metabolite 4-HDHA Is a Mediator of the Antiangiogenic Effect of {omega}-3 Polyunsaturated Fatty Acids. Science Translational Medicine. 2011; 3(69):69ra12.
77. Connor, K. M., SanGiovanni, J P., Lofqvist, C., Aderman, C. M., Chen, J., Higuchi, A., Hong, S., Pravda, E. A., Majchrzak, S., Carper, D., Hellstrom, A., Kang, J. X., Chew, E. Y., Salem, N, Jr., Serhan, C. N., Smith, L. E. H. Increased dietary intake of omega-3-polyunsaturated fatty acids reduces pathological retinal angiogenesis. Nature Medicine. 2007; 13(7):868-73.
78. Schunck, R. N., Theken, K. N., Edin, M. L., Caughey, M., ZBass, A., Ellis, K., Tran, B., Steele, S., Simmons, B Z. P., Lih, F. B., Tomer, K. B., Wu, M. C., Hinderliter, A. L., Stouffer, G. A., Zeldin, D. C. and Lee, C. R. Cytochrome P450 Derived Eicosanoids and Vascular Function in Coronary Artery Disease Patients. Atherosclerosis. 227: 442-448 2013.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A method of treating or reducing the risk of an ophthalmological disorder associated with neovascularization, the method comprising administering to a subject in need thereof a therapeutically effective amount of an epoxydocosapentaenoic acid (EDP) or an epoxyeicosatetraenoic acid (EEQ), or a pharmaceutically acceptable salt thereof, and an effective amount of an inhibitor of a soluble epoxide hydrolase which is 1-trifluoromethoxyphenyl-3-(1-propionylpiperidin-4-yl) urea having the following structure:

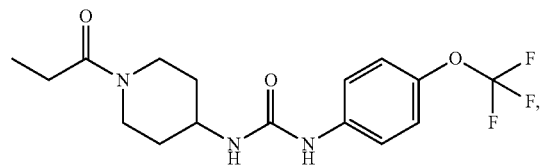 [SMILES: CCC(=O)N1CCC(NC(=O)Nc2ccc(OC(F)(F)F)cc2)CC1]

or a pharmaceutically acceptable salt thereof.

2. A method of treating or reducing the risk of an ophthalmological disorder associated with neovascularization, the method comprising administering to a subject in need thereof a therapeutically effective amount of:
an epoxymetabolite of a ω-3 long chain polyunsaturated fatty acid (LCPUFA) selected from the group consisting of:

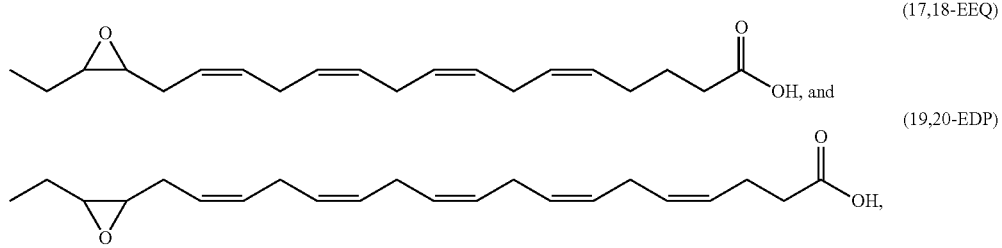

or a pharmaceutically acceptable salt thereof, and
an inhibitor of a soluble epoxide hydrolase which is 1-trifluoromethoxyphenyl-3-(1-propionylpiperidin-4-yl) urea having the following structure:

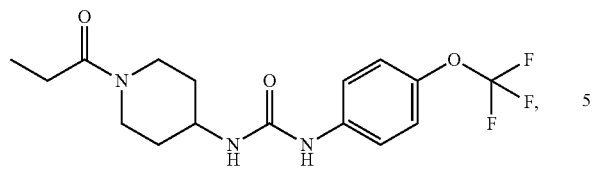
or a pharmaceutically acceptable salt thereof.
* * * * *

UNITED STATES PATENT AND TRADEMARK OFFICE
CERTIFICATE OF CORRECTION

PATENT NO. : 10,758,511 B2
APPLICATION NO. : 15/777141
DATED : September 1, 2020
INVENTOR(S) : Kip M. Connor et al.

Page 1 of 1

It is certified that error appears in the above-identified patent and that said Letters Patent is hereby corrected as shown below:

On the Title Page

In Column 2 (Other Publications), Line 25, delete "Phamacol," and insert -- Pharmacol, --

In the Specification

In Column 1, Line 8 (approx.), delete "20016," and insert -- 2016, --

In the Claims

In Column 70, Line 45 (approx.), Claim 2, delete "of:" and insert -- of --

Signed and Sealed this
Second Day of February, 2021

Drew Hirshfeld
*Performing the Functions and Duties of the*
*Under Secretary of Commerce for Intellectual Property and*
*Director of the United States Patent and Trademark Office*